United States Patent
Hakonarson et al.

(10) Patent No.: US 10,519,501 B2
(45) Date of Patent: Dec. 31, 2019

(54) COMMON AND RARE GENETIC VARIATIONS ASSOCIATED WITH COMMON VARIABLE IMMUNODEFICIENCY (CVID) AND METHODS OF USE THEREOF FOR THE TREATMENT AND DIAGNOSIS OF THE SAME

(71) Applicant: The Children's Hospital of Philadelphia, Philadelphia, PA (US)

(72) Inventors: Hakon Hakonarson, Malvern, PA (US); Joseph Glessner, Mullica Hill, NJ (US); Jordan Orange, Norristown, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 346 days.

(21) Appl. No.: 14/829,312

(22) Filed: Aug. 18, 2015

(65) Prior Publication Data

US 2016/0046996 A1 Feb. 18, 2016

Related U.S. Application Data

(60) Division of application No. 13/802,142, filed on Mar. 13, 2013, now Pat. No. 9,109,254, which is a continuation-in-part of application No. PCT/US2011/051385, filed on Sep. 13, 2011.

(60) Provisional application No. 61/382,231, filed on Sep. 13, 2010.

(51) Int. Cl.
| | |
|---|---|
| C07H 21/02 | (2006.01) |
| C07H 21/04 | (2006.01) |
| C12M 1/34 | (2006.01) |
| C12Q 1/6883 | (2018.01) |
| G16B 35/00 | (2019.01) |
| G16C 20/60 | (2019.01) |
| A61K 38/20 | (2006.01) |
| C12Q 1/68 | (2018.01) |
| C12P 19/34 | (2006.01) |

(52) U.S. Cl.
CPC .......... *C12Q 1/6883* (2013.01); *A61K 38/208* (2013.01); *G16B 35/00* (2019.02); *G16C 20/60* (2019.02); *C12Q 2600/136* (2013.01); *C12Q 2600/156* (2013.01); *G01N 2500/10* (2013.01); *G01N 2800/24* (2013.01); *G01N 2800/50* (2013.01)

(58) Field of Classification Search
CPC ............ C12Q 1/6886; C12Q 2600/112; C12Q 2600/118; C12Q 2600/156
See application file for complete search history.

(56) References Cited

U.S. PATENT DOCUMENTS

2001/0053519 A1* 12/2001 Fodor .................. B01J 19/0046
435/6.11

OTHER PUBLICATIONS

Wang, K. et al. Genome Research, 17:1665-1674 (2007).*
LePinchon J.-B. et al. American Journal of Medical Genetics Part A (2010), pp. 1300-1304.*
DbSNP entry output for Reference SNP (refSNP) Cluster Report: rs2307394, from www.ncbi.nlm.nih.gov, 2 printed pages, printed on Jun. 5, 2018 (Year: 2018).*
Orange, J., et al. "Genome-wide association identifies diverse causes of common variable immunodeficiency." J Allergy Clin Immunol. Apr. 17, 2011;127(6):1360-7.
Uleand, T., et al. "Increased levels of biochemical markers fo bone turnover in relation to persistent immune activation in common variable immmunodeficiency." European Journal of Clinical Investigation. (2001) 31, 72-78.
Sheridan, C., et al. Can 'double blockbuster' strengthen Amgen's backbone? Nature Biotechnology (Apr. 2008) 26, 4, 361-363.

* cited by examiner

*Primary Examiner* — Stephen T Kapushoc
(74) *Attorney, Agent, or Firm* — Kathleen D. Rigaut; Howson & Howson LLP

(57) ABSTRACT

Compositions and methods useful for the diagnosis and treatment of common variable immunodeficiency are disclosed.

2 Claims, 26 Drawing Sheets

CNV Validation with Illumina Intensity Data Review and Independent Array Technology, Affymetrix 2.7M
Visual validation of all reported CNV loci using Illumina Quad 610 Intensity Data. Results from visual inspections are provided. Gray rectangle represents normal diploid two copy state.

Representative experimental validation of two of most significant deletions and two duplications, using Affymetrix 2.7M intensity data at a high resolution. Intensity values are plotted for each region listed based on samples with copy number variation calls.

Experimental validation of all Table 2 loci using Affymetrix 2.7M intensity data. Intensity values are plotted for each region listed based on samples with copy number variation calls. Table 2 loci are labeled with corresponding intensity values for contiguous probes in the genomic region.

COMMON AND RARE GENETIC VARIATIONS ASSOCIATED WITH COMMON VARIABLE IMMUNODEFICIENCY (CVID) AND METHODS OF USE THEREOF FOR THE TREATMENT AND DIAGNOSIS OF THE SAME

This application is a continuation in part application of PCT/US2011/051385 filed Sep. 13, 2011 which in turn claims priority to U.S. Provisional Application 61/382,231 filed Sep. 13, 2010, which is incorporated herein by reference as though set forth in full.

This invention relates to the fields of genetics and the diagnosis of common variable immunodeficiency (CVID). More specifically, the invention provides compositions and methods useful for the diagnosis and treatment of CVID.

BACKGROUND OF THE INVENTION

Several publications and patent documents are cited through the specification in order to describe the state of the art to which this invention pertains. Each of these citations is incorporated herein by reference as though set forth in full.

Common variable immunodeficiency (CVID) disorders are manifested by insufficient quantity and quality of immunoglobulin leading to susceptibility to bacterial infections[1]. CVID is considered to be a primary immunodeficiency disease (PIDD) as it is believed to result from intrinsic deficits affecting immunological functions. CVID is heterogeneous in presentation, presenting either early or later in life and associated with a group of known comorbidities[2]. Efforts to subcategorize CVID in order to predict outcomes and comorbid conditions both clinically and by immunologic phenotypes are ongoing[3]. BAFFR[4], TACI[5,6,7], and certain HLA haplotypes[8,9] have been identified as potential gene candidates for susceptibility to CVID. ICOS[10,11], CD81[12], CD19[13,14], CD20[15], harbor disease causing mutations that presently explain only a small percentage of cases. The heterogeneous presentations of patients with CVID make management of these conditions difficult and searches for novel genetic predictors of disease causation or susceptibility have been of limited success.

SUMMARY OF THE INVENTION

In accordance with the present invention, methods are provided for the diagnosis and treatment of CVID. An exemplary method entails detecting the presence of at least one CVID associated CNV in a target polynucleotide wherein if said CNV(s) is/are present, said patient has an increased risk for developing CVID.

In one aspect of the present invention, a method for detecting a propensity for developing common variable immunodeficiency disorder (CVID) in a patient in need thereof is provided. An exemplary method entails detecting the presence of at least one SNP containing nucleic acid in a target polynucleotide, said SNP being informative of a the presence of a CVID associated copy number variation (CNV), wherein if said SNP is present, said patient has an increased risk for developing CVID, wherein said SNP containing nucleic acid is provided in Tables 1 to 5. In one embodiment, at least 1, 2, 3, 4, 5, 10, 15, 20 or all of the SNPs provided herein are detected.

In another embodiment of the invention a method for identifying agents which alter immune cell function or signaling is provided. Such a method comprises providing cells expressing at least one nucleic acid comprising the CVID associated CNVs of the invention, (step a); providing cells which express the cognate wild type sequences which lack the CNV (step b); contacting the cells from each sample with a test agent and analyzing whether said agent alters immune signaling or function of cells of step a) relative to those of step b), thereby identifying agents which alter immune cell signaling or function. Methods of treating CVID patients via administration of test agents identified using the methods described herein are also encompassed by the present invention. The invention also provides at least one isolated CVID related SNP-containing nucleic acid selected from the group listed in Tables 1 to 5. In one embodiment, a multiplex SNP panel containing all of the informative SNPs from the tables provided herein is disclosed. Such SNP containing nucleic acids which indicate the presence of CVID associated CNV(s) may optionally be contained in a suitable expression vector for expression in immune cells. Alternatively, they may be immobilized on a solid support. In yet another alternative embodiment, the panel may be provided in silico.

According to yet another aspect of the present invention, there is provided a method of treating CVID in a patient determined to have at least one prescribed single nucleotide polymorphism indicative of the presence of a CVID-associated copy number variation, as described hereinbelow, by administering to the patient a therapeutically effective amount of an agent useful for modulating immune function. This method provides a test and treat paradigm, whereby a patient's genetic profile is used to personalize treatment with therapeutics targeted towards specific gastrointestinal defects found in individuals exhibiting CVID. Such a test and treat model may benefit up to 50% of patients with CVID with greater efficacy and fewer side effects than non-personalized treatment.

DETAILED DESCRIPTION OF THE INVENTION

Figure 1A:
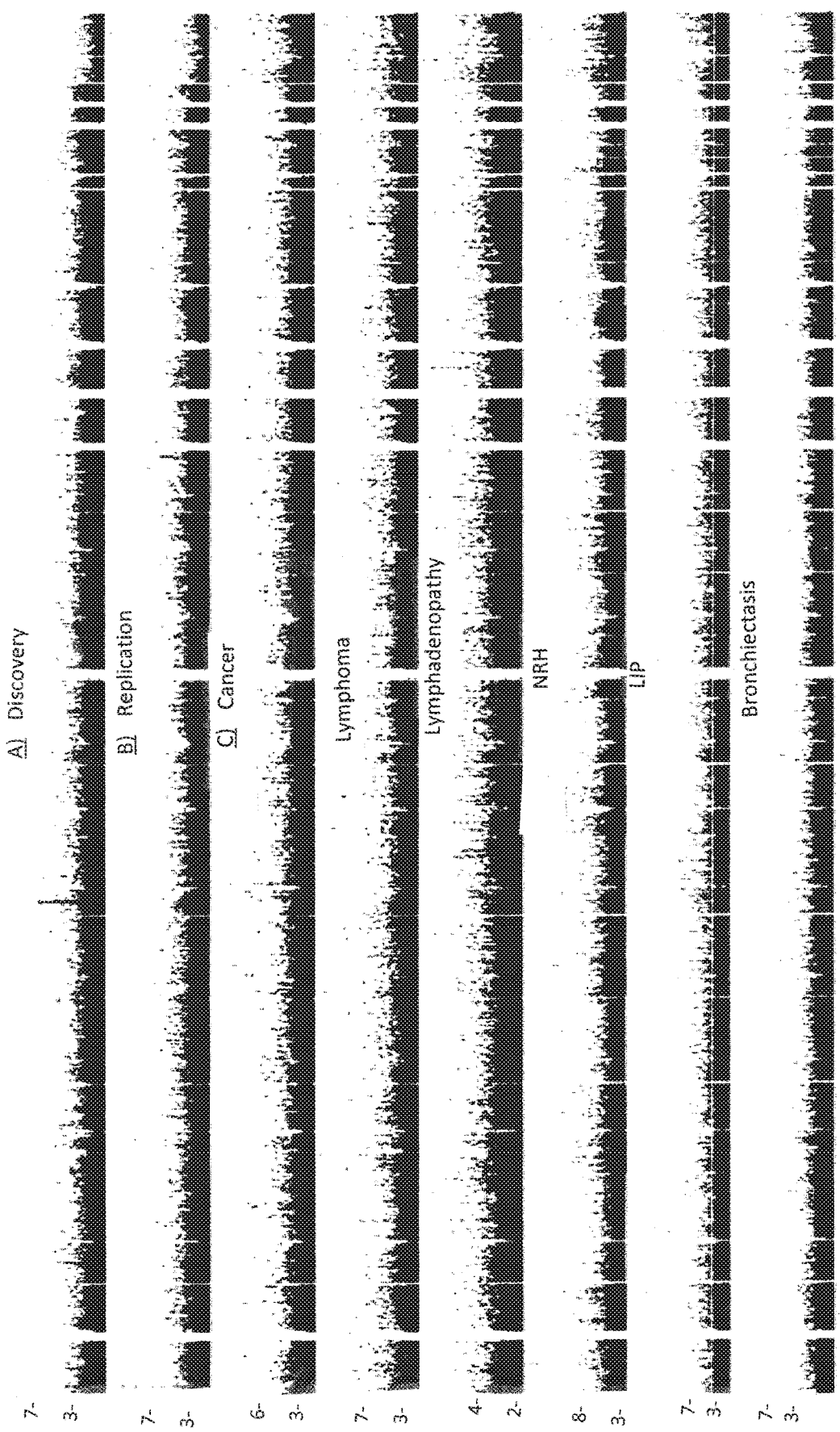
FIGS. 1A-1C. SNP based case:control significance is shown in negative log base 10 genome wide for Discovery (FIG. 1A) and Replication (FIG. 1B and FIG. 1C) inclusive CVID cohorts. Subsequently, CVID cases with specific disease subphenotypes were compared to CVID cases without the subphenotype. The single SNP tests are shown as single points. Multiple neighboring SNPs of similar significance boost confidence in the association as shown in the strong peak on 6p22.1-p21.32 of the Discovery case:control cohort. Conversely the median significance P value is kept low by minimizing population stratification which minimizes the genomic inflation factor.

Common variable immunodeficiency disorders (CVID) are a group of uncommon heterogeneous immune defects characterized by hypogammaglobulinemia, failure of antibody production, susceptibility to bacterial infections and an array of serious comorbidities. To address the underlying immunopathogeneses of CVID, we conducted the first genome-wide association study of patients with CVID. 363 patients were genotyped with 610,000 SNPs. Due to the relative rarity of this group of disorders, the study cohort was recruited at four sites. Patients were randomly divided into a discovery cohort of 179 cases in comparison with 1,917 disease-free controls and a replication cohort of 109 cases in comparison with 1,114 controls, controlled for population stratification. Our analyses detected strong association with the MHC region and uncovered a novel association with a cluster of ADAM genes that was replicated in the independent case cohort. Analysis of the same cases for copy number variation (CNV) revealed 16 disease-associated deletions and duplications, as well as numerous unique rare intraexonic deletions and duplications suggesting multiple novel genetic etiologies for individual CVID cases. Analysis of CVID comorbidities identified significantly associated SNP genotypes with the major CVID clinical phenotypes. Taken together, our integrative genome-wide analysis of SNP genotypes and CNVs has uncovered multiple novel susceptibility loci for CVID, both common and rare, consistent with the highly heterogeneous nature of CVID. These results may allow for improved diagnosis of CVID, prediction of the CVID clinical phenotypes, and mechanistic insights into immune diseases based upon these unique genetic variations.

I. Definitions

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

The term "genetic alteration" as used herein refers to a change from the wild-type or reference sequence of one or more nucleic acid molecules. Genetic alterations include without limitation, base pair substitutions, additions and deletions of at least one nucleotide from a nucleic acid molecule of known sequence.

A "single nucleotide polymorphism (SNP)" refers to a change in which a single base in the DNA differs from the usual base at that position. These single base changes are called SNPs or "snips." Millions of SNP's have been cataloged in the human genome. Some SNPs such as that which causes sickle cell are responsible for disease. Other SNPs are normal variations in the genome. Frequently SNPs are used to "mark" particular genes and genetic regions, particularly those containing CNVs for example.

A "copy number variation (CNV)" refers to the number of copies of a particular gene or segment thereof in the genome of an individual. CNVs represent a major genetic component of human phenotypic diversity. Susceptibility to genetic disorders is known to be associated not only with single nucleotide polymorphisms (SNP), but also with structural and other genetic variations, including CNVs. A CNV represents a copy number change involving a DNA fragment that is ~1 kilobases (kb) or larger. CNVs described herein do not include those variants that arise from the insertion/deletion of transposable elements (e.g., ~6-kb KpnI repeats) to minimize the complexity of future CNV analyses. The term CNV therefore encompasses previously introduced terms such as large-scale copy number variants (LCVs), copy number polymorphisms (CNPs), and intermediate-sized variants (ISVs), but not retroposon insertions. The terminology "duplication-containing CNV" is also used herein below consistent with the CNV definition provided.

"CVID-associated SNP" or "CVID-associated specific marker" is a SNP or marker which is associated with an increased or decreased risk of developing CVID not found normal patients who do not have this disease. Such markers may include but are not limited to nucleic acids, proteins encoded thereby, or other small molecules. Thus, the phrase "CVID-associated SNP containing nucleic acid" is encompassed by the above description.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the functional and novel characteristics of the sequence.

The phrase "partial informative CNV" is used herein to refer to a nucleic acid that hybridizes to sequences comprising a duplication on a chromosome however, the partial informative CNV may not be identical to the duplication, rather, the CNV may correspond to only a portion of the duplication, but yet is still informative for the presence of the same.

"Target nucleic acid" as used herein refers to a previously defined region of a nucleic acid present in a complex nucleic acid mixture wherein the defined wild-type region contains at least one known nucleotide variation which may or may not be associated with CVID. The nucleic acid molecule may be isolated from a natural source by cDNA cloning or subtractive hybridization or synthesized manually. The nucleic acid molecule may be synthesized manually by the triester synthetic method or by using an automated DNA synthesizer. With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^{-6}$-fold purification of the native message. Thus, purification of at least one order of magnitude, preferably two or three orders, and more preferably four or five orders of magnitude is expressly contemplated. Thus the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any CVID specific marker gene or nucleic acid, but does not hybridize to other nucleotides. Also polynucleotide which "specifically hybridizes" may hybridize only to a single specific marker, such as an CVID-specific marker shown in the Tables contained herein. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., Molecular Cloning, Cold Spring Harbor Laboratory (1989):

$$T_m = 81.5° \text{ C.} + 16.6 \text{ Log}[Na+] + 0.41(\% \ G+C) - 0.63 \ (\% \text{ formamide}) - 600/\# \text{ bp in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide," as used herein is defined as a nucleic acid molecule comprised of two or more ribo- or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the CVID specific marker nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the CVID specific marker nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus, that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism" or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

"Sample" or "patient sample" or "biological sample" generally refers to a sample which may be tested for a particular molecule, preferably a CVID specific marker molecule, such as a marker described hereinbelow. Samples may include but are not limited to cells, body fluids, including blood, serum, plasma, cerebral spinal fluid, urine, gastric lavage, saliva, tears, pleural fluid and the like.

The terms "agent" and "compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, peptides, peptide/DNA complexes, and any nucleic acid based molecule which exhibits the capacity to modulate the activity of the CNV or SNP-containing nucleic acids described herein or their encoded proteins. Agents and compounds may also be referred to as "test agents" or "test compounds" which are evaluated for potential biological activity by inclusion in screening assays described hereinbelow.

The term "modulate" as used herein refers to increasing/promoting or decreasing/inhibiting a particular cellular, biological or signaling function associated with the normal activities of the genetic alteration containing molecules described herein or the proteins encoded thereby. For example, the term modulate refers to the ability of a test compound or test agent to interfere with signaling or activity of a gene or protein of the present invention. Alternatively, the term may refer to augmentation of the activity of such a protein.

II. Methods of Using CVID-Associated CNVs and/or SNPs for Diagnosing a Propensity for the Development of CVID The present invention provides methods of diagnosing CVID in a patient or methods for identifying a patient having an increased risk of developing CVID. Diagnosis, as used herein, includes not only the initial identification of CVID-associated with the genetic alterations described herein in a patient but confirmatory testing, or screening in patients who have previously been identified as having or likely to have CVID. The methods include the steps of providing a biological sample from the patient, measuring the amount of particular sets (e.g., those with the highest statistical significance), 1, 2, 3, 4, 5, 10, 10, 20 or all of the CVID associated markers (Tables herein) present in the biological sample, preferably a tissue and/or blood plasma sample, and determining if the patient has a greater likelihood of having or developing CVID based on the amount and/or type of CVID marker expression level determined relative to those expression levels identified in patient cohorts of known outcome. A patient has a greater likelihood of having CVID when the sample has a CNV marker expression profile associated with patients previously diagnosed with CVID. The compositions and methods of the invention are useful for the prognosis and diagnosis and management of CVID.

In another aspect, the patient sample may have been previously genotyped and thus the genetic expression profile in the sample may be available to the clinician. Accordingly, the method may entail storing reference CVID associated marker sequence information in a database, i.e., those CNVs statistically associated with a more favorable or less favorable prognosis as described in the tables herein, and performance of comparative genetic analysis on the computer, thereby identifying those patients having increased risk of CVID.

CVID-related CNV or SNP-containing nucleic acids, including but not limited to those listed below may be used for a variety of purposes in accordance with the present invention. CVID-associated CNV or SNP-containing DNA, RNA, or fragments thereof may be used as probes to detect the presence of and/or expression of CVID specific markers. Methods in which CVID specific marker nucleic acids may be utilized as probes for such assays include, but are not limited to: (1) in situ hybridization; (2) Southern hybridization (3) northern hybridization; and (4) assorted amplification reactions such as polymerase chain reactions (PCR).

Further, assays for detecting CVID-associated CNVs or SNPs may be conducted on any type of biological sample, including but not limited to body fluids (including blood, urine, serum, gastric lavage, cerebral spinal fluid), any type of cell (such as brain cells, white blood cells, mononuclear cells, fetal cells in maternal circulation) or body tissue.

Clearly, CVID-associated CNV or SNP-containing nucleic acids, vectors expressing the same, CVID CNV or SNP-containing marker proteins and anti-CVID specific marker antibodies of the invention can be used to detect CVID associated CNVs or SNPs in body tissue, cells, or fluid, and alter CVID CNV or SNP-containing marker protein expression for purposes of assessing the genetic and protein interactions involved in the development of CVID.

In most embodiments for screening for CVID-associated CNVs or SNPs, the CVID-associated CNV or SNP-containing nucleic acid in the sample will initially be amplified, e.g. using PCR, to increase the amount of the templates as compared to other sequences present in the sample. This allows the target sequences to be detected with a high degree of sensitivity if they are present in the sample. This initial step may be avoided by using highly sensitive array techniques that are important in the art.

Alternatively, new detection technologies can overcome this limitation and enable analysis of small samples containing as little as 1 µg of total RNA. Using Resonance Light Scattering (RLS) technology, as opposed to traditional fluorescence techniques, multiple reads can detect low quantities of mRNAs using biotin labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

Any of the aforementioned techniques may be used to detect or quantify CVID-associated CNV or SNP marker expression and accordingly, diagnose an increased risk for developing the same.

III. Kits and Articles of Manufacture

Any of the aforementioned products can be incorporated into a kit which may contain a CVID-associated CNV or SNP specific marker polynucleotide or one or more such markers immobilized on a solid support or Gene Chip, provided in silico in a database, one or more oligonucleotides, a polypeptide, a peptide, an antibody, a label, marker, reporter, a pharmaceutically acceptable carrier, reagents suitable for performance of PCR with positive and negative control nucleic acids, a physiologically acceptable carrier, instructions for use, a container, a vessel for administration, an assay substrate, or any combination thereof.

IV. Methods of Using CVID-Associated CNVs and/or SNPs for the Development of Therapeutic Agents Since the CNVs and SNPs identified herein have been associated with the etiology of CVID, methods for identifying agents that modulate the activity of the genes and their encoded products containing such CNVs and/or SNPs should result in the generation of efficacious therapeutic agents for the treatment of this disorder.

Several regions of the human genome provide suitable targets for the rational design of therapeutic agents. Small nucleic acid molecules or peptide molecules corresponding to these regions may be used to advantage in the design of therapeutic agents that effectively modulate the activity of the encoded proteins.

Molecular modeling should facilitate the identification of specific organic molecules with capacity to bind to the active site of the proteins encoded by the CNV or SNP-containing nucleic acids based on conformation or key amino acid residues required for function. A combinatorial chemistry approach will be used to identify molecules with greatest activity and then iterations of these molecules will be developed for further cycles of screening. Molecules available for testing in this screening assay, include without limitation, Apilimod Mesylate (STA-5326), an oral small-molecule compound that selectively inhibits the production of the IL-12 family of proteins Inhibition of IL-production may improve the gastrointestinal manifestations of CVID. Apilimod mesylate selectively inhibits this pathway and reduces over-production of IL-12 and IL-23. Other agents that may have therapeutic utility for treating CVID symptoms include the ACVR2A antagonist Sotaercept and the ACVR antibody PF3446962 as ACVR2A exhibits a significant CNV duplication associated with CVID. PEG-interleukin-2 and B-lymphocyte stimulators may also be screened for therapeutic utility in the treatment of CVID. The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between the polypeptide or fragment and the agent being tested, or examine the degree to which the formation of a complex between the polypeptide or fragment and a known substrate is interfered with by the agent being tested.

Another technique for drug screening provides high throughput screening for compounds having suitable binding affinity for the encoded polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with the target polypeptide and washed. Bound polypeptide is then detected by methods well known in the art.

A further technique for drug screening involves the use of host eukaryotic cell lines or cells (such as described above) which have a nonfunctional or altered CVID associated gene. These host cell lines or cells are defective at the polypeptide level. The host cell lines or cells are grown in the presence of drug compound. Altered immune signaling or function of the host cells is measured to determine if the compound is capable of regulating this function in the defective cells. Host cells contemplated for use in the present invention include but are not limited to bacterial cells, fungal cells, insect cells, mammalian cells, and plant cells. However, mammalian cells, particularly immune cells are preferred. The CVID-associated CNV or SNP encoding DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., Current Protocols in Molecular Biology, John Wiley & Sons, NY, N.Y. 1995, the disclosure of which is incorporated by reference herein.

A wide variety of expression vectors are available that can be modified to express the novel DNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in Saccharomyces are also described in Current Protocols in Molecular Biology (1989).

Suitable vectors for use in practicing the invention include prokaryotic vectors such as the pNH vectors (Stratagene Inc., 11099 N. Torrey Pines Rd., La Jolla, Calif. 92037), pET vectors (Novogen Inc., 565 Science Dr., Madison, Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); pcDNA3.1/V5&His (Invitrogen); baculovirus vectors such as pVL1392, pVL1393, or pAC360 (Invitrogen); and yeast vectors such as YRP17, YIPS, and YEP24 (New England Biolabs, Beverly, Mass.), as well as pRS403 and pRS413 Stratagene Inc.); Picchia vectors such as pHIL-D1 (Phillips Petroleum Co., Bartlesville, Okla. 74004); retroviral vectors such as PLNCX and pLPCX (Clontech); and adenoviral and adeno-associated viral vectors.

Promoters for use in expression vectors of this invention include promoters that are operable in prokaryotic or eukaryotic cells. Promoters that are operable in prokaryotic cells include lactose (lac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, adenovirus promoters, SV40 promoters, Rous Sarcoma Virus promoters, cytomegalovirus (CMV) promoters, baculovirus promoters such as AcMNPV polyhedrin promoter, Picchia promoters such as the alcohol oxidase promoter, and Saccharomyces promoters such as the gal4 inducible promoter and the PGK constitutive promoter, as well as neuronal-specific platelet-derived growth factor promoter (PDGF), the Thy-1 promoter, the hamster and mouse Prion promoter (MoPrP), and the Glial fibrillar acidic protein (GFAP) for the expression of transgenes in glial cells.

In addition, a vector of this invention may contain any one of a number of various markers facilitating the selection of a transformed host cell. Such markers include genes associated with temperature sensitivity, drug resistance, or enzymes associated with phenotypic characteristics of the host organisms.

Host cells expressing the CVID-associated CNVs and/or SNPs of the present invention or functional fragments thereof provide a system in which to screen potential compounds or agents for the ability to modulate the development of CVID. Thus, in one embodiment, the nucleic acid molecules of the invention may be used to create recombinant cell lines for use in assays to identify agents which modulate aspects of cellular metabolism associated with CVID and aberrant glutaminergic function. Also provided herein are methods to screen for compounds capable of modulating the function of proteins encoded by CNV and SNP-containing nucleic acids.

Another approach entails the use of phage display libraries engineered to express fragment of the polypeptides encoded by the CNV or SNP-containing nucleic acids on the phage surface. Such libraries are then contacted with a combinatorial chemical library under conditions wherein binding affinity between the expressed peptide and the components of the chemical library may be detected. U.S. Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides may be analyzed by an alanine scan (Wells, (1991) Meth. Enzym. 202:390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based.

One can bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., improved polypeptide activity or stability or which act as inhibitors, agonists, antagonists, etc. of polypeptide activity. By virtue of the availability of CNV or SNP-containing nucleic acid sequences described herein, sufficient amounts of the encoded polypeptide may be made available to perform such analytical studies as x-ray crystallography. In addition, the knowledge of the protein sequence provided herein will guide those employing computer modeling techniques in place of, or in addition to x-ray crystallography.

In another embodiment, the availability of CVID-associated CNV or SNP-containing nucleic acids enables the production of strains of laboratory mice carrying the CVID-associated SNPs or CNVs of the invention. Transgenic mice expressing the CVID-associated CNV or SNP of the invention provide a model system in which to examine the role of the protein encoded by the CNV or SNP-containing nucleic acid in the development and progression towards CVID. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role that a target protein plays in various cellular metabolic processes, including: aberrant antibody production and function, altered immunoreceptor ligand signaling and aberrant responses to bacterial and viral infections. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of CVID-associated CNV or SNP-containing nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated CVID-associated CNV or SNP genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$ fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabinofluranosyl)-5-iodou-racil, (FIAU). By this counter selection, the number of homologous recombinants in the surviving transformants can be increased. Utilizing CVID-associated CNV or SNP-containing nucleic acid as a targeted insertional cassette provides means to detect a successful insertion as visualized, for example, by acquisition of immunoreactivity to an antibody immunologically specific for the polypeptide encoded by CVID-associated CNV or SNP nucleic acid and, therefore, facilitates screening/selection of ES cells with the desired genotype.

As used herein, a knock-in animal is one in which the endogenous murine gene, for example, has been replaced with human CVID-associated CNV or informative fragment thereof or SNP-containing gene of the invention. Such knock-in animals provide an ideal model system for studying the development of CVID.

As used herein, the expression of a CVID-associated CNV or SNP-containing nucleic acid, partial informative CNV fragment thereof, or an CVID-associated fusion protein in which the CNV or SNP is encoded can be targeted in a "tissue specific manner" or "cell type specific manner" using a vector in which nucleic acid sequences encoding all or a portion of an CVID-associated CNV or SNP are operably linked to regulatory sequences (e.g., promoters and/or enhancers) that direct expression of the encoded protein in a particular tissue or cell type. Such regulatory elements may be used to advantage for both in vitro and in vivo applications. Promoters for directing tissue specific proteins are well known in the art and described herein.

Methods of use for the transgenic mice of the invention are also provided herein. Transgenic mice into which a nucleic acid containing the CVID-associated CNV or SNP or its encoded protein have been introduced are useful, for example, to develop screening methods to screen therapeutic agents to identify those capable of modulating the development of CVID.

V. Pharmaceutical and Peptide Therapies

The elucidation of the role played by the CVID associated CNVs and SNPs described herein in immunoreceptor ligand signaling and function facilitates the development of pharmaceutical compositions useful for treatment and diagnosis of CVID. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

The following materials and methods are provided to facilitate the practice of the present invention.

Patients

The diagnosis of CVID was established in concordance with existing diagnostic criteria[16,38]. All patients were enrolled in institutionally approved research protocols to enable genetic analysis and collection of clinical data. Subsets of the patients reported here have been previously included in published studies[2,22,39].

Illumina Infinium Assay for SNP Genotyping and CNV Discovery

We performed high-throughput, genome-wide SNP genotyping, using the InfiniumII HumanHap550 BeadChip technology (Illumina San Diego, Calif.), at the Center for Applied Genomics at CHOP. The genotype data content together with the intensity data provided by the genotyping array provides high confidence for CNV calls. Importantly, the simultaneous analysis of intensity data and genotype data in the same experimental setting establishes a highly accurate definition for normal diploid states and any deviation from the norm. To call CNVs, we used the PennCNV algorithm[12], which combines multiple sources of information, including Log R Ratio (LRR) and B Allele Frequency (BAF) at each SNP marker, along with SNP spacing and population frequency of the B allele to generate CNV calls. Rare recurrent CNVs were the focus of our study.

CNV Quality Control

We calculated Quality Control (QC) measures on our HumanHap550 GWAS data based on statistical distributions to exclude poor quality DNA samples and false positive CNVs. The first threshold is the percentage of attempted SNPs which were successfully genotyped. Only samples with call rate >98% were included. The genome wide intensity signal must have as little noise as possible. Only samples with the standard deviation (SD) of normalized intensity (LRR) <0.35 were included. All samples must have Caucasian ethnicity based on principle components analysis and all other samples were excluded. Furthermore, case and control matching was insured by calculating a genomic inflation factor between groups. Wave artifacts roughly correlating with GC content resulting from hybridization bias of low full length DNA quantity are known to interfere with accurate inference of copy number variations. Only samples where the GC corrected wave factor of LRR $-0.02<x<0.02$ were accepted. If the count of CNV calls made by PennCNV exceeds 100, it is suggestive of poor DNA quality, and those samples were excluded. Thus, only samples with CNV call count <100 were included. Any duplicate samples (such as monozygotic twins or repeats on the same patient) were identified and as a result one sample was excluded.

Statistical Analysis of CNVs

CNV frequency between cases and controls was evaluated at each SNP using Fisher's exact test. We only considered loci that were nominally significant between cases and controls ($p<0.05$) for which patients had the same variation, that were observed in multiple cohorts or were not observed in any of the control subjects, and were validated with an independent method. We report statistical local minimums to narrow the association in reference to a region of nominal significance including SNPs residing within 1 Mb of each other. Resulting nominally significant CNVRs were excluded if they met any of the following criteria: i) residing on telomere or centromere proximal cytobands; ii) arising in a "peninsula" of common CNV arising from variation in boundary truncation of CNV calling; iii) genomic regions with extremes in GC content which produces hybridization bias; or iv) samples contributing to multiple CNVRs. Three lines of evidence establish statistical significance: independent replication p<0.05, permutation of observations, and no loci observed with control enriched significance. We used DAVID (Database for Annotation, Visualization, and Integrated Discovery)[42] to assess the significance of functional annotation clustering of independently associated results into InterPro categories.

The following examples are provided to illustrate certain embodiments of the invention. They are not intended to limit the invention in any way.

Example 1

Genome wide single nucleotide polymorphism (SNP) arrays have enabled high throughput typing of genomic DNA with tagging of the whole genome based on linkage disequilibrium. Given both intensity and genotype content, copy number variations (CNVs) can also be detected using the same GWAS platforms. Both SNPs and CNVs have a significant difference in frequency between cases and controls in a variety of diseases. We genotyped 363 CVID cases and 3,031 healthy controls on the Illumina Infinium HumanHap550K BeadChip. We sought to associate SNPs and CNVs with CVID[16], as well as with the characteristic clinical and immunologic phenotypes of this syndrome, to address disease heterogeneity. We additionally compared the CVID results with those obtained from Inflammatory Bowel Disease (IBD), another disease with an immunologic etiology but without susceptibility to infection, to serve as a "disease control" cohort and define associations unique to CVID subjects. Included in the cohort were 29 subjects with known mutations in TACI including 10 C104R, 8 A181E, 6 V220A and 1 occurrence of each of C104R/S144X, C104R/S194X, A181E/L171R, R72H, and S194X heterozygous.

Our CVID case cohort was composed of 223 patients from Mount Sinai School of Medicine, 76 patients from University of Oxford, 37 patients from The Children's Hospital of Philadelphia, and 27 patients from University of South Florida. The diagnosis in each case was validated against the ESID/PAGID diagnostic criteria[16] and only patients confirmed by these criteria were included.

We first evaluated quality and suitability of the data for a case control study. The primary parameters were sample based call rates and population based stratification. Seven samples had call rates lower than 98% and were excluded. Based on principle components analysis by Eigenstrat[17], the cases were stratified into three clusters: 179 cases were of confirmed European ancestry and another 109 Caucasian cases clustered separately, but very close to the other Caucasian cluster, whereas 30 samples were significant outliers from Caucasian and were omitted from this analysis. We also observed comparable clustering of the 179 cases to the 1,917 Caucasian controls. However, there were relatively few Caucasian controls that clustered well with the second Caucasian case cluster. To perform a more comprehensive search for additional control individuals that clustered with the latter case cohort, we ran 18,000 controls in 19 batches together with our cases through Eigenstrat. This identified over 1,000 control samples clustering similarly to the second Caucasian case cohort. We then reran those identified samples together with cases to yield a robustly stratified cluster with a total of 1,114 controls. This yielded a discovery cohort of 179 cases and 1,917 controls along with a replication cohort of 109 cases and 1,114 controls. We also excluded individuals with observed cryptic relatedness of genotypes as well as three known and two newly discovered 22q11 deletions. For CNV calling, samples with high noise (standard deviation of Log R Ratio >0.35) in intensity signal were additionally removed.

First, a genome wide association analysis (GWAS) was performed using the SNP genotype data. Genotype frequencies were compared between cases versus controls and a chi-square test statistic applied in Plink[18] for SNPs with at least 90% call rate and 1% minor allele frequency. The discovery cohort of 179 cases and 1,917 controls yielded a low genomic inflation factor of 1.02783 (FIG. 1A). The 1,000 most significant SNPs were evaluated for enrichment in genomic regions to boost confidence in significance based on neighboring SNPs also with significance in the top 1,000. We found 87 such regions with multiple significant SNPs composed of 344 SNPs in total, the remainder of which we excluded as spurious signal (Table 1). The most significant association was the major histocompatibility complex (MHC) with 110 neighboring SNPs showing significance in the top 1,000, the most significant SNP rs3117426 having $P=8.62\times10^{-10}$. A total of 62 regions were supported by two SNPs, and 25 regions were supported by 3 or more SNPs, with 47 regions directly impacting genes while 40 did not.

TABLE 1

Genomic Regions with Multiple SNPs in the 1000 most Significant Associations

| Region Genomic Span | Gene | Distance | Distance From Exon | CountSNPs Top1000 | Best P | Best SNP | F_A | F_U |
|---|---|---|---|---|---|---|---|---|
| chr6: 27236785-32521295 | MHC, Many | 0 | 0 | 110 | 8.62E−10 | rs3117426 | 0.3268 | 0.1907 |
| chr8: 23746576-24681608 | ADAM28, ADAM7, ADAMDEC1, STC1 | 0 | 0 | 4 | 6.24E−6 | rs4872262 | 0.03911 | 0.01069 |
| chr6: 42776382-43502348 | CRIP3, CUL7, GNMT, KLC4, KLHDC3, MEA1, MRPL2, PARC, PEAS, PEX6, PPP2R5D, PRPH2, PTCRA, PTK7, RPL7L1, | 0 | 0 | 4 | 1.22E−5 | rs422717 | 0.2961 | 0.1982 |

TABLE 1-continued

Genomic Regions with Multiple SNPs in the 1000 most Significant Associations

| Region Genomic Span | Gene | Distance | Distance From Exon | CountSNPs Top1000 | Best P | Best SNP | F_A | F_U |
|---|---|---|---|---|---|---|---|---|
| | SLC22A7, SRF, TBCC, TNRC5, TTBK1, UNQ1934, ZNF318 | | | | | | | |
| chr14: 39744450-39909619 | BX248273 | 584047 | 584047 | 4 | 1.69E-5 | rs6571989 | 0.1927 | 0.115 |
| chr4: 189671181-189676119 | AK095968 | 0 | 18764 | 2 | 1.78E-5 | rs1606234 | 0.2961 | 0.4124 |
| chr16: 6120908-6137836 | A2BP1 | 0 | 110914 | 4 | 1.85E-5 | rs12924882 | 0.1313 | 0.06915 |
| chr2: 224812598-224841089 | FAM124B | 110570 | 110570 | 4 | 1.89E-5 | rs4264554 | 0.3184 | 0.4353 |
| chr2: 45599872-45895169 | PRKCE, SRBD1 | 0 | 0 | 7 | 2.12E-5 | rs17322265 | 0.3408 | 0.4576 |
| chr10: 73083830-73084583 | CDH23, KIAA1812 | 0 | 7287 | 2 | 2.45E-5 | rs7087554 | 0.5894 | 0.4729 |
| chr2: 74996818-75001224 | AK125960 | 7650 | 7650 | 2 | 3.25E-5 | rs3771781 | 0.3184 | 0.4319 |
| chr20: 55079605-55083403 | BMP7 | 95559 | 95559 | 2 | 4.44E-5 | rs6127923 | 0.2318 | 0.1498 |
| chr7: 4270929-4287047 | SDK1 | 0 | 0 | 5 | 4.70E-5 | rs895710 | 0.2905 | 0.4003 |
| chr20: 15025030-15074507 | C20orf133 | 0 | 50997 | 4 | 5.15E-5 | rs6043091 | 0.2151 | 0.1367 |
| chr8: 8804291-8808564 | MFHAS1 | 15750 | 15750 | 3 | 6.80E-5 | rs400404 | 0.3715 | 0.2726 |
| chr1: 158072814-158076453 | CR625159, RP11-190A12.4, SLAMF8 | 0 | 0 | 2 | 7.31E-5 | rs10494349 | 0.2067 | 0.1312 |
| chr18: 25213638-25220939 | CDH2 | 1202449 | 1202449 | 2 | 7.53E-5 | rs9950880 | 0.2821 | 0.1943 |
| chr3: 106535466-107174255 | ALCAM, CBLB, Nbla00127 | 0 | 0 | 5 | 8.57E-5 | rs13062596 | 0.4358 | 0.3328 |
| chr6: 85682448-85684185 | TBX18 | 151830 | 151830 | 2 | 9.07E-5 | rs9444253 | 0.05028 | 0.1187 |
| chr1: 20369369-20490791 | FLJ32784, UBXN10 | 0 | 0 | 7 | 9.09E-5 | rs7514144 | 0.2654 | 0.1808 |
| chr10: 27709830-27728115 | PTCHD3 | 0 | 0 | 7 | 9.77E-5 | rs506659 | 0.4022 | 0.3026 |
| chr12: 123259607-123275011 | FAM101A | 64652 | 64652 | 4 | 1.01E-4 | rs7972182 | 0.3855 | 0.2874 |
| chr13: 68136436-68138181 | BC042673 | 195237 | 195237 | 2 | 1.09E-4 | rs287355 | 0.2219 | 0.3213 |
| chr16: 69996550-70004357 | CALB2 | 14714 | 14714 | 2 | 1.09E-4 | rs12102284 | 0.1676 | 0.1015 |
| chr11: 25128661-25130289 | LUZP2 | 67899 | 67899 | 2 | 1.10E-4 | rs11028465 | 0.3352 | 0.2426 |
| chr12: 49729991-49731928 | DKFZp586A011, LETMD1 | 0 | 214 | 2 | 1.22E-4 | rs4768959 | 0.1397 | 0.08033 |
| chr4: 25702025-25756263 | LOC389203 | 161493 | 161493 | 5 | 1.34E-4 | rs2048507 | 0.257 | 0.1755 |
| chr7: 13858986-13866233 | ETV1 | 31148 | 31148 | 4 | 1.35E-4 | rs12532319 | 0.09218 | 0.04617 |
| chr1: 59987116-59993733 | FLJ10986, RP11-242B9.1 | 0 | 2458 | 2 | 1.52E-4 | rs11207520 | 0.3994 | 0.3026 |
| chr6: 12070732-12073684 | HIVEP1 | 47026 | 47026 | 2 | 1.54E-4 | rs12193434 | 0.09777 | 0.05034 |
| chr19: 40814281-40815243 | MGC10433 | 0 | 134 | 2 | 1.55E-4 | rs2285415 | 0.352 | 0.4559 |
| chr6: 139472753-139477571 | HECA | 20371 | 20371 | 2 | 1.56E-4 | rs17304375 | 0.2318 | 0.1549 |
| chr12: 80435676-80444630 | PPFIA2 | 0 | 59900 | 2 | 1.63E-4 | rs2400955 | 0.4134 | 0.3159 |
| chr12: 69717561-69720071 | TSPAN8 | 85073 | 85073 | 2 | 1.63E-4 | rs6581986 | 0.2905 | 0.2053 |
| chr11: 102069786-102079454 | MMP27 | 0 | 0 | 2 | 1.69E-4 | rs17099394 | 0.1229 | 0.0687 |
| chr3: 188168001-188168026 | ST6GAL1 | 0 | 3593 | 2 | 1.71E-4 | rs12495023 | 0.2765 | 0.1934 |
| chr16: 71592439-71594134 | ATBF1 | 0 | 40845 | 2 | 1.80E-4 | rs8056528 | 0.3687 | 0.2754 |
| chr8: 124729628-124734756 | C8ORFK36 | 0 | 0 | 4 | 2.05E-4 | rs4871402 | 0.06425 | 0.1325 |
| chr22: 42908147-43159207 | KIAA1644, PARVG | 0 | 0 | 8 | 2.27E-4 | rs80303 | 0.3994 | 0.5013 |

TABLE 1-continued

Genomic Regions with Multiple SNPs in the 1000 most Significant Associations

| Region Genomic Span | Gene | Distance | Distance From Exon | CountSNPs Top1000 | Best P | Best SNP | F_A | F_U |
|---|---|---|---|---|---|---|---|---|
| chr20: 44622587-44638545 | NADC3, SLC13A3 | 0 | 0 | 5 | 2.49E-4 | rs393990 | 0.09218 | 0.1664 |
| chr1: 9459963-9467504 | SLC25A33 | 54611 | 54611 | 2 | 2.57E-4 | rs10746490 | 0.1453 | 0.2292 |
| chr3: 7364204-7369287 | GRM7 | 0 | 40865 | 4 | 2.96E-4 | rs12491592 | 0.1536 | 0.0939 |
| chr11: 46472478-46855347 | ARHGAP1, CKAP5, CR612190, F2, LRP4, MEGF7, ZNF408, coagulation factor II | 0 | 0 | 4 | 3.19E-4 | rs2306029 | 0.3603 | 0.4593 |
| chr2: 181999958-182002374 | AK125001 | 27433 | 27433 | 2 | 3.22E-4 | rs16867404 | 0.09497 | 0.05008 |
| chr7: 121184414-121193891 | PTPRZ1 | 106504 | 106504 | 2 | 3.24E-4 | rs1196493 | 0.5251 | 0.4266 |
| chr3: 8378739-8381919 | BC020876 | 0 | 129448 | 2 | 3.51E-4 | rs359030 | 0.1648 | 0.1033 |
| chr6: 25570803-25574868 | LRRC16 | 0 | 0 | 2 | 3.61E-4 | rs4320355 | 0.3799 | 0.2898 |
| chr4: 131889955-131893245 | BC041448 | 793982 | 793982 | 2 | 3.68E-4 | rs2125639 | 0.2905 | 0.2094 |
| chr15: 58159939-58162165 | FOXB1 | 74505 | 74505 | 2 | 3.71E-4 | rs7168491 | 0.1648 | 0.1035 |
| chr6: 153354039-153355207 | MTRF1L | 0 | 0 | 2 | 3.81E-4 | rs9322400 | 0.4469 | 0.3526 |
| chr5: 172969660-172992688 | FAM44B | 0 | 0 | 4 | 3.83E-4 | rs258873 | 0.2849 | 0.3798 |
| chr6: 55433518-55442340 | HMGCLL1 | 0 | 21202 | 2 | 3.86E-4 | rs9382494 | 0.2179 | 0.3078 |
| chr9: 15192417-15195014 | C9orf52 | 0 | 0 | 2 | 3.87E-4 | rs693196 | 0.3603 | 0.2723 |
| chr4: 20207250-20210955 | SLIT2 | 0 | 0 | 2 | 4.29E-4 | rs573118 | 0.243 | 0.169 |
| chr3: 284363-285747 | CHL1 | 0 | 19083 | 2 | 4.31E-4 | rs17273893 | 0.148 | 0.09081 |
| chr11: 45198534-45198959 | PRDM11 | 0 | 650 | 2 | 4.36E-4 | rs12417962 | 0.06983 | 0.1351 |
| chr3: 138891290-138892064 | SOX14 | 74205 | 74205 | 2 | 4.37E-4 | rs12637203 | 0.1844 | 0.12 |
| chr8: 121001793-121010709 | DEPDC6 | 0 | 0 | 2 | 4.41E-4 | rs869340 | 0.324 | 0.2402 |
| chr18: 74518781-74526115 | SALL3 | 315148 | 315148 | 2 | 4.72E-4 | rs2931060 | 0.1257 | 0.07381 |
| chr4: 143965929-143971867 | INPP4B | 0 | 14945 | 2 | 4.81E-4 | rs10000770 | 0.1788 | 0.1158 |
| chr3: 115619659-115623404 | ZBTB20 | 0 | 29017 | 2 | 5.19E-4 | rs2718419 | 0.2598 | 0.1844 |
| chr2: 65518304-65520560 | FLJ16124 | 0 | 784 | 2 | 5.20E-4 | rs1194849 | 0.3659 | 0.4614 |
| chr5: 68236398-68245085 | AK128486 | 55041 | 55041 | 2 | 5.27E-4 | rs7718291 | 0.1313 | 0.2081 |
| chr21: 27713547-27722878 | BC043580 | 0 | 19690 | 2 | 5.51E-4 | rs469709 | 0.1704 | 0.1095 |
| chr3: 5866648-5866856 | EDEM1 | 630006 | 630006 | 2 | 5.91E-4 | rs2572690 | 0.1145 | 0.06602 |
| chr16: 7470020-7474240 | A2BP1 | 0 | 33910 | 2 | 5.93E-4 | rs2191388 | 0.2709 | 0.1948 |
| chr6: 88936647-88941540 | CNR1 | 4366 | 4366 | 2 | 6.35E-4 | rs9344757 | 0.2179 | 0.3041 |
| chr4: 32018838-32029980 | PCDH7 | 1265004 | 1265004 | 3 | 6.41E-4 | rs2130904 | 0.2458 | 0.3343 |
| chr1: 202125395-202130221 | SNRPE | 18492 | 18492 | 2 | 6.48E-4 | rs12145634 | 0.1369 | 0.08346 |
| chr7: 38733082-38736264 | HVPS41, VPS41 | 0 | 0 | 2 | 6.67E-4 | rs10255854 | 0.2179 | 0.3038 |
| chr11: 120260865-120269428 | GRIK4 | 0 | 5023 | 2 | 6.67E-4 | rs12577638 | 0.2011 | 0.1356 |
| chr11: 91278373-91283755 | FAT3 | 444245 | 444245 | 2 | 6.97E-4 | rs10501763 | 0.03911 | 0.09207 |
| chr16: 20151678-20152281 | GP2 | 77031 | 77031 | 2 | 7.14E-4 | rs9921767 | 0.0419 | 0.09572 |
| chr1: 221871750-221882793 | CAPN2 | 84031 | 84031 | 3 | 7.29E-4 | rs3856154 | 0.4134 | 0.3254 |
| chr10: 130929688-130931369 | MGMT | 224087 | 224087 | 2 | 7.33E-4 | rs538186 | 0.05307 | 0.1104 |

TABLE 1-continued

Genomic Regions with Multiple SNPs in the 1000 most Significant Associations

| Region Genomic Span | Gene | Distance | Distance From Exon | CountSNPs Top1000 | Best P | Best SNP | F_A | F_U |
|---|---|---|---|---|---|---|---|---|
| chr5: 170727300-170734557 | NPM1 | 12168 | 12168 | 2 | 7.52E-4 | rs7707008 | 0.1173 | 0.1894 |
| chr10: 63071553-63080172 | C10orf107 | 12553 | 12553 | 2 | 7.69E-4 | rs10994852 | 0.1061 | 0.06051 |
| chr21: 31427707-31432285 | TIAM1 | 0 | 0 | 2 | 7.93E-4 | rs2833297 | 0.2095 | 0.1435 |
| chr4: 42434168-42438752 | ATP8A1 | 80521 | 80521 | 2 | 8.09E-4 | rs6812482 | 0.2709 | 0.1965 |
| chr6: 161106705-161109328 | PLG | 12377 | 12377 | 2 | 8.78E-4 | rs9295131 | 0.2151 | 0.2986 |
| chr17: 12323188-12325534 | AX747308, BC122562 | 68477 | 68477 | 2 | 9.02E-4 | rs8069430 | 0.2584 | 0.186 |
| chr17: 50125991-50127579 | TOM1L1, tom1-like | 205624 | 205624 | 2 | 9.20E-4 | rs6504930 | 0.03371 | 0.08325 |
| chr16: 77330083-77334376 | WWOX | 0 | 305933 | 2 | 9.21E-4 | rs1364290 | 0.1844 | 0.1231 |
| chr11: 5493737-5511794 | HBG2, UBQLNL | 0 | 0 | 4 | 9.28E-4 | rs2047456 | 0.3436 | 0.2624 |
| chr3: 70644812-70648510 | LOC401072 | 96929 | 96929 | 2 | 9.91E-4 | rs17790790 | 0.5196 | 0.4293 |
| chr3: 1292289-1302261 | CNTN6 | 0 | 0 | 2 | 1.06E-3 | rs6799262 | 0.3571 | 0.2733 |
| chr3: 64977356-64985877 | BC040632 | 5173 | 5173 | 2 | 1.15E-3 | rs1517927 | 0.2318 | 0.1643 |
| chr5: 14818187-14825245 | ANKH | 0 | 0 | 2 | 1.15E-3 | rs17251715 | 0.3955 | 0.3113 |

Figure 1B:
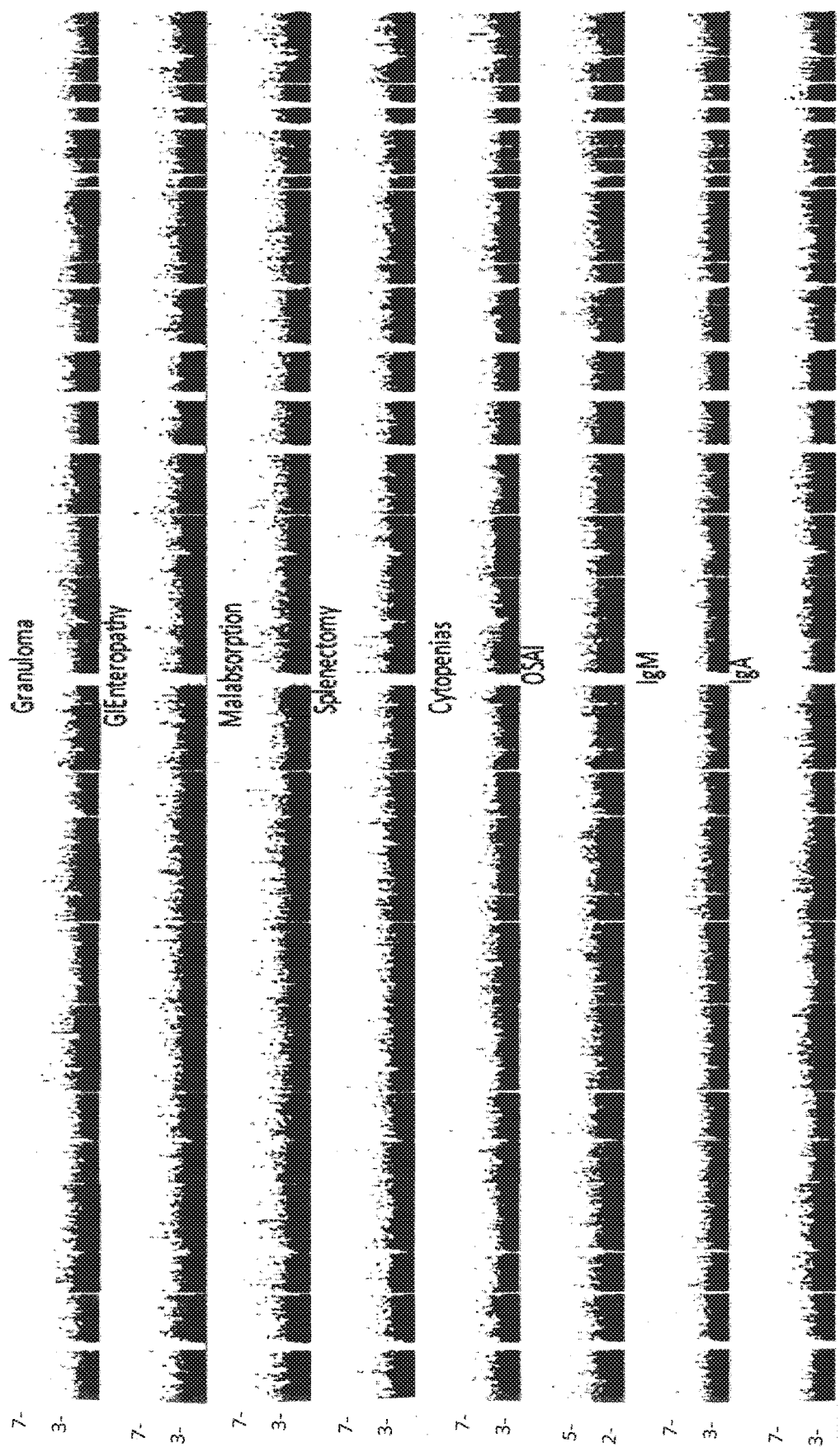

We next sought to replicate these SNPs and the direction of the difference in allele frequency, based on our replication cohort of 109 cases and 1114 controls with a genomic inflation factor of 1.04789 (FIG. 1B). Four SNPs displayed frequency in the same direction as discovery. There were three additional regions with directly affected genes: the MHC, UBXN10, and SDK1 (Table 2); others did not overlap genes directly.

TABLE 2

Most Significant Associated Regions Based on Genotype Association

| Region Genomic Span | Gene | Count SNPs Top 1000 | Distance From Exon | P | SNP | A1 | F_A | F_U | P Replication | SNP Replication | F_A Replication | F_U Replication |
|---|---|---|---|---|---|---|---|---|---|---|---|---|
| chr6: 27236785-32521295 | MHC | 110 | 0 | 8.62E-10 | rs3117426 | T | 0.3268 | 0.1907 | 0.0004 | rs2156875 | 0.5734 | 0.4475 |
| chr8: 23746576-24681608 | ADAM28, ADAM7, ADAMDEC1, STC1 | 4 | 0 | 6.24E-6 | rs4872262 | A | 0.0391 | 0.0107 | 0.0314 | rs4872262 | 0.0321 | 0.0135 |
| chr7: 4270929-4287047 | SDK1 | 5 | 0 | 4.70E-5 | rs895710 | T | 0.2905 | 0.4003 | 0.0235 | rs4720301 | 0.3991 | 0.4793 |
| chr1: 20369369-20490791 | FLJ32784, UBXN10 | 7 | 0 | 9.09E-5 | rs7514144 | C | 0.2654 | 0.1808 | 2.25E-8 | rs6426636 | 0.4679 | 0.2857 |
| chr1: 59987116-59993733 | FGGY | 2 | 2458 | 1.52E-4 | rs11207520 | G | 0.3994 | 0.3026 | 0.0015 | rs11207520 | 0.2569 | 0.1706 |
| chr2: 65518304-65520560 | FLJ16124 | 2 | 784 | 5.20E-4 | rs1194849 | G | 0.3659 | 0.4614 | 0.0119 | rs1876518 | 0.3853 | 0.4744 |

Bold underline: Known immunological function genes, A1: allele 1 which is the minor allele, F_A: Frequency of allele 1 in affected individuals, F_U: Frequency of allele 1 in unaffected individuals.
See additional detail inTable 11.

significance (P<0.05) and allele frequency in the same direction as the discovery cohort, including rs11207520, rs1194849, rs17790790, and rs4872262. The associated chromosomal region demonstrating replication that impacted characterized genes was 8p21.2, harboring ADAM28, ADAM7, ADAMDEC1, and STC1. When all SNPs contributing to the discovery region were queried in replication rather than just the most significant SNP, 8 (four additional) SNPs displayed significance (P<0.05) and allele We had access to a large IBD cohort that had been genotyped previously[19]. Since this is also a heterogeneous immunological condition but without increased infectious susceptibility, it was considered that this group would be appropriate as a disease control group. Analysis of the 2,413 IBD cases and 6,197 controls revealed a number of signals in the IBD cohort that were distinct from both controls and the CVID cohort (including 19 CVID subjects who had been diagnosed with IBD). These included a signal in DEPDC6

(P<0.05) with allele frequency in the same direction as well as the MHC locus. In addition, TIAM1, SLAMF8, GRIK4, 6p21.1, PPFIA2, SLC25A33, A2BP1, and UBXN10 were also observed in the IBD cohort only (P<0.05). Importantly, however, the majority of associations in CVID identified in comparison to controls were not observed in the IBD cohort, suggesting that that they were not a general feature of an immunologic disease, but specific to the CVID phenotype. The non-overlapping loci between CVID and IBD included FLJ16124, ADAM28-ADAM7-ADAMDEC1-STC1, ANKH, FLJ109860-RP11-242B9.1, and WWOX, which are therefore more likely to lead to loss of B cell and antibody function.

Figure 2A:
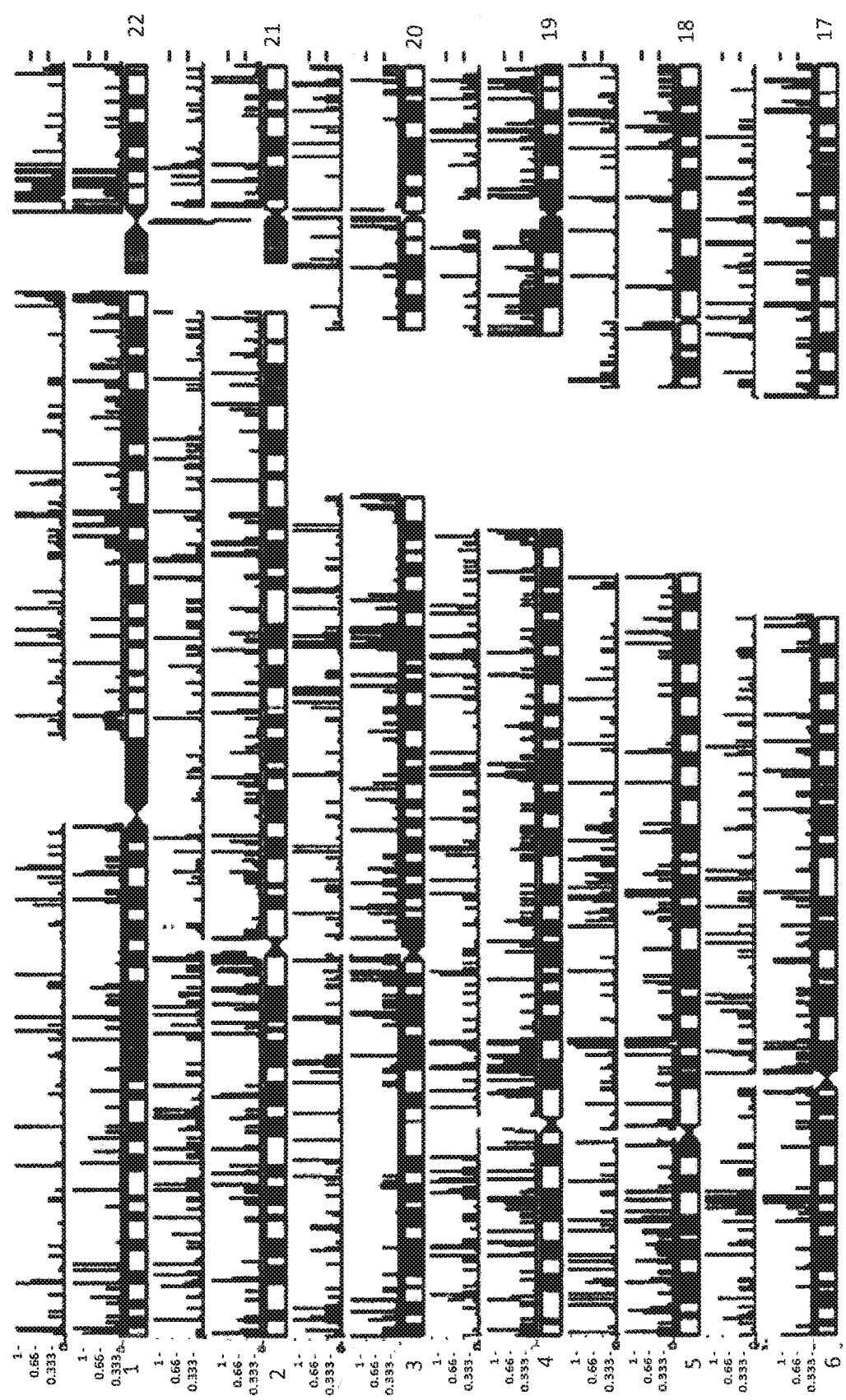
FIGS. 2A-2B. Frequency of CNV in cases (FIG. 2A) and controls (FIG. 2B). CNVs are called on a single sample basis with deletions and duplications in specific genomic regions based on the genotype and intensity signal of contiguous SNPs. These single sample CNV profiles are plotted as a SNP-based statistic to allow for SNP-based association testing. Lastly, neighboring SNPs with similar significance define a CNVR. Light grey indicates case deletion; Dark grey indicates case duplication; Black indicates control deletion; Medium grey indicates control duplication.
Figure 2B:
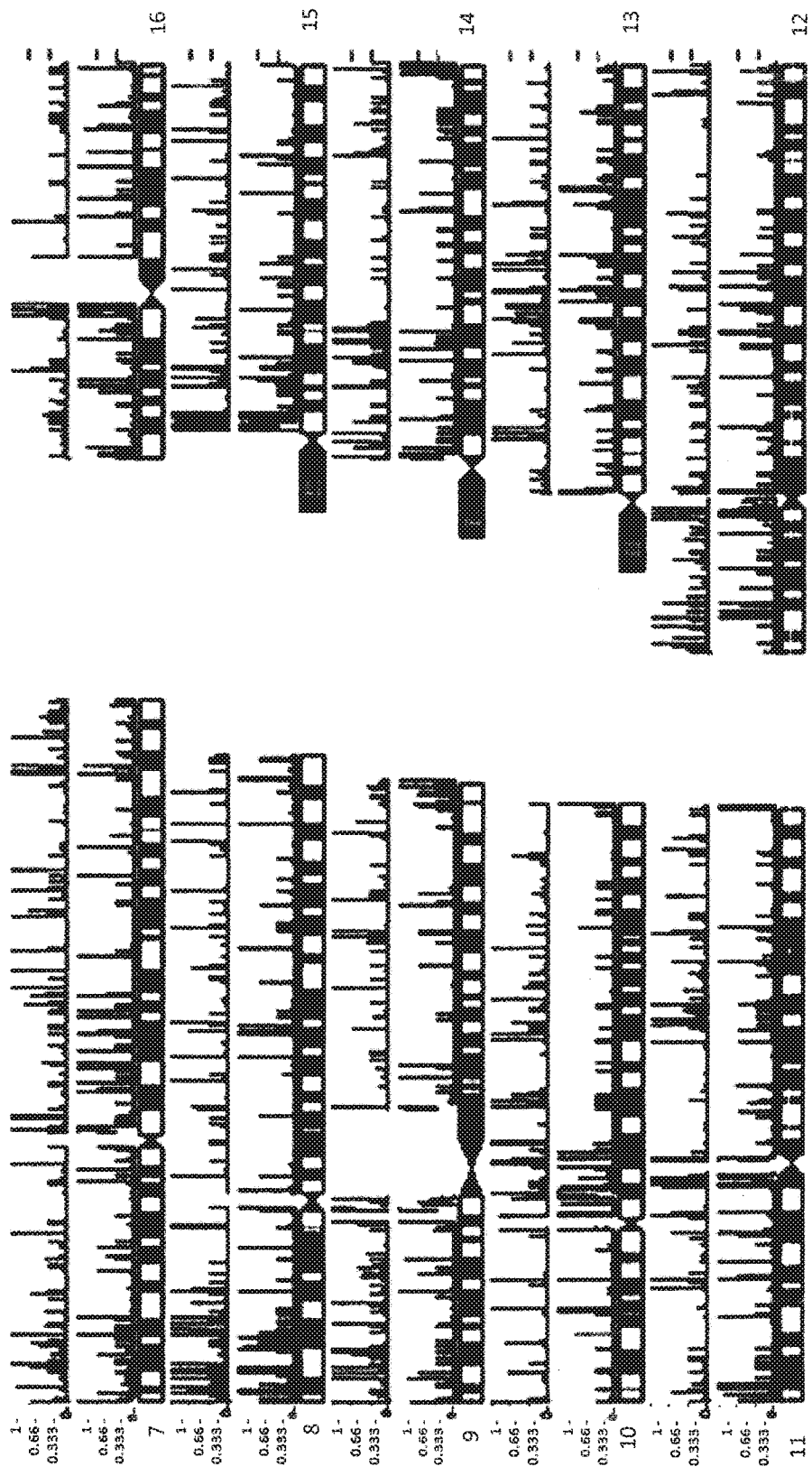
Figure 3:
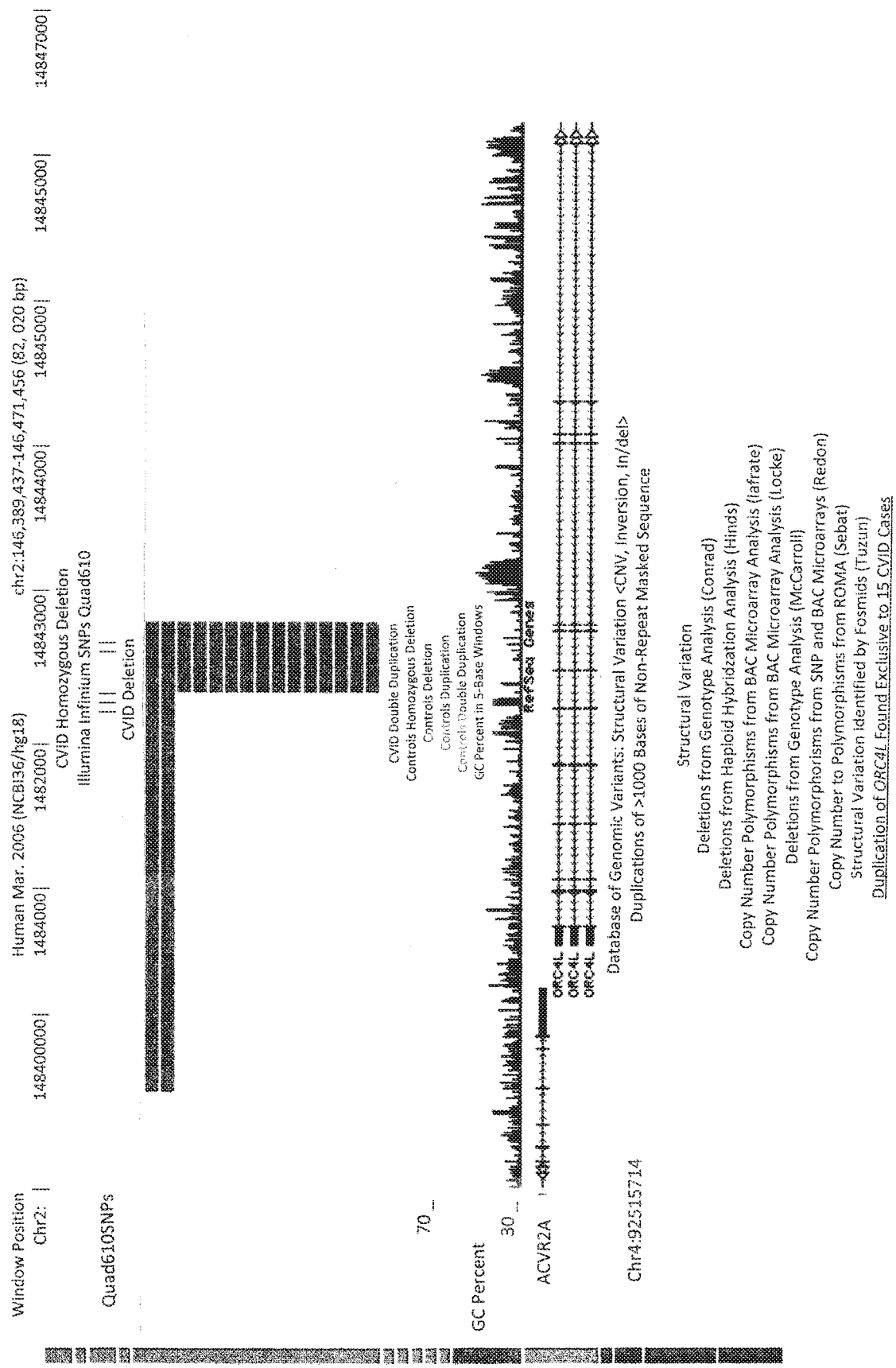
FIG. 3. Duplication of ORC4L Found Exclusive to 15 CVID Cases. Vertical lines indicate the SNP probe coverage. Rectangles delineate regions of copy number variation in individual cases. Three exons of ORC4L are shown duplicated in 15 cases and 0 controls. It is likely that the duplications could extend to a larger region of ORC4L based on coverage.
Figure 4A:
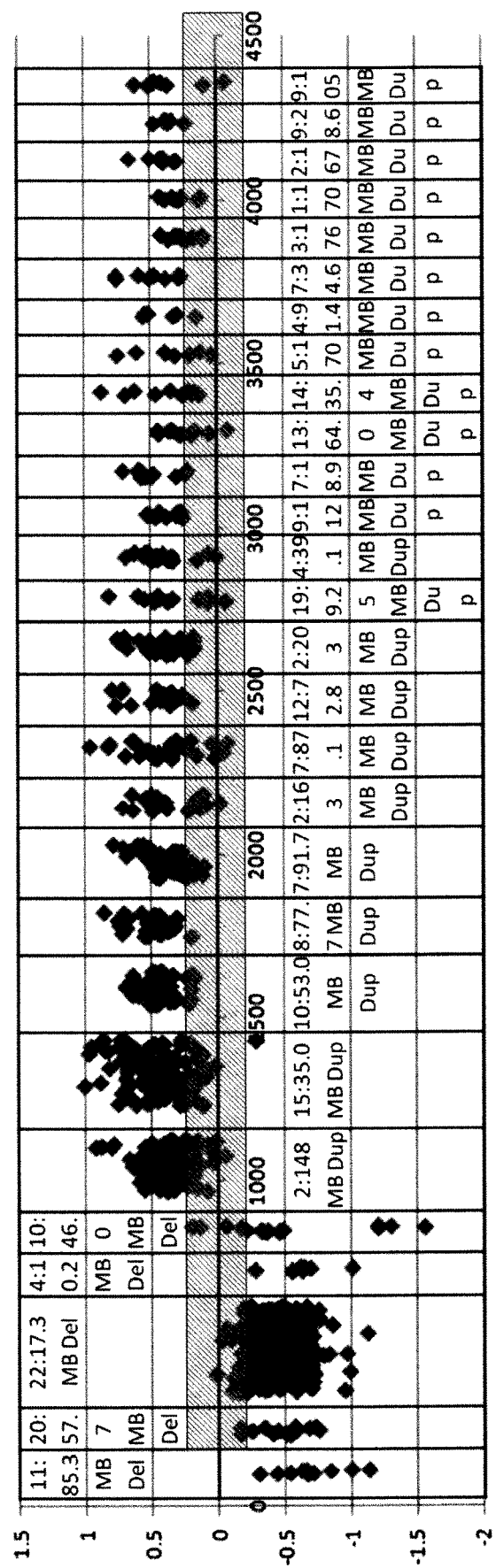
FIGS. 4A-4K. CNV Validation with Illumina Intensity Data Review and Independent Array Technology, Affymetrix 2.7M FIG. 5. The core diagnosis of CVID has many clinical progressions with varying frequency. The height and size of subphenotypes signify the frequency of the specific progression. Given significant SNP genotype associations for each CVID subphenotype progression vs. CVID patients without the progression, prediction can be made which may improve clinical outcome.
Figure 4B:
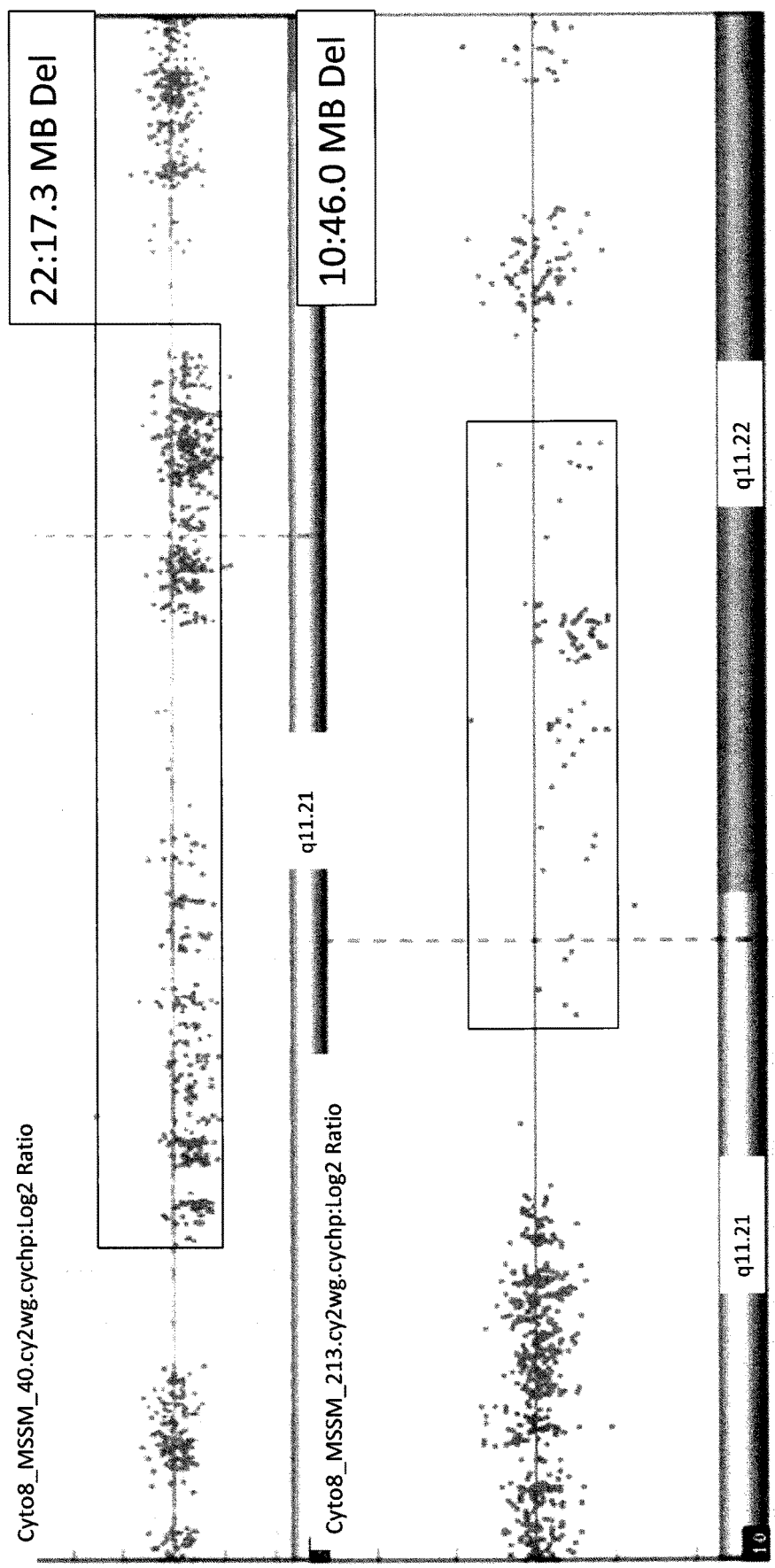
Figure 4C:
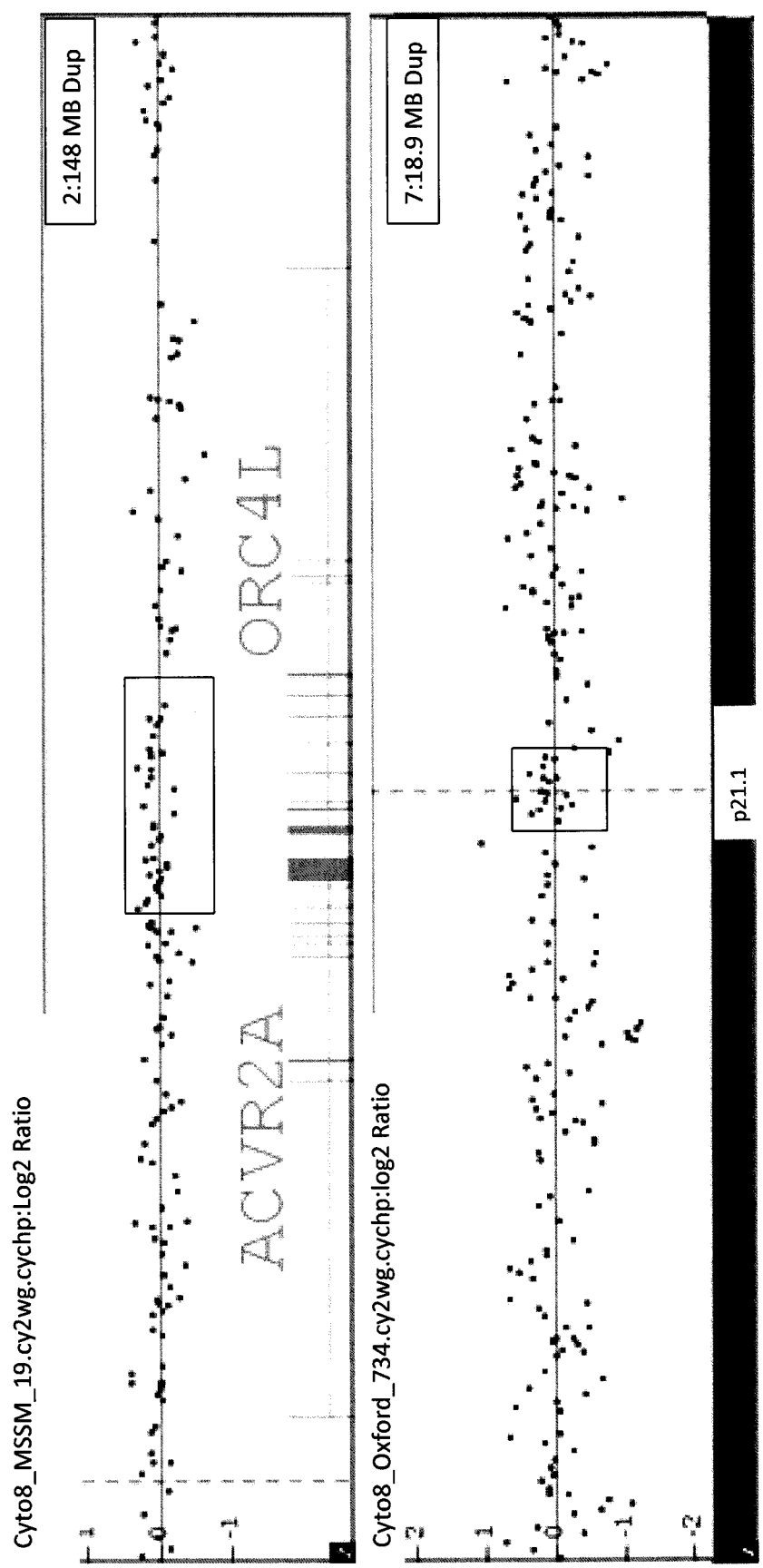
Figure 4D:
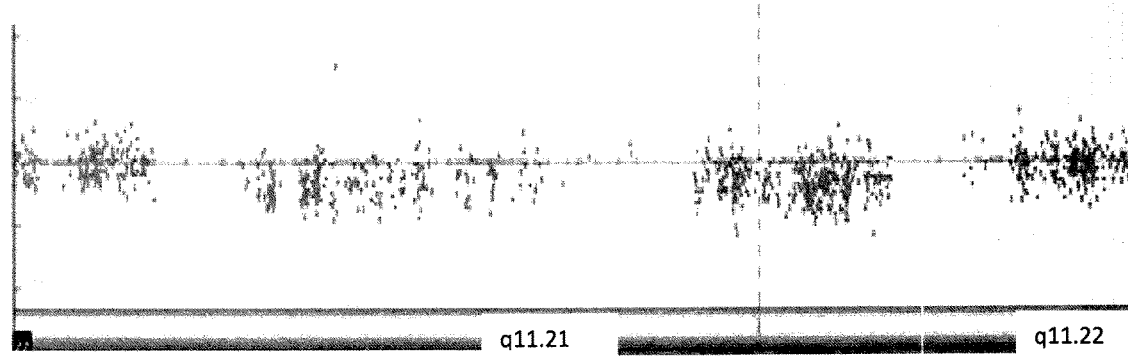
Figure 4D:
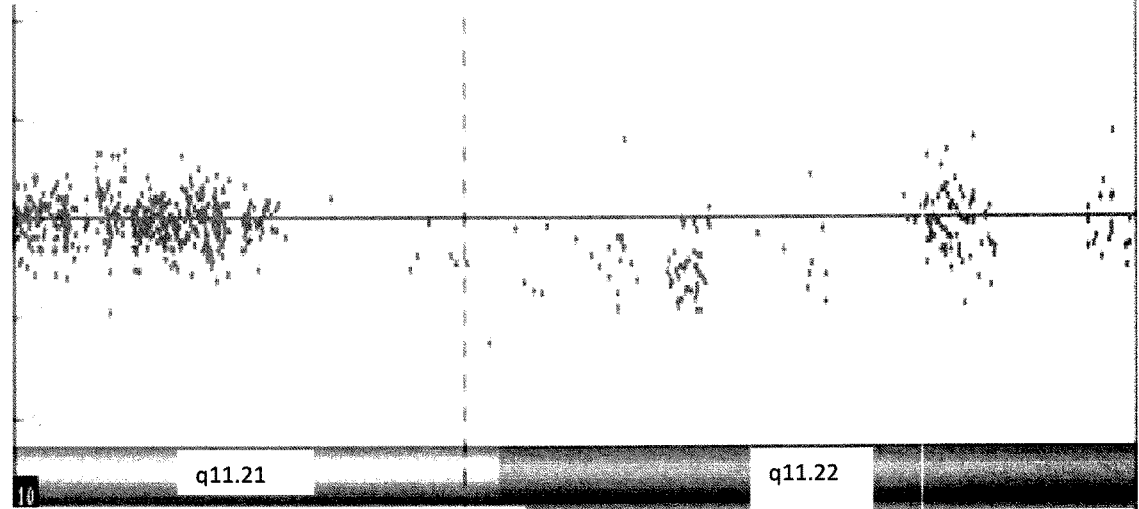
Figure 4D:
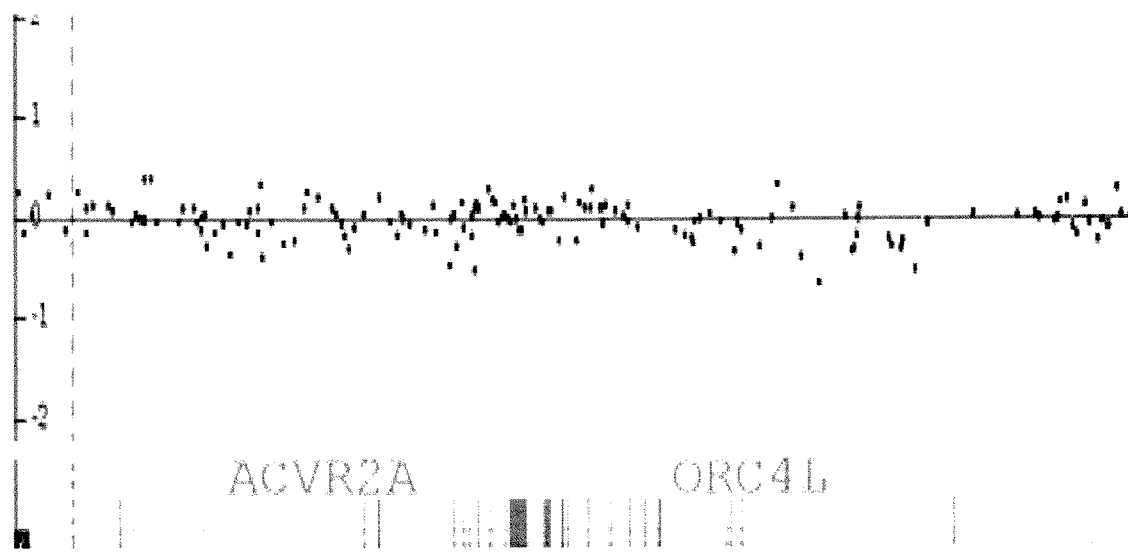
Figure 4E:
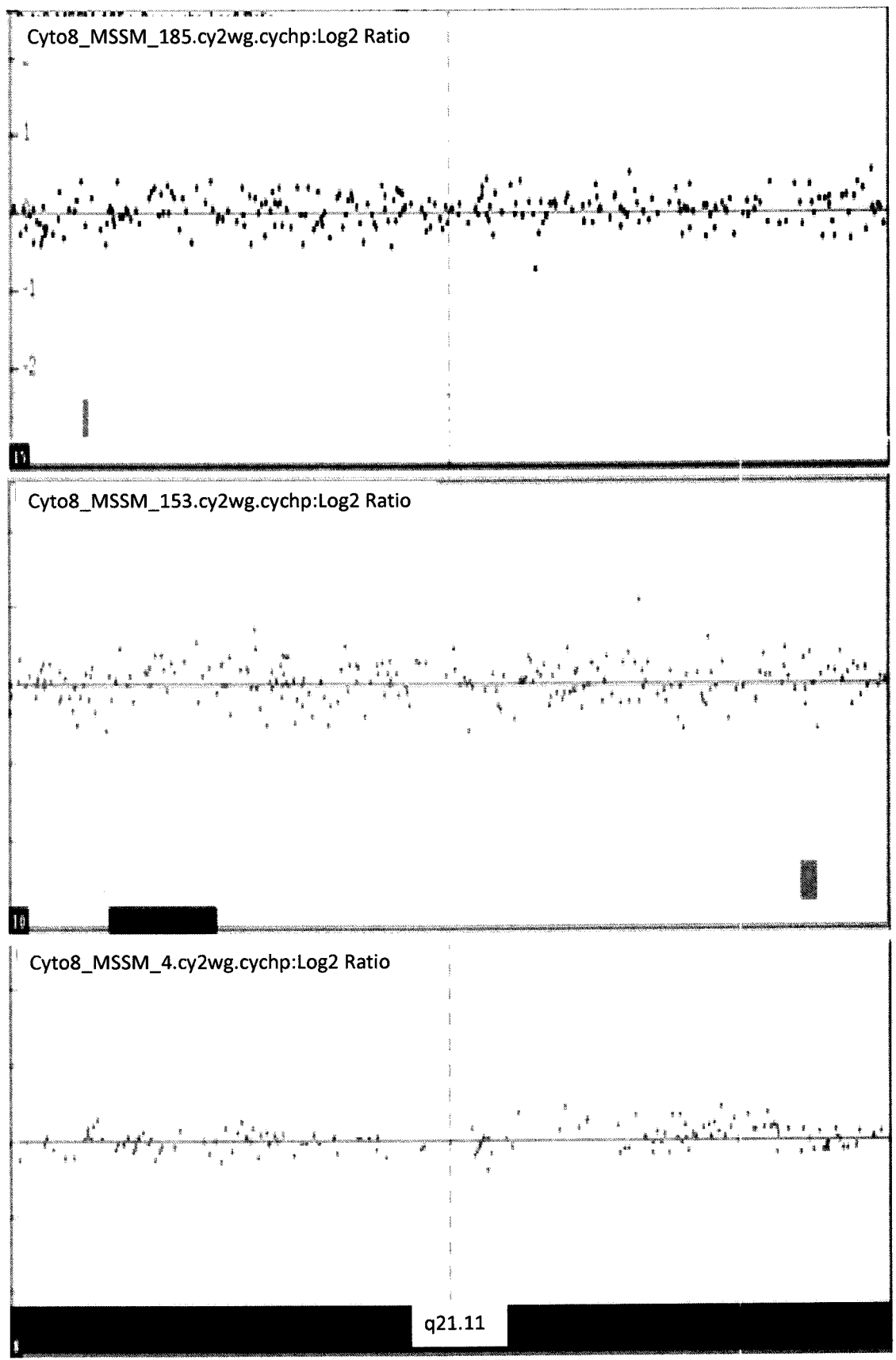
Figure 4F:
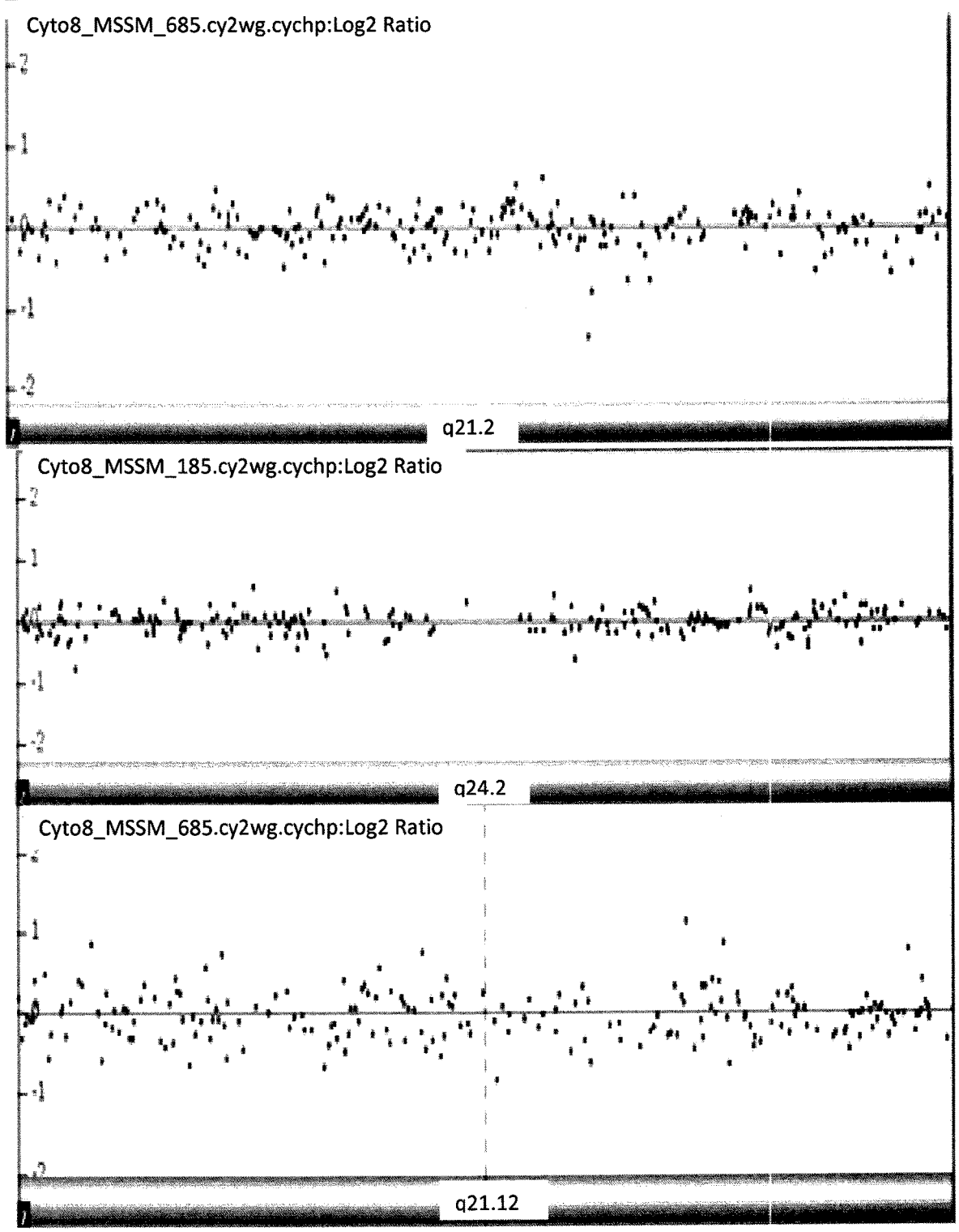
Figure 4G:
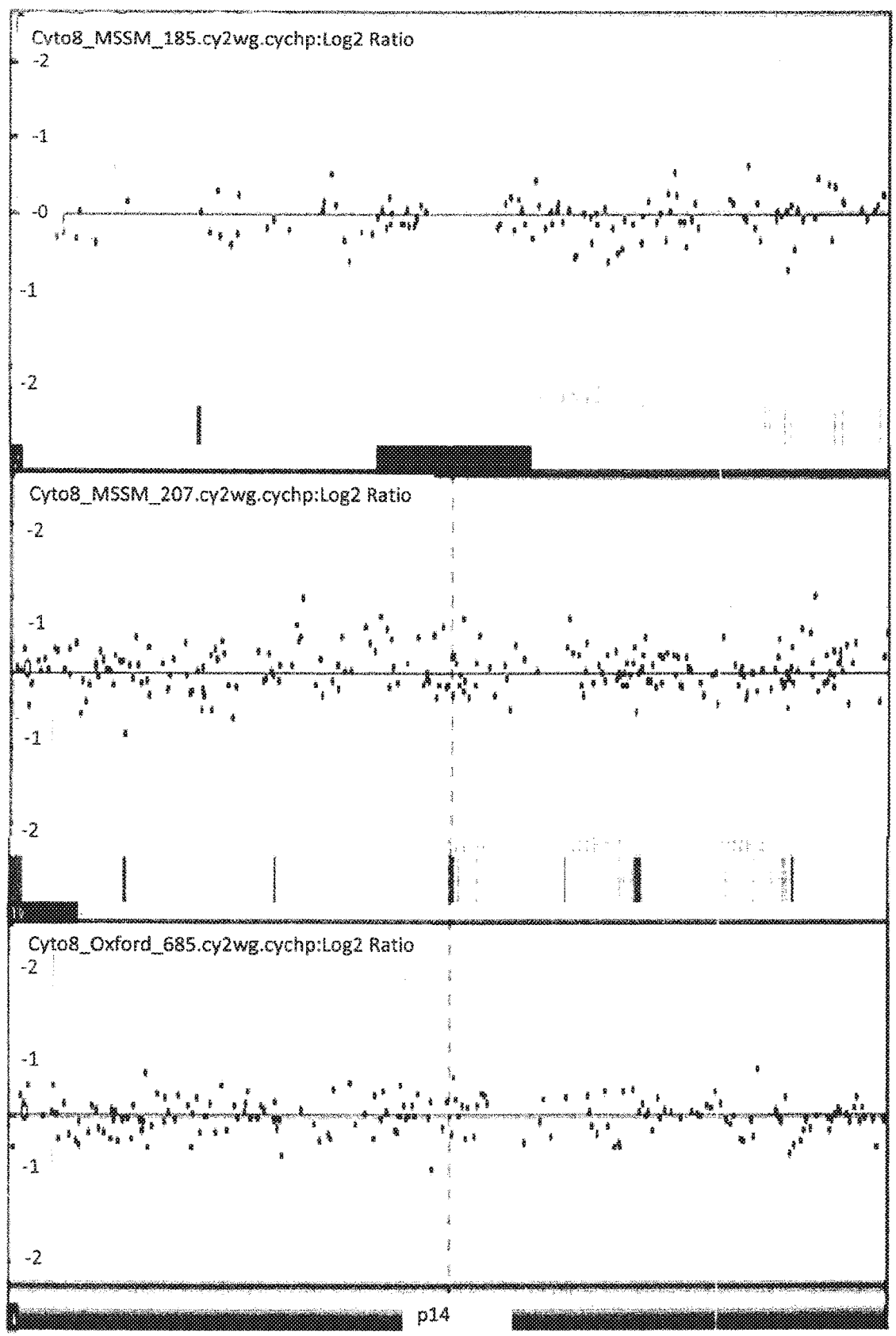
Figure 4H:
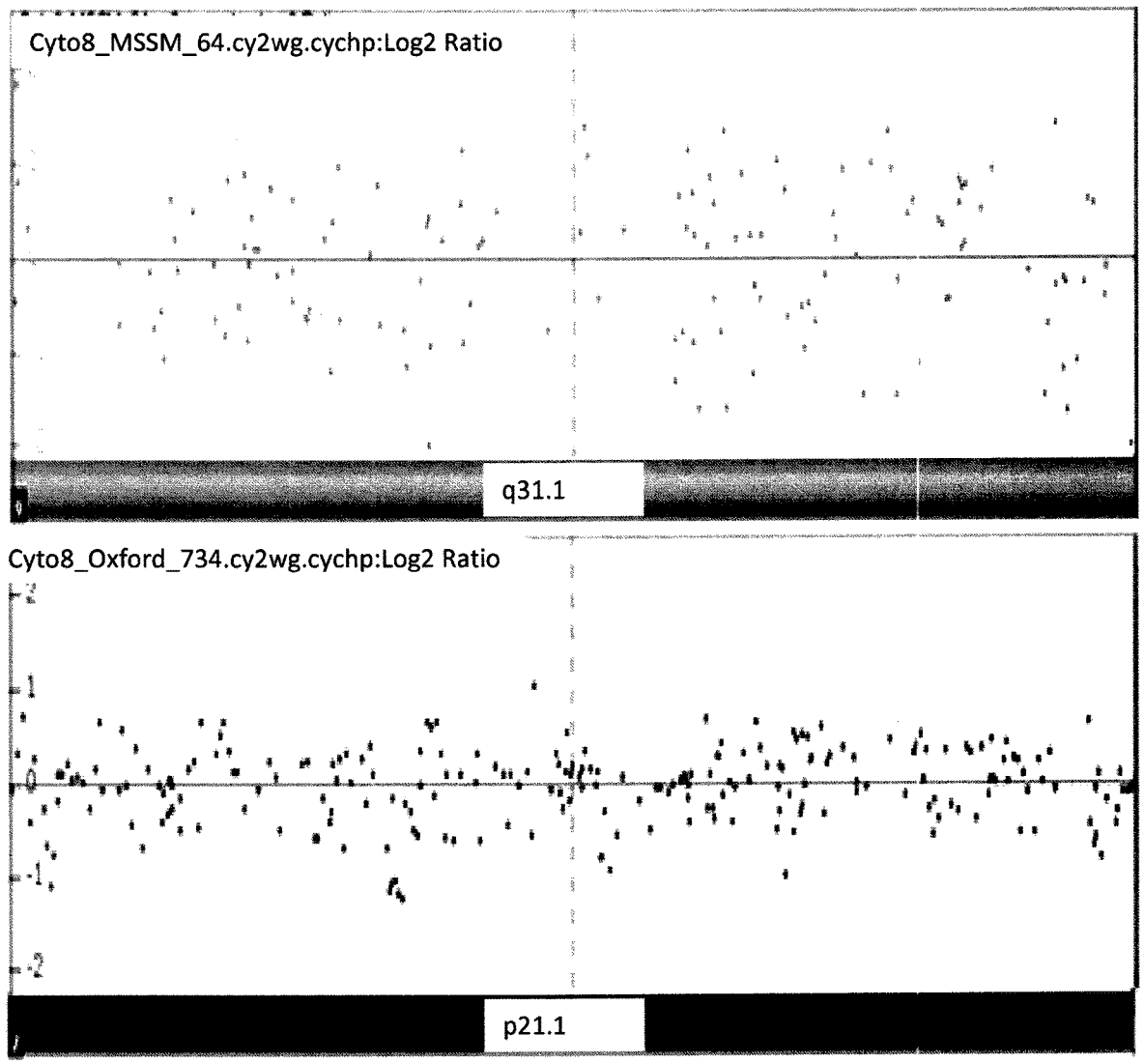
Figure 4I:
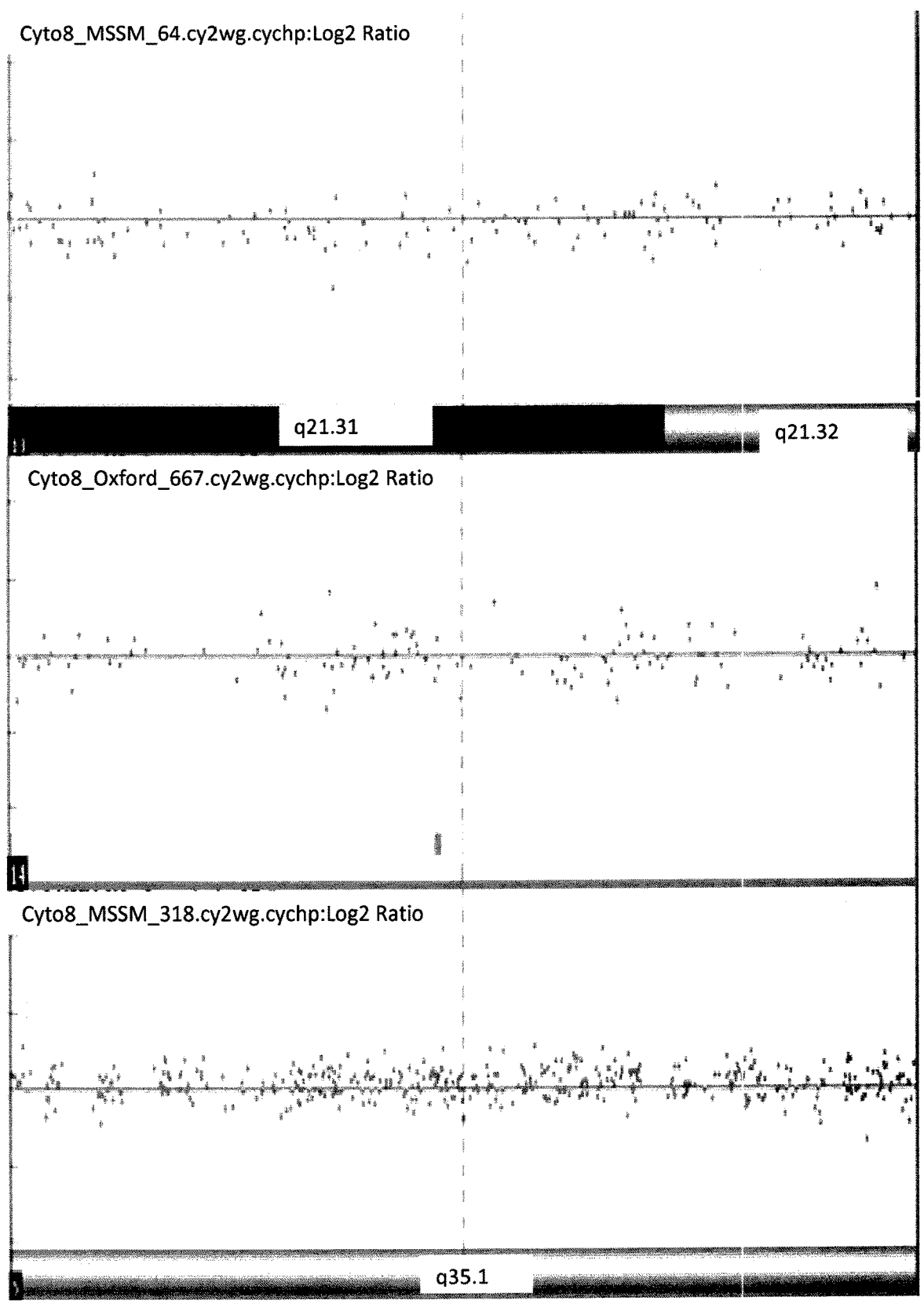
Figure 4J:
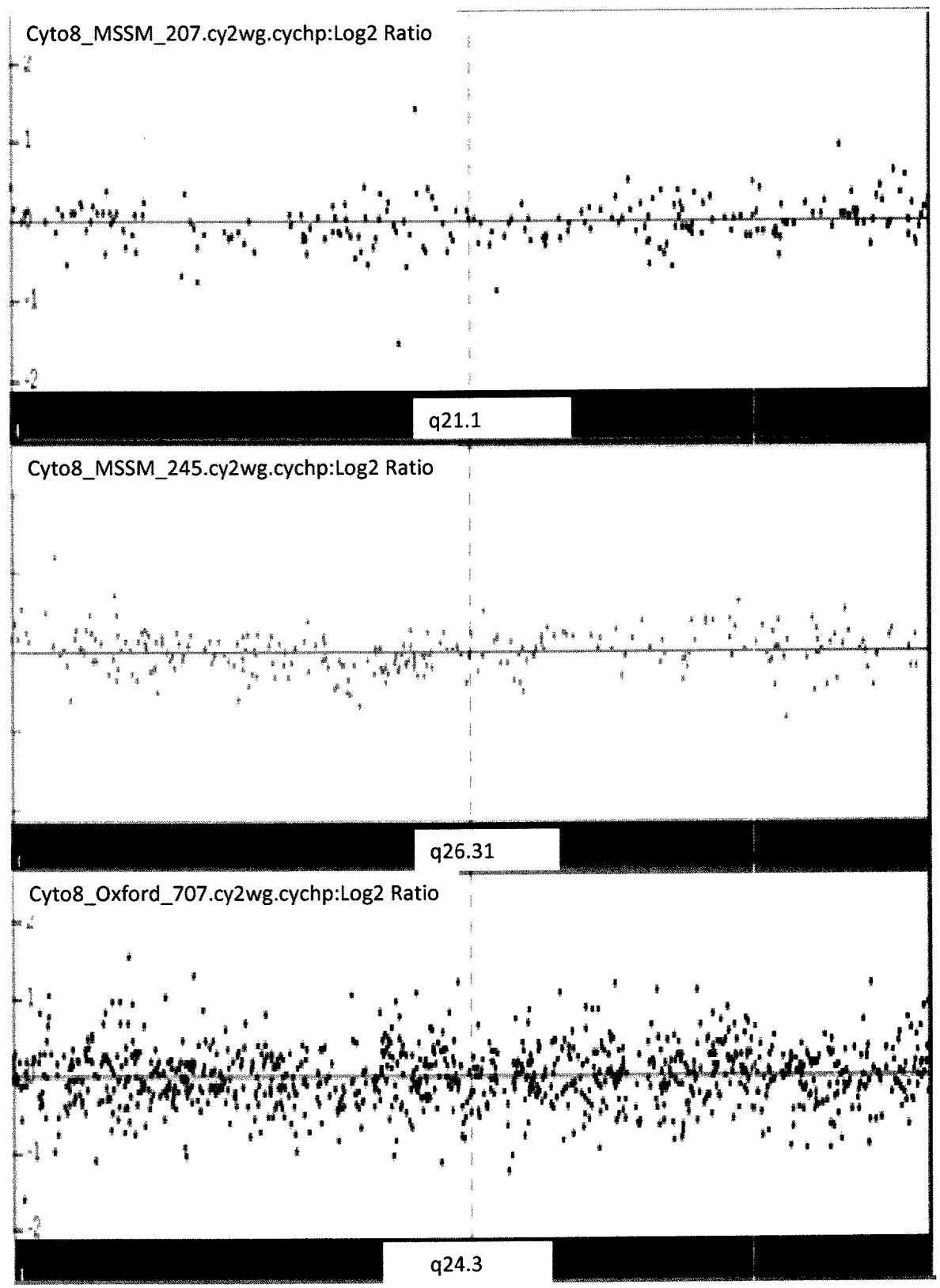
Figure 4K:
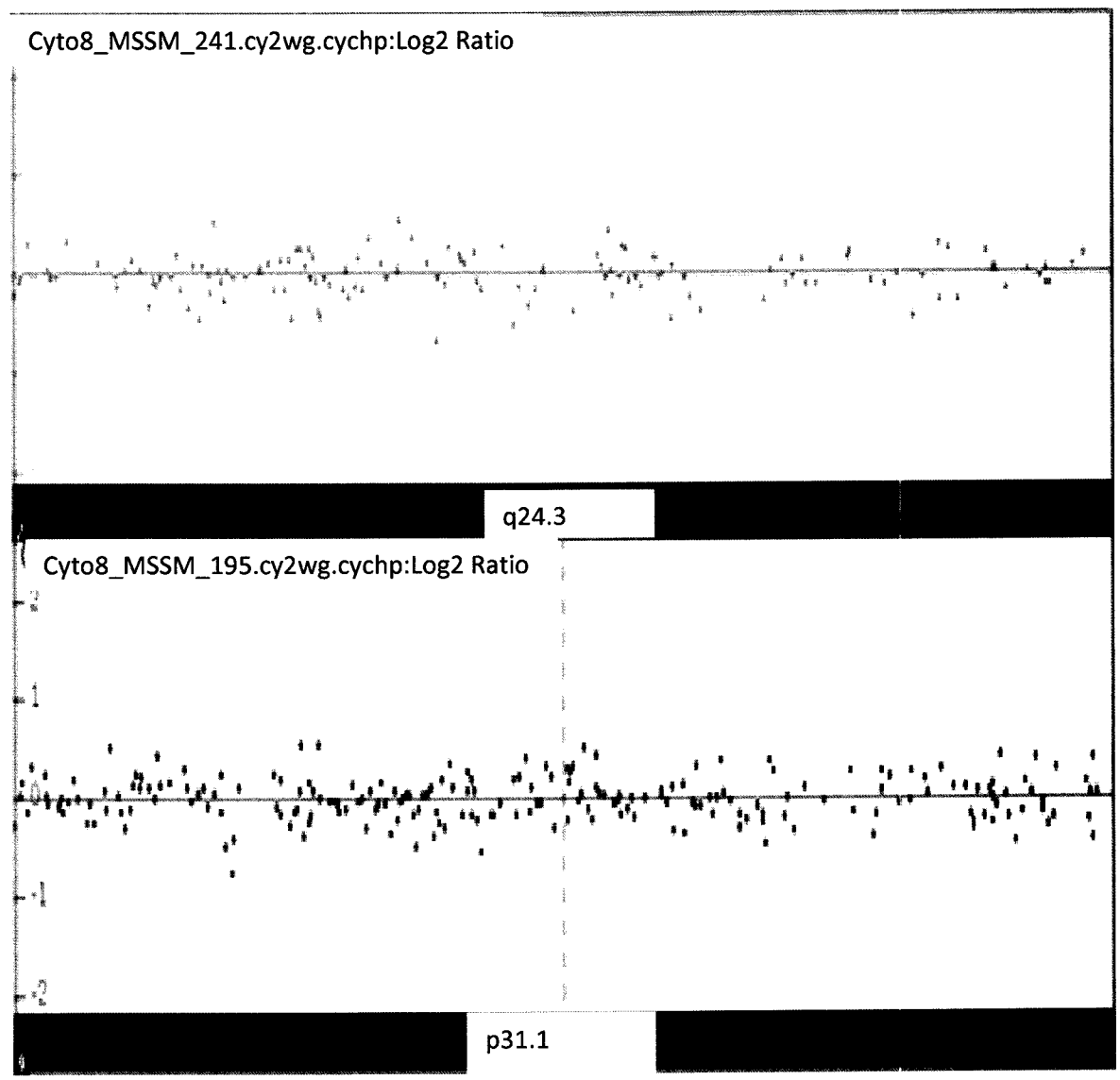

We next performed a CNV analysis, where rare (<1%) CNVs were called, using PennCNV[20] and SNP-based CNV frequency in cases and controls; these were compared for associations. We analyzed deletion and duplication CNV frequency of 311 cases and 2,766 controls (FIG. 2). To limit bias due to population stratification, the contribution of patients from the discovery Caucasian cluster defined in the genotype GWAS was required to establish confidence. We also monitored the contribution of each sample subgroup from the four different sample collection sites. We found 5 deletions and 11 duplications to be recurrent and significantly enriched in the patients as compared to controls (Table 3). In addition, a total of 15 regions were exclusive to CVID cases. Duplications of 2q23.1 associated with multiple exons of ORC4L were observed to be exclusive to 15 cases (P=8.66×10$^{-16}$) (FIG. 3). We also observed large CNVs with at least 10 SNPs exclusive to single CVID cases totaling 84 deletions and 98 duplications in CNVs. (Table 4). No significant overrepresentation was observed in the controls in this frequency range. Of clinical relevance, 2 patients were newly identified with deletion in the 22q11 region suggesting an alternative presentation of the well-characterized PIDD associated with this microdeletion. Of 5 deletions and 23 duplications significantly enriched in CVID, 4 deletions and 21 duplications significant in CVID were not significant in IBD. 10 regions of homozygous deletion were observed exclusively in CVID cases (Table 5). To further prioritize resulting significant loci for potential functional impact, we calculated distance of CNVs from exons to highlight loci impacting exons directly, a method applied previously[21]. We examined overall CNV burden in cases compared to controls for significant results, exonic CNVs, and large (100 kb) rare (<1%) CNVs and found deletions to be significantly enriched in cases when considering CNV observations on all loci genome wide (Table 6). All but 5 of the 182 CNVs exclusive to the CVID cohort were intraexonic. To assess the reliability of our CNV detection method, we reviewed the BAF (genotype) and LRR (intensity) values of our Illumina data and experimentally validated all the significant CNVRs using an independent method, the Affymetrix Cytogenetics Whole-Genome 2.7M Array which provides high resolution with 400,103 SNP and 2,387,595 CN probes (FIG. 4).

TABLE 3

Most Significant Associated Regions Based on CNV Association

A) Deletions

| CNVR Deletion | Count SNPs | Distance From Exon | P Deletion | Cases Del | Controls Del | Gene | MSSM | Oxford | USF | Combined |
|---|---|---|---|---|---|---|---|---|---|---|
| chr11: 85365857-85381622 | 5 | 0 | 0.01 | 2 | 0 | PICALM, PICALM variant protein | 0 | 2 | 0 | 2 |
| chr20: 57735790-57741780 | 6 | 5902 | 0.026 | 3 | 4 | PHACTR3 | 2 | 1 | 0 | 3 |
| chr22: 17396663-18417315 | 270 | 0 | 0.029 | 2 | 1 | ARVCF, COMT, TBX1, others | 2 | 0 | 0 | 2 |
| chr4: 10256682-10264316 | 4 | 2915 | 0.029 | 2 | 1 | CLNK | 0 | 1 | 1 | 2 |
| chr10: 46003146-46042543 | 8 | 0 | 0.029 | 2 | 1 | DKFZp566K0524, PTPN20A, PTPN20B | 2 | 0 | 0 | 2 |

B) Duplications

| CNVR Duplication | Count SNPs | Distance From Exon | P Dup | Cases Dup | Controls Dup | Gene | MSSM | Oxford | USF | Combined |
|---|---|---|---|---|---|---|---|---|---|---|
| chr2: 148396730-148433180 | 6 | 0 | 8.66E-16 | 15 | 0 | ACVR2A, ORC4L | 10 | 5 | 0 | 15 |
| chr15: 35053039-35063531 | 6 | 23146 | 5.72E-13 | 19 | 10 | MEIS2 | 17 | 2 | 0 | 19 |
| chr7: 91789778-91801963 | 4 | 0 | 1.20E-09 | 12 | 4 | ANKIB1 | 9 | 3 | 0 | 12 |
| chr2: 163316298-163316595 | 3 | 17100 | 1.00E-07 | 7 | 0 | KCNH7 | 6 | 1 | 0 | 7 |
| chr7: 87180702-87191931 | 4 | 202 | 7.41E-07 | 7 | 1 | RPIB9 | 5 | 2 | 0 | 7 |
| chr19: 9256584-9277749 | 4 | 0 | 0.001 | 3 | 0 | ZNF699 | 2 | 0 | 1 | 3 |
| chr4: 39190766-39201960 | 6 | 0 | 0.004 | 3 | 1 | UGDH | 1 | 2 | 0 | 3 |
| chr7: 18903915-18905725 | 4 | 23171 | 0.009 | 3 | 2 | HDAC9 | 1 | 2 | 0 | 3 |
| chr5: 170531269-170536993 | 4 | 374 | 0.01 | 2 | 0 | DKFZp666P032, RANBP17 | 1 | 1 | 0 | 2 |

TABLE 3-continued

Most Significant Associated Regions Based on CNV Association

| | | | | | | | | | | |
|---|---|---|---|---|---|---|---|---|---|---|
| chr7: 34685030-34686172 | 4 | 4517 | 0.01 | 2 | 0 | AAA1, NPRS1 | 1 | 1 | 0 | 2 |
| chr1: 170400944-170403742 | 4 | 26274 | 0.01 | 2 | 0 | DNM3 | 0 | 1 | 1 | 2 |

Additional detail in Table 12.

TABLE 4

Large Genic CNVs Impacting Single CVID Cases not Observed in Controls

| CNVR Del Singleton | Count SNPs | Distance From Exon | Gene |
|---|---|---|---|
| A) Deletions Impacting Immune Function Genes | | | |
| chr4: 86650109-87684765 | 209 | 0 | ARHGAP24, BC038746, MAPK10 |
| chr16: 75457204-76988778 | 78 | 0 | ADAMTS18, AK026469, BC035731, CLEC3A, KIAA1576, MON1B, WWOX |
| chr3: 74573112-74866049 | 66 | 0 | CNTN3 |
| chr19: 56625454-56761712 | 64 | 0 | LOC729767, SIGLEC12, SIGLEC6, SIGLEC8 |
| chr4: 103671292-104700248 | 51 | 0 | AK093356, BDH2, CENPE, CENPE variant protein, CR604221, LOC133308, MANBA, NFKB1, NHEDC1, UBE2D3, UNQ6308, ZCD2 |
| chr14: 43997374-46152755 | 45 | 0 | AX748292, BC038722, C14orf106, C14orf155, C14orf28, FANCM, FKBP3, KIAA0423, KLHL28, PRPF39 |
| chr6: 29844580-30045812 | 44 | 0 | AK097625, BC035647, **HLA-A,HLA-A*0226,HLA-G,HLA-G2.2**, LOC554223, LOC642032, NR_001317, NR_001318, NR_002139 |
| chr2: 86695685-87945980 | 40 | 0 | ANAPC1, BC066991, CD8A, CD8B, DQ576041, LOC285074, MGC4677, PLGLB1, PLGLB2, RGPD1, RGPD2, RMND5A, RNF103 |
| chr6: 22380732-22525808 | 40 | 0 | PRL |
| chr6: 31465923-33432505 | 34 | 0 | AF075059, AGER, AGPAT1, AIF1, AK057104, AL050203, APOM, ATP6V1G2, B3GALT4, BAT1, BAT2, BAT3, BAT4, BAT5, BF, BRD2, BTNL2, C2, C4A, C4A variant protein, C6orf10, C6orf21, C6orf25, C6orf26, C6orf27, C6orf31, C6orf47, C6orf48, CFB, CLIC1, COL11A2, CREBL1, CS266662, CSNK2B, CYP21A2, DAXX, DDAH2, DKFZp313H139, DKFZp547I194, DKFZp779M0311, DOM3Z, EGFL8, EHMT2, FKBPL, G18.1a, G6E, G6e, G7c, G8, GPSM3, HCP5, HLA-DMA,HLA-DMB,HLA-DOA,HLA-DOB,HLA-DPA1,HLA-DPB1,HLA-DPB2,HLA-DQA1,HLA-DQA2,HLA-DQB1,HLA-DQB2,HLA-DRA,HLA-DRB1,HLA-DRB5, HSD17B8, HSPA1A,HSPA1B, HSPA1L, LOC401252, LSM2, LST1,LTA,LTB,LY6G5B, LY6G5C, LY6G6C, LY6G6D, MCCD1, MEGT1, MICA, MICB, MSH5, NCR3, NEU1, NFKBIL1, NG36/G9a, NOTCH4, NR_002742, NR_002745, NR_002812, NR_002971, NR_003140, PBX2,PFDN6,PP199, PPT2, PRRT1, PSMB8,PSMB9,RAGE, RDBP, RGL2, RING1, RNF5, RP, RPS18, RXRB, SKIV2L, SLC39A7, SLC44A4, STK19, TAP1,TAP2, TAPBP,TNF,TNFa, TNXB, VARS, VPS52, WDR46, ZBTB12, ZBTB22 |
| chr2: 70616413-71523501 | 30 | 0 | ADD2, AF090102, ANKRD53, ATP6V1B1, CD207, CLEC4F, FIGLA, KIAA1155, MCEE, MPHOSPH10, N-Acetylglucosamine kinase, NAGK, NP220, OR7E91P, TEX261, TGFA, VAX2, ZNF638 |
| chr8: 95257759-96161427 | 28 | 0 | AF086017, AX747981, C8orf38, CCNE2, CDH17, DPY19L4, FSBP, GEM, INTS8, KIAA1429, RAD54B, RBM35A, TP53INP1, p53DINP1 |
| chr1: 184639488-185615061 | 24 | 0 | C1orf27, PDC, PLA2G4A, PTGS2 |
| chr4: 124486894-125137357 | 21 | 0 | AL833449, BC053945, SPRY1 |
| chr1: 226522770-226673588 | 20 | 0 | KIAA1556,KIAA1639,OBSCN, TRIM11, TRIM17 |
| chr21: 14806346-14824849 | 17 | 0 | HACS1,SAMSN1 |
| chr7: 84542383-84633646 | 16 | 0 | SEMA3D |
| chr4: 162635366-163113553 | 15 | 0 | FSTL5 |
| chr19: 48834611-49626859 | 15 | 0 | AK090553, AK098175, AK131520, AX748287, BC041923, BC045755, CADM4, CR593740, DKFZp564H1322, FLJ12886, HZF19, HZF6, IRGC, KCNN4, LYPD5, PLAUR ZNF155, ZNF221, ZNF222, ZNF223, ZNF224, ZNF225, ZNF226, ZNF227, ZNF228, ZNF229, ZNF230, ZNF233, ZNF234, ZNF235, ZNF284, ZNF285A, ZNF404, ZNF45 |
| chr4: 90603695-91299621 | 14 | 0 | AK123890, CR605611, KIAA1680, MGC48628, MMRN1, SNCA |
| chr6: 138020053-138532047 | 14 | 0 | AK124173, PERP, TNFAIP3 |
| chr7: 30225447-30798217 | 14 | 0 | AK096056, AK096687, AK097240, AL137445, BC016976, BC041636, BX648714, C7orf24, CR595731, CRH2R, CRHR2, FLJ22374, GARS, INMT, NOD1, NR_002186, ZNRF2 |
| chr12: 55685282-56515644 | 14 | 0 | ARHGAP9, AVIL, B4GALNT1, BC019026, BC033961, BC073932, CDK4, CENTG1, CR625050, CS444342, CTDSP2, CYP1, CYP27B1, DCTN2, DDIT3, DTX3, FAM119B, G43318, GEFT, GLI1, INHBC, INHBE, KIAA0286, KIAA1002, KIF5A, LRP1, MARCH9, MARS, MBD6, METTL1, MYO1A, NAB2, NDUFA4L2, NXPH4, OS9, PIP5K2C, R3HDM2, RGL1, SHMT2, SLC26A10, STAC3, STAT6, TAC3, TSFM, TSPAN31, ZBTB39, ZNEUROK1 |
| chr16: 86267434-86992013 | 14 | 0 | AK126852, AX747795, BANP, CA5A, DKFZp434G0522, FLJ00104, JPH3, KLHDC4, SLC7A5 |
| chr2: 179266611-179839804 | 13 | 0 | AK123298, CR624402, FLJ39502, SESTD1, TTN |
| chr3: 95106214-95125111 | 12 | 0 | PROS1 |
| chr2: 36745429-37640775 | 11 | 0 | AK001814, BC017652, CCDC75, CEBPZ, EIF2AK2, HEATR5B, KIAA1414, PRKD3, PRO1853, QPCT, STRN, SULT6B1, VIT |
| chr4: 151504432-151570906 | 11 | 0 | DKFZp686K03100,LRBA |
| chr11: 127094060-128138864 | 11 | 0 | AX747861, BC039676, DKFZp686D0662, ETS1, FLI1 |
| chr1: 31912222-32647867 | 10 | 0 | AK096192, BAI2, BAI2, BC069257, BC111382, BSDC1, C1orf90, C1orf91, CCDC28B, COL16A1, CR601100, |

TABLE 4-continued

Large Genic CNVs Impacting Single CVID Cases not Observed in Controls

| CNVR Del Singleton | Count SNPs | Distance From Exon | Gene |
|---|---|---|---|
| chr3: 106447305-107177994 | 10 | 0 | DCDC2B, DKFZp564C2082, DKFZp686B09139, EIF3S2, HDAC1, IQCC, KHDRBS1, KPNA6, LCK, LOC339483, MARCKSL1, PTP4A2, SPOCD1, TMEM39B, TSSK3, TXLNA, UNQ548 ALCAM,CBLB,Nbla00127 |
| chr6: 161278798-161959701 | 10 | 0 | AGPAT4, C6orf59, LPAAT-delta, MAP3K4, MTK1, PARK2, parkin |
| chr7: 24205709-24955079 | 10 | 0 | DFNA5, ICERE-1, KIAA0704, MPP6, NPY, OSBPL3 |

B) Deletions Not Impacting Known Immune Function Genes

| CNVR Del Singleton | Count SNPs | Distance From Exon | Gene |
|---|---|---|---|
| chr3: 163785970-165636507 | 94 | 0 | BC073807, LOC647107 |
| chr2: 78159130-78549747 | 86 | 0 | BC024248, BC030125 |
| chr3: 7053179-7177909 | 49 | 0 | GRM7 |
| chr11: 109142987-110423998 | 48 | 0 | AK094117, AK124179, ARHGAP20, DKFZp434I0812, FDX1, KIAA1726, NR_001287, RDX |
| chr12: 27002588-28111983 | 44 | 0 | AK000807, ARNTL2, BC043511, DKFZp564O1863, FGFR1OP2, KIAA0965, KIAA1230, KLHDC5, LOC728858, MDS023, MRPS35, PPFIBP1, PTHLH, REP15, STK38L, SURB7, TM7SF3 |
| chr6: 97170276-97625708 | 39 | 0 | C6orf66, FHL5, GPR63, KIAA1900, KLHL32 |
| chr6: 163188894-163315053 | 35 | 33591 | PACRG |
| chr16: 9624870-10467886 | 35 | 0 | ATF7IP2, DKFZp666E123, DQ587956, DQ595173, GRIN2A, U07199 |
| chr7: 64220284-64795508 | 34 | 0 | AK057766, DQ596928, FLJ25037, LOC441242, ZNF92 |
| chr5: 90035491-90386715 | 33 | 0 | GPR98, KIAA0686, VLGR1 |
| chr3: 37578530-37705809 | 32 | 0 | ITGA9 |
| chr6: 38413748-38630608 | 32 | 0 | BTBD9 |
| chr20: 51844911-51931244 | 28 | 0 | NR_002189 |
| chr15: 57055702-57917444 | 26 | 0 | BNIP3, CCNB2, DKFZp761D081, FAM81A, GCNT3, GTF2A2, LDHAL6B, MYO1E, RNF111 |
| chr15: 54225066-54550705 | 24 | 0 | MNS1, TEX9 |
| chr17: 3128134-3194433 | 23 | 0 | OR3A1, OR3A2, OR3A4 |
| chr7: 7480856-7819889 | 22 | 0 | AK027125, COL28, COL28A1, FLJ20323, RPA3 |
| chr10: 94222227-94754640 | 22 | 0 | EXOC6, HHEX, IDE, KIF11 |
| chr14: 91502061-91569101 | 21 | 0 | TRIP11, Trip230 |
| chr2: 42398844-43092929 | 19 | 0 | COX7A2L, EML4, HAAO, KCNG3, MTA3, OXER1 |
| chr14: 26535543-27350537 | 19 | 0 | BX538073 |
| chr14: 92744837-93367366 | 19 | 0 | BTBD7, C14orf130, COX8C, KIAA1409, PRIMA1 |
| chr2: 14622841-14924411 | 18 | 0 | AX747684, FAM84A |
| chr12: 10589522-10635183 | 17 | 0 | KLRA1 |
| chr3: 99229541-99419735 | 16 | 0 | CR749263, OR5AC2, OR5H1, OR5H14, OR5H15 |
| chr2: 132326867-132449751 | 15 | 0 | FLJ41821 |
| chr4: 9136858-9881191 | 15 | 0 | DKFZp586I2219, DQ581767, DQ583133, DQ584082, DQ585713, DQ589421, DRD5, SLC2A9, WDR1 |
| chr4: 128805691-128920529 | 15 | 0 | INTU, SLC25A31 |
| chr9: 16987947-17478111 | 15 | 0 | C9orf39, RP11-340N12.1 |
| chr14: 59952568-60075378 | 15 | 0 | C14orf39, SIX6 |
| chr18: 5682313-5922670 | 15 | 0 | AF301223, TTMA |
| chr19: 23304120-23389292 | 15 | 0 | AK022793, BC038574, BC043213, ZNF91 |
| chr12: 39980210-40809427 | 14 | 0 | GLT8D3, PDZRN4 |
| chr19: 19759149-20368239 | 14 | 0 | CR593334, CR614976, DKFZp761G18121, FLJ44894, NR_003128, ZNF253, ZNF486, ZNF506, ZNF682, ZNF90, ZNF93 |
| chr2: 98228529-98252357 | 13 | 0 | DKFZp434J0326, DKFZp451I0318, MGC26733 |
| chr2: 168309981-169429627 | 13 | 0 | AL080192, B3GALT1, BC035245, LASS6, NOSTRIN, STK39 |
| chr4: 22663503-22803604 | 13 | 0 | CR607430 |
| chr5: 107695465-109245567 | 13 | 0 | AK021888, BC034788, FBXL17, FER, MAN2A1, PJA2 |
| chr4: 20984915-21185852 | 12 | 0 | KCNIP4 |
| chr5: 178315216-178514465 | 12 | 0 | ADAMTS2, BX648737, CR598488, GRM6, ZNF354C, ZNF454, mGluR6 |
| chr17: 55759021-56436171 | 12 | 0 | APPBP2, BCAS3, C17orf64, L32131, PPM1D, USP32 |
| chr18: 60137564-60597211 | 12 | 0 | BC036306 |
| chr5: 38305919-38317501 | 11 | 11209 | EGFLAM |
| chr6: 12643097-13219417 | 11 | 0 | PHACTR1, RPEL |
| chr4: 69405358-69494103 | 10 | 0 | TMPRSS11E |
| chr9: 40497792-40617437 | 10 | 0 | AK024257 |
| chr11: 102824056-102856185 | 10 | 0 | DYNC2H1 |
| chr11: 124360372-124420328 | 10 | 0 | CCDC15 |
| chr12: 47817725-47931507 | 10 | 0 | TUBA1A, TUBA1B, TUBA1C |
| chr14: 62671250-62971495 | 10 | 0 | GPHB5, PPP2R5E, RHOJ |
| chr15: 91046103-91378387 | 10 | 0 | CHD2, DKFZp781D1727, LOC400451 |

C) Duplications Impacting Immune Function Genes

| CNVR Del Singleton | Count SNPs | Distance From Exon | Gene |
|---|---|---|---|
| chr19: 5773490-12007370 | 827 | 0 | ACP5, ACSBG2, ADAMTS10, AF019226, AF075036, AF161365, AK056073, AK097685, AK124717, ALKBH7, ANGPTL4, ANGPTL6, ANKRD25, ANKRD47, AP1M2, ARHGEF18, ASAH3, ATG4D, AX747405, AX747599, AX748210, AY203940, BC007593, BC014506, BC029904, BC033124, BC039523, BC042816, BGR, C19orf39, C19orf45, C19orf52, C19orf59, C3, CAPS, CARM1, CCL25, CD209, CD320, CD70, CDKN2D, CLEC4G, CLEC4M, CLPP, CNN1, COL5A3, CR598956, CRB3, CTXN1, DENND1C, DKFZp547H118, DKFZp564K0223, DKFZp564O1762, DKFZp666A071, DKFZp667O2312, DKFZp761J1410, DKFZp761K0816, DNM2, DNMT1, DOCK6, ECSIT, EDG5, EDG8, EIF3S4, ELAVL1, ELAVL3, ELOF1, EMR1, EMR4, EPOR, EVI5L, FBN3, FBXL12, FCER2, FLJ00153, FLJ11286, FLJ12949, |

TABLE 4-continued

Large Genic CNVs Impacting Single CVID Cases not Observed in Controls

| CNVR Del Singleton | Count SNPs | Distance From Exon | Gene |
|---|---|---|---|
| | | | FLJ20079, FLJ22184, FLJ25758, FUT3, FUT5, FUT6, GPR108, GTF2F1, HNRPM, HSZFP36, ICAM1, ICAM3, ICAM4, ICAM5, ILF3, INSR, KEAP1, KHSRP, KIAA0521, KIAA1395, KIAA1518, KIAA1543, KIAA1588, KIAA1776, KIAA1978, LASS4, LDLR, LOC126075, LOC162993, LOC388503, LOC401898, LOC440508, LOC55908, LPPR2, LRRC8E, MAP2K7, MARCH2, MBD3L1, MBD3L2, MCOLN1, MGC19604, MGC20983, MGC33407, MKK7, MLLT1, MRPL4, MUC16, MYO1F, MYO1F variant protein, NDUFA11, NDUFA7, NRTN, OLFM2, OR1M1, OR2Z1, OR7D2, OR7D4, OR7E24, OR7G1, OR7G2, OR7G3, P2RY11, PCP2, PDE4A, PEX11G, PIN1, PNPLA6, PPAN, PPAN-P2RY11, PRAM1, PRKCSH, PSPN, QTRT1, RAB11B, RAB3D, RANBP3, RAVER1, RDH8, RETN, RFX2, RGL3, RPS28, SH2D3A, SLC25A23, SLC25A41, SLC44A2, SMARCA4, SNAPC2, SPC24, STXBP2, TIMM44, TMED1, TNFSF14, TNFSF9, TRAPPC5, TRIP10, TSPAN16, TUBB4, TYK2, UBL5, UNQ2443, UNQ501, VAV1, VMAC, XAB2, YIPF2, ZNF121, ZNF177, ZNF266, ZNF317, ZNF358, ZNF414, ZNF426, ZNF433, ZNF439, ZNF440, ZNF441, ZNF491, ZNF557, ZNF558, ZNF559, ZNF560, ZNF561, ZNF562, ZNF627, ZNF653, ZNF69, ZNF699, ZNF700, ZNF763, pp10122 |
| chr14: 92664804-95787550 | 448 | 0 | AK125038, ASB2, BC016484, BC037859, BC038791, BDKRB2, BTBD7, BX247990, C14orf109, C14orf130, C14orf132, C14orf139, C14orf142, C14orf152, C14orf48, C14orf49, CLMN, COX8C, CR611440, DDX24, DICER1, FAM14A, FAM14B, GIG24, GLRX5, GSC, IFI27, KIAA0928, KIAA1409, KIAA1622, MOAP1, NM_207443, NR_001459, NR_003002, OTUB2, P27, PRIMA1, SERPINA1, SERPINA10, SERPINA11, SERPINA12, SERPINA13, SERPINA3, SERPINA4, SERPINA5, SERPINA6, SERPINA9, TCL1A, TCL1B, TCL6, TCL6a1, TCL6d1, TML1 |
| chr11: 7678446-10337351 | 315 | 0 | ADM, AK000908, AK055772, AK090613, ASCL3, AX747224, BC017787, BC027619, BC068088, BC073899, BCA3, C11orf16, C11orf17, CMT4B2, CR598129, DKFZp451C1317, DKFZp686I18166, EIF3S5, IPO7, KIAA0298, KIAA1766, LMO1, MGC10850, NLRP10, NRIP3, NR_002580, NR_002962, NR_002977, OR10A3, OR10A6, OR5E1P, OR5P2, OR5P3, OVCH2, RAB6IP1, RIC3, RPL27A, SBF2, SCUBE2, ST5, STK33, SWAP70, TMEM41B, TMEM9B, TUB, U80769, WEE1, ZNF143 |
| chr13: 100600344-103567030 | 197 | 0 | AK093430, AK096424, AK125748, AX747578, BIVM, C13orf27, CR616826, DKFZp434L2319, ERCC5, FGF14, ITGBL1, KDELC1, LOC196541, RP11-430M15.2-003, SLC10A2, TPP2, UNQ1910, VGCNL1 |
| chr14: 65357663-66177823 | 159 | 0 | CR594591, GPHN, MGC88374 |
| chr4: 119628184-120591177 | 158 | 0 | AK000709, AK024248, AK097701, AK098126, BC035733, BC070391, CEP170L, DQ574659, DQ575011, DQ575856, DQ576410, DQ582480, DQ599872, FABP2, KIAA0755, KIAA1627, LOC401152, MYOZ2, Myopodin, SEC24D, SYNPO2, USP53 |
| chr8: 106761674-108458326 | 156 | 0 | ABRA, ANGPT1, CR602836, Nbla00307, OXR1, ZFPM2 |
| chr4: 113049611-113759418 | 129 | 0 | ALPK1, C4orf16, C4orf21, C4orf32, CR590073, DKFZp434C0927, FLJ00302, KIAA1527, LOC91431, NEUROG2, TIFA |
| chr15: 40145534-40608559 | 90 | 0 | CAPN3, GANC, KIAA0770, PLA2G4D, PLA2G4F, SNAP23, TMEM87A, VPS39, ZFP106 |
| chr14: 43658461-45064383 | 87 | 0 | AX748292, BC038722, C14orf106, C14orf155, C14orf28, FANCM, FKBP3, KIAA0423, KLHL28, PRPF39 |
| chr10: 67399581-69536663 | 75 | 0 | CTNNA3, DNAJC12, HERC4, LRRTM3, MYPN, SIRT1 |
| chr3: 107041527-108030375 | 71 | 0 | CBLB |
| chr9: 137454076-139460602 | 70 | 0 | ABCA2, AF161442, AGPAT2, AK023162, AK054908, AK055547, AK090585, AK096249, AK098241, AK128153, AK128864, AL832276, ANAPC2, AX747706, AY952890, BC015688, BC032375, BC034456, BC042667, BC043225, BC061888, BC064596, BC092490, BC101937, BTBD14A, C8G, C9orf116, C9orf139, C9orf140, C9orf142, C9orf163, C9orf167, C9orf75, C9orf86, CAMSAP1, CARD9, CLIC3, COBRA1, CR614579, CR619051, DKFZp434B205, DKFZp564M173, DKFZp762I052, DPP7, EDF1, EGFL7, ENTPD2, ENTPD8, FAM69B, FBXW5, FLJ20433, FLJ45224, FUT7, GBDR1, GLT6D1, GPSM1, GRIN1, HBE269, INPP5E, KCNT1, KIAA0310, KIAA0649, KIAA1062, KIAA1422, KIAA1984, LCN1, LCN10, LCN12, LCN6, LCN8, LCN9, LHX3, LOC389813, LOC389816, LOC401565, LOC441476, LOC728489, MAMDC4, MAN1B1, MGC14327, MGC59937, MGC61598, MRP-S2, MRPS2, NDOR1, NOTCH1, NOXA1, NPDC1, NPTIIc, NR1, NR_002958, NR_002975, OBP2A, PAEP, PHPT1, PMPCA, PTGDS, QSCN6L1, RNF208, RP11-100C15.2, RP11-413M3.10, SDCCAG3, SLC34A3, SNAPC4, SOHLH1, SSNA1, TMEM141, TRAF2, TUBB2C, UAP1L1, UBADC1, UNQ2492, UNQ2541, UNQ747, hNMDAR1-3b, pp8875, ve-statin |
| chr18: 73989470-76116152 | 60 | 0 | AK056304, ATP9B, AX746671, BC016878, BC017654, BC040056, BX537710, C18orf22, CTDP1, DKFZp434A042, KCNG2, NFATC1, PARD6G, PQLC1, SALL3, TXNL4A, ZNF508, hdim1+ |
| chr9: 134048500-135886847 | 54 | 0 | ABO, ADAMTS13, ADAMTSL2, AJ011378, AK123314, AX748058, BARHL1, C9orf166, C9orf7, C9orf9, C9orf96, C9orf98, CEL, CELL, CR592591, CR593670, DBH, DDX31, EEF1A1, FLJ46082, GBGT1, GFI1B, GTF3C4, GTF3C5, KIAA1308, LOC389827, NR_002783, NTNG2, OBP2B, RALGDS, REXO4, RPL7A, SARDH, SETX, SLC2A6, SURF1, SURF2, SURF4, SURF5, SURF6, TSC1, TTF1, UNQ2513, VAV2, XPMC2H, vWF-CP |
| chr1: 2182293-3539057 | 50 | 0 | ACTRT2, AK021767, AK124865, ARHGEF16, BC114358, C1orf93, CR749717, DQ601700, FAM79A, FLJ42875, HES5, MEGF6, MMEL1, MORN1, PANK4, PEX10, PLCH2, PRDM16, RER1, RP3-395M20.1, RP3-395M20.10, RP4-740C4.2, SKI, TNFRSF14, WDR8 |
| chr1: 245537326-245976637 | 49 | 0 | AB120962, AK130400, BC034303, C1orf150, CIAS1, NLRP3, OR13G1, OR2B11, OR2C3, OR2G2, OR2G3, OR2W3, OR5AY1, OR6F1, ZNF496 |

TABLE 4-continued

Large Genic CNVs Impacting Single CVID Cases not Observed in Controls

| CNVR Del Singleton | Count SNPs | Distance From Exon | Gene |
|---|---|---|---|
| chr14: 21582956-21976908 | 47 | 0 | AK093552, AK125397, AV1S3A1T, AV25S1, AV4S1, TCR-[alpha]V33.1,TCR-alpha,TCRA,TCRAV14.1a,TCRAVN1,TCRD,TRA@,Valpha immunoglobulin, av27s1, hADV14S1,hADV23S1,hADV29S1,hADV38S2,hDV102S1 |
| chr7: 157944418-158676623 | 46 | 0 | AX746826, BC041429, BC042556, FAM62B, KIAA1228, NCAPG2, PTPRN2, VIPR2, WDR60 |
| chr19: 48498399-48562727 | 46 | 0 | CD177 |
| chr22: 34946021-35041308 | 41 | 0 | APOL1, APOL2, AX747758, MYH9 |
| chr1: 113185538-113437683 | 40 | 0 | AFARP1, AX748125, BC023568, BC037540, BC047723, BX648855, LRIG2, SLC16A1 |
| chr2: 187993955-189286647 | 39 | 0 | CALCRL, CED-6, GULP1, TFPI |
| chr11: 382079-1386192 | 38 | 0 | AK094678, AK126635, AP2A2, AX747537, AX748330, BC031953, BC048998, BC066355, BRSK2, C11orf35, CD151, CEND1, CHID1, DEAF1, DKFZp434K249, DRD4, EFCAB4A, EPS8L2, HRAS, IRF7, KIAA0899, KIAA1542, LRDD, LRRC56, MG1, MUC5AC, MUC2, MUC5AC, MUC5B, MUC6, MUCDHL, NR_002585, PDDC1, PEN11B, PKP3, PNPLA2, POLR2L, PTDSS2, RASSF7, RNH1, RPLP2, SCT, SIGIRR, SLC25A22, TALDO1, TMEM16J, TMEM80, TOLLIP, TSPAN4, tollip |
| chr12: 98815353-99473749 | 37 | 0 | ACTR6, ANKS1B, AX746635, BC048272, BC062763, DEPDC4, DKFZp434M0331, DQ579381, DQ583972, DQ595598, DQ598729, EB-1, GOLGA2L1, KIAA0701, NR1H4, SCYL2, SLC17A8, hArpX |
| chr4: 7568079-8105372 | 36 | 0 | ABLIM2, AFAP1, AJ431609, BC043614, KIAA1808, LOC389199, SORCS2 |
| chr14: 23995185-24062459 | 30 | 0 | AK056368, CMA1 |
| chr14: 103352857-104756910 | 30 | 0 | ADSS, ADSSL1, AK057986, AK094143, AKT1, AX721091, AX746996, BRF, BRF1, C14orf151, C14orf173, C14orf2, C14orf78, C14orf79, CDCA4, CR602005, DKFZp434N0820, DKFZp434N178, DKFZp686J02145, GPR132, JAG2, KIAA0284, KIAA0771, KIF26A, LOC374569, LOC400258, MGC23270, NUDT14, PLD4, PPP1R13B, SIVA1, TDRD9, TMEM179, UGPP |
| chr17: 73662981-73765190 | 23 | 0 | AFMID, BC036810, BIRC5, EPR-1, SYNGR2, TK1, UNQ464/PRO809, survivin-3B |
| chr13: 45066410-45918722 | 22 | 0 | AK095119, AK124928, C13orf18, CPB2, FLJ32682, KIAA0853, LCP1, LOC220416, LOC283514, RP11-139H14.4-001, RP11-351K3.2-001, SPERT, ZC3H13 |
| chr19: 46758119-46863746 | 21 | 0 | CEACAM21, CEACAM4, UNQ3098 |
| chr8: 6849317-6889488 | 20 | 0 | AF355799, DEFA3 |
| chr20: 60320976-62223928 | 17 | 0 | AK056267, AK128329, AL137301, ARFGAP1, ARFRP1, AX747649, AY940852, BC002534, BC025345, BC069708, BC127852, BHLHB4, BIRC7, C20orf11, C20orf135, C20orf149, C20orf151, C20orf166, C20orf195, C20orf20, C20orf58, C20orf59, CABLES2, CHRNA4, COL20A1, COL9A3, DIDO1, DNAJC5, EEF1A2, FLJ00084, FLJ00118, FLJ30313, GATA5, GMEB2, HRIHFB2281, KCNQ2, KIAA1088, KIAA1269, KIAA1510, LAMA5, LIME1, LOC198437, NPBWR2, NR_003244, NR_003245, NTSR1, OATP-E, OGFR, OK/SW-cl.69, 0PRL1, PRIC285, PRPF6, PRR17, PTK6, RGS19, RP4-697K14.11, RPS21, RTEL1, SAMD10, SLC2A4RG, SLCO4A1, SOX18, SRMS, STMN3, Si-1-2-19, TCEA2, TCFL5, TNFRSF6B, TPD52L2, UCKL1, URKL1, YTHDF1, ZBTB46, ZGPAT, ZNF512B |
| chr2: 86924985-87026840 | 16 | 0 | CD8B, RGPD1, RMND5A |
| chr6: 128245227-128538250 | 16 | 0 | C6orf190, PTPRK |
| chr1: 111628132-111661435 | 15 | 0 | CHIA, RP11-165H20.1 |
| chr7: 80041654-80110504 | 13 | 0 | CD36 |
| chr12: 6085895-6134080 | 11 | 0 | VWF |
| chr12: 17854127-19338878 | 11 | 0 | CAPZA3, FLJ22655, PIK3C2G, PLCZ1, PLEKHA5 |
| D) Duplications Not Impacting Known Immune Function Genes | | | |
| chr8: 430424-977192 | 189 | 0 | AK128400, BC022082, BC038783, C8orf42, DQ584928, ERICH1, LOC389607 |
| chr10: 2682656-3123648 | 157 | 0 | PFKP |
| chr19: 21575835-22802826 | 152 | 0 | BC030765, CR936832, FKSG70, ZNF100, ZNF208, ZNF257, ZNF43, ZNF492, ZNF676, ZNF99 |
| chr6: 63118894-64091007 | 116 | 0 | GLULD1, LGS |
| chr2: 126935385-127317174 | 98 | 0 | GYPC |
| chr5: 169763949-170518986 | 96 | 0 | DKFZp666P032, GABRP, KCNIP1, RANBP17 |
| chr6: 1977258-2424512 | 92 | 0 | AJ420566, AK023629, AK091028, CR598484, GMDS |
| chr1: 145196592-145539979 | 65 | 0 | BC036212, BCL9, CHD1L |
| chr3: 62813828-63789968 | 63 | 0 | BC043407, C3orf49, CADPS, FLJ44379, SYNPR |
| chr5: 172824934-173106866 | 62 | 0 | BC033564, FAM44B |
| chr3: 83912925-84849961 | 54 | 0 | BC068246 |
| chr11: 106523381-106702850 | 54 | 0 | CWF19L2 |
| chr7: 50911090-51127086 | 50 | 0 | COBL |
| chr9: 6557841-7007391 | 41 | 0 | AK098534, BC042976, GLDC, JMJD2C, KIAA0780 |
| chr17: 793231-917163 | 40 | 0 | ABR, NXN, TIMM22 |
| chr3: 148425802-149211699 | 39 | 0 | AK098763, ZIC1, ZIC4 |
| chr13: 62536330-64097876 | 36 | 0 | AK057471, AK097490, AK098560, BC128161, NR_002171 |
| chr4: 92669000-94351161 | 34 | 0 | GRID2, KIAA1680 |
| chr3: 11041670-11154453 | 33 | 0 | SLC6A1 |
| chr4: 141709869-141939520 | 33 | 0 | TBC1D9 |
| chr13: 113032851-113140550 | 30 | 0 | ADPRHL1, GRTP1 |
| chr2: 148947731-149053581 | 29 | 0 | KIAA1461, MBD5 |
| chr3: 141649121-141911988 | 28 | 0 | CLSTN2, TRIM42 |
| chr12: 20901315-21459060 | 27 | 0 | IAPP, LST-3TM12, LST3, SLCO1A2, SLCO1B1, SLCO1B3 |

TABLE 4-continued

Large Genic CNVs Impacting Single CVID Cases not Observed in Controls

| CNVR Del Singleton | Count SNPs | Distance From Exon | Gene |
|---|---|---|---|
| chr12: 130676799-131128244 | 27 | 0 | EP400, KIAA1498, KIAA1818, MMP17, NR_002979, PUS1, SFRS8, ULK1 |
| chr7: 34919485-35862821 | 26 | 0 | AJ011981, BC049371, BC084560, CR593784, CR595224, DPY19L1, DPY19L2P1, HERPUD2, KIAA0877, SEPT7, T8X20 |
| chr1: 30940148-31013899 | 25 | 0 | BC044253, LAPTM5, MATN1 |
| chr4: 63433227-65099386 | 25 | 0 | SRD5A2L2 |
| chr5: 12838251-13150705 | 22 | 0 | AY328033 |
| chr6: 138653005-138759016 | 22 | 0 | KIAA1244 |
| chr1: 103111860-103157198 | 21 | 0 | COL11A1 |
| chr6: 34836231-34976532 | 21 | 0 | ANKS1A, C6orf107, SNRPC, TAF11 |
| chr15: 27167056-28188067 | 21 | 0 | APBA2, BC043570, BC070492, BC071630, BC071855, DQ572986, DQ573498, DQ575284, DQ575742, DQ577333, DQ578370, DQ578838, DQ582641, DQ582940, DQ590322, DQ592322, DQ595055, DQ596303, DQ596319, DQ597873, KIAA0574, NDNL2, TJP1, hXIIL |
| chr2: 3287465-3327227 | 20 | 0 | TSSC1 |
| chr10: 98101269-98152781 | 19 | 0 | TLL2, TMEM10 |
| chr1: 79037280-79973037 | 18 | 0 | ELTD1 |
| chr4: 68749536-70089270 | 18 | 0 | AK123556, TMPRSS11B, TMPRSS11E, UGT2A3, UGT2B10, UGT2B15, UGT2B17, UGT2B7, YTHDC1 |
| chr2: 27584444-28424525 | 17 | 0 | AK124439, BC041993, BC048132, BRE, C2orf16, CCDC121, GCKR, MRPL33, RBKS, SLC4A1AP, SUPT7L, XAB1, ZNF512 |
| chr2: 172356838-172528561 | 17 | 0 | HAT1, SLC25A12 |
| chr2: 180123158-180216026 | 16 | 0 | ZNF533 |
| chr4: 15529521-15552238 | 15 | 0 | FGFBP1 |
| chr18: 14805527-14905835 | 15 | 0 | ANKRD30B |
| chr5: 1601764-1621442 | 14 | 0 | CR749689 |
| chr10: 88722456-89266679 | 14 | 0 | AK091716, BC036645, BC047063, BC065757, BC082979, BC092519, CR609725, CR614919, FAM35A, GLUD1, KIAA1975, KIAA2020, MINPP1 |
| chr1: 225308870-225407413 | 13 | 0 | CDC42BPA |
| chr7: 74674968-74738702 | 13 | 0 | LOC441257, PMS2L14 |
| chr1: 193808000-194531039 | 12 | 0 | KCNT2, SLICK |
| chr2: 165344115-165435694 | 12 | 0 | COBLL1, KIAA0977 |
| chr6: 123847128-124726881 | 12 | 0 | TCBA1, TRDN |
| chr16: 26961662-26994169 | 12 | 0 | TNT |
| chr6: 102029392-102048325 | 11 | 11862 | GRIK2 |
| chr8: 11397047-11414199 | 11 | 0 | BLK |
| chr8: 27689983-27745887 | 11 | 0 | ESCO2, PBK |
| chr2: 77709215-78761206 | 10 | 0 | BC024248, BC030125 |
| chr11: 5444172-5454375 | 10 | 11939 | HBE1, HBG2, OR51B5 |
| chr11: 19571323-19595111 | 10 | 96377 | NAV2 |
| chr18: 68553733-69070964 | 10 | 0 | BC013370, BC034583, NETO1 |
| chr19: 34552727-34574348 | 10 | 0 | AK094793 |
| chr4: 2059850-2960297 | 10 | 0 | AB000464, AB000465, AB000466, ADD1, AK054619, BC010180, BC032331, C4orf10, C4orf15, C4orf8, CR622423, GRK4, KIAA1643, MXD4, Mad4, NOL14, POLN, RNF4, SH3BP2, TETRAN, TNIP2, ZFYVE28 |

TABLE 5

Homozygous Deletions Observed Exclusive to Cases

| CNVR | Cases Loss | Gene | Distance | Distance From Exon |
|---|---|---|---|---|
| chr3: 100430538-100430538 | 2 | CLCP1, DCBLD2 | 327315 | 327315 |
| chr2: 118777060-118778863 | 1 | INSIG2 | 192993 | 192993 |
| chr3: 146130742-146141275 | 1 | DQ595575 | 883692 | 883692 |
| chr5: 29455914-29488308 | 1 | AK098570 | 247692 | 247692 |
| chr5: 141998044-142000692 | 1 | FGF1 | 0 | 16953 |
| chr6: 32525108-32530999 | 1 | HLA-DRA | 4306 | 4306 |
| chr6: 62122152-62144592 | 1 | G43499 | 251536 | 251536 |
| chr6: 77159914-77159914 | 1 | IMPG1 | 320859 | 320859 |
| chr6: 128018101-128024702 | 1 | C6orf190 | 46336 | 46336 |
| chr12: 17277311-17282429 | 1 | LMO3, Nbla03267 | 625020 | 625020 |

TABLE 6

Genome Global CNV Burden

Significant Including Common CNV Exonic

| | Locus Exonic Significant Case Enriched | Locus Non-Exonic Case Enriched | Locus Exonic Significant Control Enriched | Locus Non-Exonic Control Enriched | P | DifFreq |
|---|---|---|---|---|---|---|
| Deletion | 21 | 61 | 8 | 67 | 0.022628 | 0.149431 |
| Duplication | 43 | 173 | 12 | 12 | 0.003336 | −0.30093 |

| | Case CNV Calls Exonic | Case CNV Calls Non-Exonic | Control CNV Calls Exonic | Control CNV Calls Non-Exonic | P | DifFreq |
|---|---|---|---|---|---|---|
| | | | Rare CNV Exonic | | | |
| Deletion | 527 | 1149 | 3970 | 10290 | 0.002138 | 0.036038 |
| Duplication | 813 | 1785 | 5539 | 5997 | 2.45E−55 | −0.16722 |
| | | | Rare CNV >100 KB Exonic | | | |
| Deletion | 136 | 83 | 1012 | 653 | 0.768312 | 0.013197 |
| Duplication | 278 | 146 | 2263 | 546 | 2.46E−11 | −0.14996 |

Samples w Rare CNV >100 KB (Impacting gene or not)

| | Case with large rare CNV | Case without large rare CNV | Control with large rare CNV | Control without large rare CNV | P | DifFreq |
|---|---|---|---|---|---|---|
| Deletion | 131 | 180 | 1156 | 1610 | 0.951669 | 0.00329 |
| Duplication | 186 | 125 | 1391 | 1375 | 0.001504 | 0.095178 |

Figure 1C:
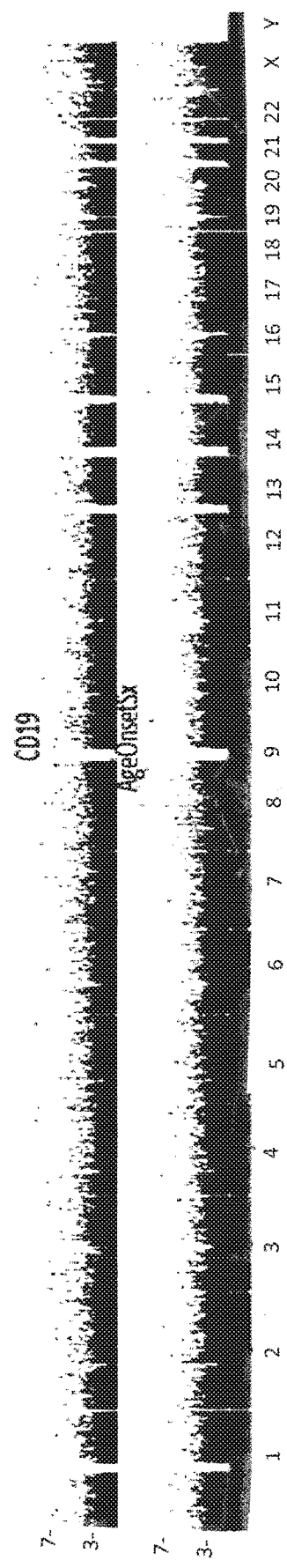
Figure 5:
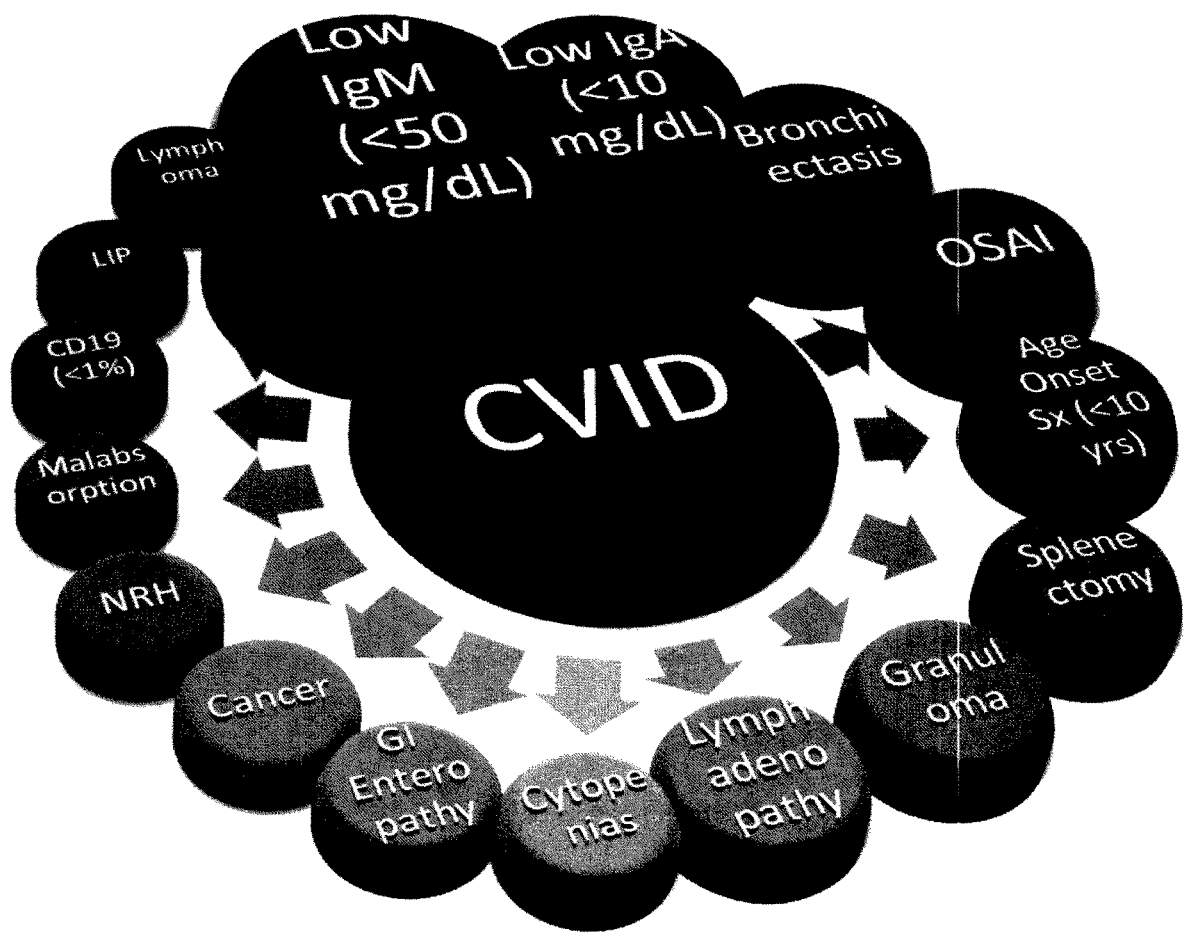

Finally, to address the heterogeneity of the CVID phenotype and comorbid clinical manifestations that affect subsets of patients, we compared CVID patients with common sub-phenotypes to patients without any additional comorbidities. Based on recent phenotypic characterization[22], we established 16 distinct clinical subtracks within CVID to study: cancer, lymphoma, lymphadenopathy, nodular regenerative hyperplasia of the liver (NRH), lymphoid interstitial pneumonitis (LIP), bronchiectasis, biopsy proven granuloma, GI enteropathy, malabsorption, splenectomy, cytopenias, organ specific autoimmunity (OSAI), low IgM (<50 mg/dL), low IgA (<10 mg/dL), low B cells (CD19+ cells <1%), and young age of symptom onset (<10 yrs) (FIG. 5 and Table 7). The case and control labels within the CVID cohort were based on previously defined criteria. Differences in genotype frequencies were assigned significance and regions with multiple significant SNPs were then scored. Significant SNP associations were made for all subsets (Table 8 and FIG. 1C). The most significant association was observed with NRH on AK096081-AK124028 ($P=2.29\times10^{-10}$). Lymphoma was associated with KIAA0834, PFTK1 and HAVCR1, with corresponding P values ranging from $P=1.69\times10^{-8}$-$3.62\times10^{-8}$. An association was also observed between LIP and FGF14 and ZNF81, with corresponding P values of $P=5.76\times10^{-8}$ and $P=7.70\times10^{-8}$, respectively. OSAI also associated with SNX31 ($P=6.89\times10^{-8}$) and low IgM levels (<50 mg/dL) in the case subjects were associated with LDLRAP1 ($P=6.02\times10^{-8}$). Patients with CVID manifesting enteropathy and their resulting subphenotype significance were additionally queried against the IBD significance observations to assess if specific loci contributed to a common etiology. The SNP rs12889533 was significant in both CVID+enteropathy and IBD with allele frequency difference in the same direction (Table 9).

TABLE 7

CVID Subphenotypes and Sample Sizes

| CVID Subphenotype | Cases | Controls |
|---|---|---|
| Cancer | 13 | 249 |
| Lymphoma | 9 | 253 |
| Lymphadenopathy | 30 | 232 |
| NRH | 13 | 249 |
| LIP | 10 | 252 |
| Bronchiectasis | 78 | 184 |
| Granuloma | 34 | 228 |
| GIEnteropathy | 19 | 243 |
| Malabsorption | 13 | 249 |
| Splenectomy | 40 | 222 |
| Cytopenias | 27 | 235 |
| OSAI | 75 | 187 |
| Low IgM (<50 mg/dL) | 206 | 56 |
| Low IgA (<10 mg/dL) | 160 | 102 |
| CD19 (<1%) | 11 | 251 |
| AgeOnsetSx (<10 yrs) | 42 | 220 |

TABLE 8

Most Significant Associated Regions Based on Subphenotype Genotype Association

| Significant Region | P-value | SNP | A1 | F_A | F_U | OR | Count SNPs | Gene | Distance | Distance From Exon | Subphenotype |
|---|---|---|---|---|---|---|---|---|---|---|---|
| chr1: 68153970-68161019 | 2.29E−10 | rs1926283 | C | 0.2308 | 0.01807 | 16.3 | 3 | AK096081, AK124028 | 0 | 33408 | NRH |
| chrX: 132092989-132095451 | 5.50E−10 | rs5977837 | C | 0.2778 | 0.02174 | 17.31 | 2 | TFDP3 | 82912 | 82912 | Lymphoma |
| chr10: 58755852-58767334 | 1.36E−09 | rs16910534 | T | 0.2222 | 0.01383 | 20.37 | 3 | IPMK | 858286 | 858286 | Lymphoma |
| chr20: 55901032-55985359 | 3.21E−09 | rs8124301 | T | 0.4231 | 0.07631 | 8.877 | 5 | C20orf85 | 174030 | 174030 | Malabsorption |
| chr7: 90245135-90245280 | 1.69E−08 | rs975004 | G | 0.3333 | 0.03953 | 12.15 | 2 | KIAA0834, PFTK1 | 0 | 12544 | Lymphoma |
| chr5: 156402979-156407976 | 3.62E−08 | rs10038271 | T | 0.7222 | 0.1877 | 11.25 | 2 | HAVCR1 | 0 | 651 | Lymphoma |
| chrX: 22422160-22428888 | 5.71E−08 | rs5925651 | A | 0.3462 | 0.1386 | 3.291 | 3 | ZNF645 | 219665 | 219665 | Bronchiectasis |
| chr13: 101641990-101673539 | 5.76E−08 | rs1336698 | G | 0.65 | 0.168 | 9.197 | 6 | FGF14 | 0 | 69139 | LIP |
| chr1: 25735669-25753653 | 6.02E−08 | rs2065970 | G | 0.06553 | 0.2411 | 4.529 | 5 | LDLRAP1 | 0 | 0 | Low IgM |
| chrX: 143116309-143119321 | 6.77E−08 | rs6649722 | A | 0.3 | 0.0377 | 10.94 | 3 | UBE2NL | 320286 | 320286 | LIP |
| chr8: 101728102-101728344 | 6.89E−08 | rs7815950 | G | 0.2133 | 0.05615 | 4.559 | 2 | SNX31 | 0 | 2334 | OSAI |
| chr8: 13834782-13842376 | 7.62E−08 | rs2682665 | C | 0.1818 | 0.01394 | 15.71 | 3 | SGCZ | 149368 | 149368 | Low B cells |
| chrX: 47642545-47651320 | 7.70E−08 | rs12387999 | A | 0.2 | 0.016 | 15.38 | 2 | ZNF81 | 0 | 2262 | LIP |
| chrX: 152295068-152303019 | 9.84E−08 | rs5987017 | A | 0.2143 | 0.04773 | 5.442 | 4 | ZNF275 | 24829 | 24829 | Young age |
| chr12: 2531014-2538733 | 1.21E−07 | rs4765961 | C | 0.4737 | 0.142 | 5.439 | 3 | CACNA1C | 0 | 0 | GI Enteropathy |
| chrX: 30733771-30736604 | 1.44E−07 | rs11095197 | T | 0.1469 | 0.3431 | 3.034 | 2 | MAP3K7IP3 | 18876 | 18876 | Low IgA |
| chrX: 37803525-37832251 | 1.54E−07 | rs5918500 | C | 0.4878 | 0.2123 | 3.533 | 3 | SYTL5 | 0 | 0 | Young age |
| chrX: 53035117-53039801 | 1.90E−07 | rs10127016 | G | 0.3833 | 0.125 | 4.351 | 2 | TMEM29 | 0 | 1409 | Lymphadenopathy |
| chr7: 107306707-107314113 | 2.16E−07 | rs9690688 | A | 0.3636 | 0.06375 | 8.393 | 2 | DLD | 4709 | 4709 | Low B cells |
| chr21: 18188480-18192815 | 2.84E−07 | rs7280675 | G | 0.1923 | 0.02008 | 11.62 | 2 | CHODL | 2636 | 2636 | NRH |
| chr1: 55704352-55706323 | 2.85E−07 | rs356086 | G | 0.1111 | 0.00395 | 31.5 | 2 | FLJ45337 | 112975 | 112975 | Lymphoma |
| chr21: 45476504-45476918 | 3.23E−07 | rs4592938 | A | 0.1154 | 0.00602 | 21.52 | 2 | C21orf89 | 1777 | 1777 | NRH |
| chr14: 23168471-23169215 | 4.57E−07 | rs222723 | C | 0.6154 | 0.1968 | 6.531 | 2 | DHRS2 | 0 | 0 | Cancer |
| chr2: 109118795-109120561 | 4.62E−07 | rs375099 | C | 0.25 | 0.02976 | 10.87 | 2 | POSH2 | 0 | 5794 | LIP |
| chr12: 30583074-30598457 | 4.82E−07 | rs1905675 | C | 0.2 | 0.5453 | 0.209 | 2 | IPO8 | 74732 | 74732 | Lymphadenopathy |
| chrX: 39933689-39956544 | 5.18E−07 | rs2948491 | A | 0.18 | 0.04545 | 4.61 | 4 | BCOR | 12163 | 12163 | OSAI |
| chr14: 64723761-64783067 | 8.09E−07 | rs4299072 | A | 0.1667 | 0.02802 | 6.938 | 4 | BX161428 | 0 | 0 | Lymphadenopathy |
| chr7: 117377201-117382435 | 9.94E−07 | rs17140937 | C | 0.2692 | 0.04418 | 7.971 | 2 | CTTNBP2 | 76404 | 76404 | Malabsorption |

OR: Odds Ratio Additional detail in Table 13.

TABLE 9

CVID Patients with GI Enteropathy vs CVID Patients without Genotype Association Replication in IBD Based on Single SNP Sigificance

| SNP | Gene | Distance | P_CVID + GIEnteropathy(IBD) | Allele1 | F_A | F_U | OR | P_IBD | Allele1 | F_A | F_U | OR |
|---|---|---|---|---|---|---|---|---|---|---|---|---|
| rs6532122 | GPRIN3 | 3497 | 0.001204 | A | 0.2632 | 0.0947 | 3.42 | 9.90E−8 | A | 0.0786 | 0.1072 | 0.7109 |
| rs17041264 | COLQ | 196 | 0.000368 | T | 0.1579 | 0.0350 | 5.17 | 3.15E−6 | T | 0.0049 | 0.0135 | 0.3608 |
| rs12889533 | C14orf143 | 19903 | 0.000561 | T | 0.1316 | 0.4156 | 0.21 | 1.28E−4 | T | 0.3563 | 0.3878 | 0.8736 | rs12889533 replicates with allele frequency in the same direction while rs6532122 and rs17041264 are significant in the opposite direction of allele frequency.

Finally, to identify potential functional biases specific to CVID, we evaluated clustering into specific INTERPRO categories using DAVID[23]: Database for Annotation, Visualization, and Integrated Discovery. We found two significant INTERPRO categories with genes contributing from several of our different analysis methods. First, "Interleukin 1/heparin-binding growth factor" P=9.60×10$^{-3}$ including FGF1, FGF23, FGF6, and FGF14 from subphenotype analysis of lymphadenopathy, cytopenias, LIP, and low IgA. Secondly, "Immunoglobulin I-set" P=5.40×10$^{-2}$ including CHL1, CNTN4, LINGO2, SDK1 from overall GWAS analysis, cytopenias subphenotype, and duplication CNV.

Discussion

CVID as a clinical phenotype was described more than 50 years ago, but aside from a small number of recessively inherited genes in a few families, and the more prevalent but poorly understood contribution of mutations in TNFRSF13B[5,6,7,24], other causes have remained obscure. CVID has thus been hypothesized to represent a diverse collection of genetic lesions resulting in a similar immunologic phehotype. The MHC region has been associated with a myriad of complex diseases[25] including immune-related conditions[26] and CVID[8,9]. MHC was robustly associated with this CVID in our study, confirming the prior work that was not performed at the genome-wide level. However, the SNP genotype association analysis presented here also revealed novel genes, with the most significant CVID associations outside of the MHC region with a locus encompassing ADAM28, ADAM7, ADAMDEC1 and STC1 (P=6.24×10$^{-6}$). The ADAM family proteins are zinc metalloproteases involved in diverse biologic processes, including immune responses. Interestingly, the metallopeptidase MMP27 was also associated with CVID (P=1.69×10$^{-4}$). Proteins of the matrix metalloproteinase (MMP) family are involved in the breakdown of extracellular matrix to promote routine physiological processes, but may also facilitate disease pathogenesis. Related genes have demonstrated immunological function involved in the regulation of cytokine release, Th2 immune responses and specific inflammatory processes. ADAM28 is also known as the lymphocyte metalloprotease MDC-L, expressed on the lymphocyte cell surface[27]. As such, it has been defined as a ligand for α4β1 integrin which enables the adhesion of other leukocytes expressing this integrin. STC1 in the same region, is a gene that encodes stanniocalcin 1 protein, involved in regulation of calcium including in antioxidant pathways of marcophages[28]. In this light, calcium regulation within immune cells has been previously identified as aberrant in certain CVID patient samples[29]. UBX10 may be a compelling candidate potentially involved in immunopathogenesis of primary antibody failure in that it encodes an Ubiquitin-like protein, which in addition to phosphorylation, has been shown to regulate NF-κB activity[30]. SDK1 (Sphingosine-dependent protein kinase-1) is important in the survival of alveolar macrophages[31]. DEPDC6 is a negative regulator of mTORC signaling pathways and RNA expression levels were found to be significantly different between those mice resistant to H5N1 influenza virus when compared to those that were susceptible[32]. No significant associations in the region of TACI were observed, and subjects with TACI mutations were not separately identified. We reviewed the reported amino acid changes and looked up their corresponding non-synonymous SNP IDs (Table 10). No imputation reference files including these SNPs were available to infer genotypes.

TABLE 10

TACI Protein TNFRSF13B Gene Amino Acid Variant and Corresponding nsSNP rs ID

| nsSNP | DNA position | Alleles | AA Change | Clinical Report (bold-in reports) |
| --- | --- | --- | --- | --- |
| rs34562254 | 16783716 | C/T | P (CCC) --> L (CTC) | P251L |
| rs72553886 | 16783732 | G/T | V (GTC) --> F (TTC) | V246F |
| rs56063729 | 16783809 | A/G | V (GTG) --> A (GCG) | V220A |
| rs56248318 | 16784408 | A/C | Q (CAG) --> H (CAT) | Q196H |
| rs72553885 | 16784417 | A/C | C (TGC) --> * (TGA) | C193X |
| rs72553883 | 16784454 | A/C | A (GCG) --> E (GAG) | A181E |
| rs72553882 | 16784504 | A/C | Y (TAC) --> * (TAA) | Y164X |
| rs72553881 | 16784541 | A/G | G (GGG) --> E (GAG) | G152E |
| rs72553880 | 16792777 | A/G | A (GCT) --> T (ACT) | A149T |
| rs72553879 | 16792911 | A/G | C (TGT) --> Y (TAT) | C104Y |
| rs34557412 | 16792912 | C/T | C (TGT) --> R (CGT) | C104R |
| rs72553877 | 16792962 | A/T | I (ATC) --> N (AAC) | I87N |
| rs72553876 | 16792986 | A/G | Y (TAT) --> C (TGT) | Y79C |
| rs55916807 | 16793007 | C/T | R (CGC) --> H (CAC) | R72H |
| rs67951770 | 16796563 | C/G | D (GAT) --> H (CAT) | D41H |
| rs67951769 | 16796563 | —/G | frameshift | D41fx |
| rs72553874 | 16796566 | C/T | W (TGG) --> R (CGG) | W40R |
| rs72553884 | 16784425-16784424 | —/G | Frameshift | D191G |
| rs72553878 | 16792925-16792924 | —/T | Frameshift | Q99H |
| rs34182967 | 16793004-16793003 | —/C | Frameshift | K73R |
| rs72553875 | 16793018-16793017 | —/A | Frameshift | S68S |

TABLE 11

Most Significant Associated Regions Based on Genotype Association

| Region Genomic Span | Gene | Count SNPs Top 1000 | Distance From Exon | BestP | BestSNP | Allele1 | F_A | F_U |
|---|---|---|---|---|---|---|---|---|
| chr6: 27236785-32521295 | MHC | 110 | 0 | 8.62E-10 | rs3117426 | T | 0.3268 | 0.1907 |
| chr8: 23746576-24681608 | ADAM28, ADAM7, ADAMDEC1, STC1 | 4 | 0 | 6.24E-6 | rs4872262 | A | 0.0391 | 0.0107 |
| chr4: 189671181-189676119 | AK095968 | 2 | 18764 | 1.78E-5 | rs1606234 | T | 0.2961 | 0.4124 |
| chr10: 73083830-73084583 | CDH23 | 2 | 7287 | 2.45E-5 | rs7087554 | A | 0.5894 | 0.4729 |
| chr7: 4270929-4287047 | SDK1 | 5 | 0 | 4.70E-5 | rs895710 | T | 0.2905 | 0.4003 |
| chr1: 20369369-20490791 | FLJ32784, UBXN10 | 7 | 0 | 9.09E-5 | rs7514144 | C | 0.2654 | 0.1808 |
| chr10: 27709830-27728115 | PTCHD3 | 7 | 0 | 9.77E-5 | rs506659 | T | 0.4022 | 0.3026 |
| chr1: 59987116-59993733 | FGGY | 2 | 2458 | 1.52E-4 | rs11207520 | G | 0.3994 | 0.3026 |
| chr12: 80435676-80444630 | PPFIA2 | 2 | 59900 | 1.63E-4 | rs2400955 | T | 0.4134 | 0.3159 |
| chr11: 102069786-102079454 | MMP27 | 2 | 0 | 1.69E-4 | rs17099394 | T | 0.1229 | 0.0687 |
| chr16: 71592439-71594134 | ZFHX3 | 2 | 40845 | 1.80E-4 | rs8056528 | C | 0.3687 | 0.2754 |
| chr8: 124729628-124734756 | KLHL38 | 4 | 0 | 2.05E-4 | rs4871402 | A | 0.0643 | 0.1325 |
| chr3: 7364204-7369287 | GRM7 | 4 | 40865 | 2.96E-4 | rs12491592 | A | 0.1536 | 0.0939 |
| chr3: 8378739-8381919 | BC020876 | 2 | 129448 | 3.51E-4 | rs359030 | C | 0.1648 | 0.1033 |
| chr6: 25570803-25574868 | LRRC16A | 2 | 0 | 3.61E-4 | rs4320355 | T | 0.3799 | 0.2898 |
| chr6: 153354039-153355207 | MTRF1L | 2 | 0 | 3.81E-4 | rs9322400 | T | 0.4469 | 0.3526 |
| chr3: 284363-285747 | CHL1 | 2 | 19083 | 4.31E-4 | rs17273893 | T | 0.148 | 0.0908 |
| chr8: 121001793-121010709 | DEPDC6 | 2 | 0 | 4.41E-4 | rs869340 | C | 0.324 | 0.2402 |
| chr2: 65518304-65520560 | FLJ16124 | 2 | 784 | 5.20E-4 | rs1194849 | G | 0.3659 | 0.4614 |
| chr21: 27713547-27722878 | BC043580 | 2 | 19690 | 5.51E-4 | rs469709 | A | 0.1704 | 0.1095 |

| Region Genomic Span | P Replication (Discovery SNP) | F_A Replication (Discovery SNP) | F_U Replication (Discovery SNP) | BestP Replication | BestSNP Replication | F_A Replication | F_U Replication |
|---|---|---|---|---|---|---|---|
| chr6: 27236785-32521295 | 0.3634 | 0.1697 | 0.1468 | 0.0004 | rs2156875 | 0.5734 | 0.4475 |
| chr8: 23746576-24681608 | 0.03135 | 0.0321 | 0.01346 | 0.0314 | rs4872262 | 0.0321 | 0.0135 |
| chr4: 189671181-189676119 | 0.4646 | 0.4266 | 0.4524 | 0.4646 | rs1606234 | 0.4266 | 0.4524 |
| chr10: 73083830-73084583 | 0.4591 | 0.5092 | 0.4829 | 0.4591 | rs7087554 | 0.5092 | 0.4829 |
| chr7: 4270929-4287047 | 0.4551 | 0.3578 | 0.3835 | 0.0235 | rs4720301 | 0.3991 | 0.4793 |
| chr1: 20369369-20490791 | 0.3018 | 0.1560 | 0.1311 | 2.25E-8 | rs6426636 | 0.4679 | 0.2857 |
| chr10: 27709830-27728115 | 0.9879 | 0.2798 | 0.2793 | 0.6291 | rs493965 | 0.2844 | 0.3001 |
| chr1: 59987116-59993733 | 0.00148 | 0.2569 | 0.1706 | 0.0015 | rs11207520 | 0.2569 | 0.1706 |
| chr12: 80435676-80444630 | 0.8687 | 0.3899 | 0.3842 | 0.5347 | rs10746192 | 0.4306 | 0.4526 |
| chr11: 102069786-102079454 | 0.6947 | 0.0734 | 0.06643 | 0.6947 | rs17099394 | 0.0734 | 0.0664 |
| chr16: 71592439-71594134 | 0.3698 | 0.3670 | 0.3368 | 0.3698 | rs8056528 | 0.367 | 0.3368 |
| chr8: 124729628-124734756 | 0.7201 | 0.1009 | 0.1088 | 0.3161 | rs7463896 | 0.1697 | 0.1979 |

TABLE 11-continued

Most Significant Associated Regions Based on Genotype Association

| | | | | | | | |
|---|---|---|---|---|---|---|---|
| chr3: 7364204-7369287 | 0.5051 | 0.0963 | 0.08318 | 0.1237 | rs7617297 | 0.3073 | 0.2592 |
| chr3: 8378739-8381919 | 0.1446 | 0.1147 | 0.08535 | 0.1139 | rs358994 | 0.1055 | 0.0754 |
| chr6: 25570803-25574868 | 0.2219 | 0.2844 | 0.2469 | 0.1896 | rs301396 | 0.445 | 0.3993 |
| chr6: 153354039-153355207 | 0.454 | 0.3945 | 0.3688 | 0.454 | rs9322400 | 0.3945 | 0.3688 |
| chr3: 284363-285747 | 0.6342 | 0.0963 | 0.08678 | 0.6342 | rs17273893 | 0.0963 | 0.0868 |
| chr8: 121001793-121010709 | 0.7402 | 0.3073 | 0.2966 | 0.682 | rs4871793 | 0.3113 | 0.2978 |
| chr2: 65518304-65520560 | 0.01381 | 0.3899 | 0.4771 | 0.0119 | rs1876518 | 0.3853 | 0.4744 |
| chr21: 27713547-27722878 | 0.9615 | 0.0963 | 0.09532 | 0.6677 | rs17631106 | 0.0688 | 0.0769 |

Bold underline: Known immunological function Gene

TABLE 12

Most Significant Associated Regions Based on CNV Association

A) Deletions

| CNVR Deletion | Count SNPs | Distance From Exon | P Deletion | Cases Del | Controls Del | Gene | MSSM | Oxford | USF | Combined |
|---|---|---|---|---|---|---|---|---|---|---|
| chr11: 85365857-85381622 | 5 | 0 | 0.01 | 2 | 0 | PICALM, PICALM variant protein | 0 | 2 | 0 | 2 |
| chr20: 57735790-57741780 | 6 | 5902 | 0.026 | 3 | 4 | PHACTR3 | 2 | 1 | 0 | 3 |
| chr22: 17396663-18417315 | 270 | 0 | 0.029 | 2 | 1 | ARVCF, C22orf25, C22orf29, CDC45L, CLDN5, CLTCL1, COMT, CR618542, CR625276, DGCR14, DGCR2, DKFZp761P1121, DKFZp781E0833, GNB1L, GP1BB, GSCL, HIRA, KIAA1647, L77561, LOC128977, MRPL40, SEPT5, SLC25A1, TBX1, TRXR2A, TSSK2, TXNRD2, U84523, UFD1, UFD1L | 2 | 0 | 0 | 2 |
| chr4: 10256682-10264316 | 4 | 2915 | 0.029 | 2 | 1 | CLNK | 0 | 1 | 1 | 2 |
| chr10: 46003146-46042543 | 8 | 0 | 0.029 | 2 | 1 | DKFZp566K0524, PTPN20A, PTPN20B | 2 | 0 | 0 | 2 |

B) Duplications

| CNVR Duplication | Count SNPs | Distance From Exon | P Dup | Cases Dup | Controls Dup | Gene | MSSM | Oxford | USF | Combined |
|---|---|---|---|---|---|---|---|---|---|---|
| chr2: 148396730-148433180 | 6 | 0 | 8.66E-16 | 15 | 0 | ACVR2A, ORC4L | 10 | 5 | 0 | 15 |
| chr15: 35053039-35063531 | 6 | 23146 | 5.72E-13 | 19 | 10 | MEIS2 | 17 | 2 | 0 | 19 |
| chr10: 53044735-53045426 | 4 | 79826 | 9.63E-13 | 12 | 0 | PRKG1 | 12 | 0 | 0 | 12 |
| chr8: 77719805-77720240 | 3 | 27377 | 1.05E-09 | 10 | 1 | BC037827 | 10 | 0 | 0 | 10 |
| chr7: 91789778-91801963 | 4 | 0 | 1.20E-09 | 12 | 4 | ANKIB1 | 9 | 3 | 0 | 3 |
| chr2: 163316298-163316595 | 3 | 17100 | 1.00E-07 | 7 | 0 | KCNH7 | 6 | 1 | 0 | 7 |
| chr7: 87180702-87191931 | 4 | 202 | 7.41E-07 | 7 | 1 | RPIB9 | 5 | 2 | 0 | 7 |
| chr12: 72825720-72832667 | 3 | 0 | 3.04E-06 | 7 | 2 | BC061638 | 7 | 0 | 0 | 7 |
| chr2: 203004035-203017311 | 5 | 20466 | 6.58E-05 | 6 | 3 | BMPR2 | 6 | 0 | 0 | 6 |
| chr19: 9256584-9277749 | 4 | 0 | 0.001 | 3 | 0 | ZNF699 | 2 | 0 | 1 | 0 |
| chr4: 39190766-39201960 | 6 | 0 | 0.004 | 3 | 1 | UGDH | 1 | 2 | 0 | 3 |

TABLE 12-continued

Most Significant Associated Regions Based on CNV Association

| | | | | | | | | | | |
|---|---|---|---|---|---|---|---|---|---|---|
| chr9: 112207473-112207708 | 3 | 553 | 0.004 | 3 | 1 | SVEP1 | 3 | 0 | 0 | 3 |
| chr7: 18903915-18905725 | 4 | 23171 | 0.009 | 3 | 2 | HDAC9 | 1 | 2 | 0 | 3 |
| chr13: 64053258-64056530 | 15 | 505114 | 0.01 | 2 | 0 | AK057471, AK098560, BC128161 | 2 | 0 | 0 | 2 |
| chr14: 35408995-35422074 | 5 | 0 | 0.01 | 2 | 0 | BRMS1L | 0 | 2 | 0 | 2 |
| chr5: 170531269-170536993 | 4 | 374 | 0.01 | 2 | 0 | DKFZp666P032, RANBP17 | 1 | 1 | 0 | 2 |
| chr4: 91413829-91415037 | 3 | 33381 | 0.01 | 2 | 0 | KIAA1680, MGC48628 | 2 | 0 | 0 | 2 |
| chr7: 34685030-34686172 | 4 | 4517 | 0.01 | 2 | 0 | AAA1, NPSR1 | 1 | 1 | 0 | 2 |
| chr3: 176427638-176429297 | 7 | 5118 | 0.01 | 2 | 0 | NAALADL2 | 2 | 0 | 0 | 2 |
| chr1: 170400944-170403742 | 4 | 26274 | 0.01 | 2 | 0 | DNM3 | 0 | 1 | 1 | 2 |
| chr2: 167031393-167045981 | 4 | 0 | 0.01 | 2 | 0 | Na+ channel, SCN7A | 2 | 0 | 0 | 2 |
| chr9: 28683005-28687679 | 3 | 21420 | 0.01 | 2 | 0 | LINGO2 | 2 | 0 | 0 | 2 |
| chr9: 105860023-105868928 | 9 | 27434 | 0.01 | 2 | 0 | OR13C3, OR13C4, OR13C5, OR13C8, OR13F1, SMC2, hCAP-E | 2 | 0 | 0 | 2 |

TABLE 13

Most Significant Associated Regions Based on Subphenotype Genotype Association

| Significant Region | P-value | SNP | A1 | F_A | F_U | OR | Count SNPs | Gene | Distance | Distance From Exon |
|---|---|---|---|---|---|---|---|---|---|---|
| A) Cancer | | | | | | | | | | |
| chr14: 23168471-23169215 | 4.57E−7 | rs222723 | C | 0.6154 | 0.1968 | 6.531 | 2 | DHRS2 | 0 | 0 |
| chr6: 140225308-140225386 | 1.53E−6 | rs12111348 | T | 0.4231 | 0.1064 | 6.157 | 2 | BC039503 | 2009 | 2009 |
| B) Lymphoma | | | | | | | | | | |
| chrX: 132092989-132095451 | 5.50E−10 | rs5977837 | C | 0.2778 | 0.02174 | 17.31 | 2 | TFDP3 | 82912 | 82912 |
| chr10: 58755852-58767334 | 1.36E−9 | rs16910534 | T | 0.2222 | 0.01383 | 20.37 | 3 | IPMK | 858286 | 858286 |
| chr7: 90245135-90245280 | 1.69E−8 | rs975004 | G | 0.3333 | 0.03953 | 12.15 | 2 | KIAA0834, PFTK1 | 0 | 12544 |
| chr5: 156402979-156407976 | 3.62E−8 | rs10038271 | T | 0.7222 | 0.1877 | 11.25 | 2 | HAVCR1 | 0 | 651 |
| chr1: 55704352-55706323 | 2.85E−7 | rs356086 | G | 0.1111 | 0.003953 | 31.5 | 2 | FLJ45337 | 112975 | 112975 |
| chr1: 106430611-106438079 | 1.55E−6 | rs11184786 | T | 0.3333 | 0.05336 | 8.87 | 2 | BC043293 | 467531 | 467531 |
| C) Lymphadenopathy | | | | | | | | | | |
| chrX: 53035117-53039801 | 1.90E−7 | rs10127016 | G | 0.3833 | 0.125 | 4.351 | 2 | TMEM29 | 0 | 1409 |
| chr12: 30583074-30598457 | 4.82E−7 | rs1905675 | C | 0.2 | 0.5453 | 0.2085 | 2 | IPO8 | 74732 | 74732 |
| chr14: 64723761-64783067 | 8.09E−7 | rs4299072 | A | 0.1667 | 0.02802 | 6.938 | 4 | BX161428 | 0 | 0 |
| chr5: 141916656-141926115 | 1.13E−6 | rs17706715 | A | 0.2333 | 0.05603 | 5.127 | 2 | FGF1 | 27191 | 27191 |
| chr11: 101265604-101266102 | 1.55E−6 | rs17097290 | T | 0.15 | 0.02371 | 7.267 | 2 | ANGPTL5 | 513 | 513 |
| D) Nodular regenerative hyperplasia of the liver (NRH) | | | | | | | | | | |
| chr1: 68153970-68161019 | 2.29E−10 | rs1926283 | C | 0.2308 | 0.01807 | 16.3 | 3 | AK096081, AK124028 | 0 | 33408 |
| chr21: 18188480-18192815 | 2.84E−7 | rs7280675 | G | 0.1923 | 0.02008 | 11.62 | 2 | CHODL | 2636 | 2636 |
| chr21: 45476504-45476918 | 3.23E−7 | rs4592938 | A | 0.1154 | 0.006024 | 21.52 | 2 | C21orf89 | 1777 | 1777 |
| chr8: 143046590-143055893 | 1.18E−6 | rs12676273 | G | 0.3462 | 0.07229 | 6.794 | 3 | TSNARE1 | 235455 | 235455 |

TABLE 13-continued

Most Significant Associated Regions Based on Subphenotype Genotype Association

| Significant Region | P-value | SNP | A1 | F_A | F_U | OR | Count SNPs | Gene | Distance | Distance From Exon |
|---|---|---|---|---|---|---|---|---|---|---|
| chrX: 27453340-27462759 | 1.29E−6 | rs5971431 | C | 0.3077 | 0.05823 | 7.188 | 3 | AK057304 | 55692 | 55692 |
| E) LIP | | | | | | | | | | |
| chr13: 101641990-101673539 | 5.76E−8 | rs1336698 | G | 0.65 | 0.168 | 9.197 | 6 | FGF14 | 0 | 69139 |
| chrX: 143116309-143119321 | 6.77E−8 | rs6649722 | A | 0.3 | 0.0377 | 10.94 | 3 | UBE2NL | 320286 | 320286 |
| chrX: 47642545-47651320 | 7.70E−8 | rs12387999 | A | 0.2 | 0.016 | 15.38 | 2 | ZNF81 | 0 | 2262 |
| chr2: 109118795-109120561 | 4.62E−7 | rs375099 | C | 0.25 | 0.02976 | 10.87 | 2 | POSH2 | 0 | 5794 |
| chrX: 30122360-30125674 | 2.52E−6 | rs5927496 | C | 0.7 | 0.2341 | 7.633 | 2 | MAGEB2 | 17927 | 17927 |
| F) Bronchiectasis | | | | | | | | | | |
| chrX: 22422160-22428888 | 5.71E−8 | rs5925651 | A | 0.3462 | 0.1386 | 3.291 | 3 | ZNF645 | 219665 | 219665 |
| chr2: 200959722-201175137 | 2.39E−6 | rs13019534 | G | 0.5064 | 0.2908 | 2.503 | 2 | AOX1, DNAPTP6, KCTD18, SGOL2 | 0 | 0 |
| chr8: 15782386-15788801 | 2.92E−6 | rs1563297 | A | 0.5321 | 0.3152 | 2.47 | 2 | TUSC3 | 116020 | 116020 |
| chr19: 51765478-51768118 | 6.30E−6 | rs6509286 | C | 0.4167 | 0.2228 | 2.491 | 2 | AK094504 | 0 | 27862 |
| chrX: 68569536-68573727 | 1.04E−5 | rs7056340 | A | 0.3141 | 0.1467 | 2.663 | 2 | TMEM28 | 68076 | 68076 |
| chr6: 32508322-32510683 | 1.12E−5 | rs2027856 | T | 0.02564 | 0.163 | 0.1351 | 2 | HLA-DRA | 4942 | 4942 |
| G) Granuloma | | | | | | | | | | |
| chr11: 12182328-12186013 | 4.83E−6 | rs16910765 | T | 0.2206 | 0.05921 | 4.497 | 3 | KIAA0750, MICAL2, MICAL2PV1, MICAL2PV2 | 0 | 0 |
| chr1: 33674005-33683227 | 1.26E−5 | rs12751162 | A | 0.3824 | 0.1601 | 3.248 | 2 | PHC2 | 4803 | 4803 |
| chr6: 88453628-88454474 | 2.04E−5 | rs2250276 | G | 0.1765 | 0.04386 | 4.671 | 2 | AKIRIN2 | 0 | 5428 |
| chrX: 27453340-27462759 | 3.18E−5 | rs5971431 | C | 0.1912 | 0.05263 | 4.255 | 2 | AK057304 | 55692 | 55692 |
| H) GI Enteropathy | | | | | | | | | | |
| chr12: 2531014-2538733 | 1.21E−7 | rs4765961 | C | 0.4737 | 0.142 | 5.439 | 3 | CACNA1C | 0 | 0 |
| chr10: 26643326-26646318 | 2.90E−6 | rs7903552 | G | 0.3684 | 0.107 | 4.869 | 2 | GAD2 | 9833 | 9833 |
| chr5: 11592622-11597026 | 6.26E−6 | rs2727602 | T | 0.6053 | 0.2613 | 4.334 | 2 | CTNND2 | 0 | 21030 |
| chr21: 42551877-42552623 | 9.95E−6 | rs3787986 | T | 0.3684 | 0.1152 | 4.479 | 4 | ABCG1 | 0 | 0 |
| chr9: 4033590-4039110 | 1.13E−5 | rs676472 | C | 0.2895 | 0.07613 | 4.944 | 3 | GLIS3 | 0 | 68391 |
| chr4: 33014145-33017023 | 1.43E−5 | rs6846113 | A | 0.1053 | 0.01029 | 11.32 | 2 | AK093205 | 552926 | 552926 |
| I) Malabsorption | | | | | | | | | | |
| chr20: 55901032-55985359 | 3.21E−9 | rs8124301 | T | 0.4231 | 0.07631 | 8.877 | 5 | C20orf85 | 174030 | 174030 |
| chr7: 117377201-117382435 | 9.94E−7 | rs17140937 | C | 0.2692 | 0.04418 | 7.971 | 2 | CTTNBP2 | 76404 | 76404 |
| chr11: 124071934-124079438 | 1.25E−6 | rs1784539 | G | 0.6154 | 0.2068 | 6.136 | 2 | SPA17 | 2037 | 2037 |
| chr10: 30255454-30255817 | 5.18E−6 | rs11007812 | T | 0.3077 | 0.06426 | 6.472 | 2 | CR626438 | 85918 | 85918 |
| chr12: 31276546-31281817 | 6.76E−6 | rs12819069 | C | 0.3846 | 0.09839 | 5.727 | 2 | OVOS2 | 26191 | 26191 |
| chr8: 6374232-6376048 | 8.56E−6 | rs2515477 | T | 0.4231 | 0.1185 | 5.456 | 2 | ANGPT2, MCPH1 | 0 | 1213 |
| J) Splenectomy | | | | | | | | | | |
| chr9: 130092787-130095025 | 1.03E−6 | rs7026795 | A | 0.425 | 0.1802 | 3.363 | 2 | C9orf119 | 1698 | 1698 |
| chr3: 72044083-72052222 | 1.11E−6 | rs7648163 | C | 0.55 | 0.2748 | 3.226 | 2 | AK097190 | 115138 | 115138 |
| chr1: 73821234-73888127 | 2.23E−6 | rs4606267 | G | 0.325 | 0.1194 | 3.552 | 3 | BC041341 | 244086 | 244086 |

TABLE 13-continued

Most Significant Associated Regions Based on Subphenotype Genotype Association

| Significant Region | P-value | SNP | A1 | F_A | F_U | OR | Count SNPs | Gene | Distance | Distance From Exon |
|---|---|---|---|---|---|---|---|---|---|---|
| chr9: 70762083-70815910 | 2.46E−6 | rs2993008 | T | 0.225 | 0.06306 | 4.313 | 2 | AK057188, PIP5K1B | 0 | 0 |
| chr8: 137069094-137070609 | 3.13E−6 | rs6985828 | C | 0.0625 | 0.002252 | 29.53 | 2 | KHDRBS3 | 340064 | 340064 |
| chr15: 66415767-66419741 | 3.78E−6 | rs6494736 | C | 0.175 | 0.04054 | 5.02 | 2 | ITGA11 | 0 | 0 |
| chr7: 141314419-141314653 | 2.60E−5 | rs11761774 | A | 0.475 | 0.2455 | 2.781 | 2 | TAS2R38 | 4247 | 4247 |
| K) Cytopenias | | | | | | | | | | |
| chr12: 3711033-4573405 | 4.28E−6 | rs241964 | C | 0.6111 | 0.3 | 3.667 | 6 | C12orf4, C12orf5, CCND2, DYRK4, EFCAB4B, FGF23, FGF6, PARP11, RAD51AP1 | 0 | 0 |
| chr8: 2721609-2723174 | 3.52E−5 | rs341672 | C | 0.2593 | 0.0812 | 3.961 | 2 | CSMD1, KIAA1890 | 59615 | 59615 |
| chr3: 2628577-2629597 | 0.000337 | rs1020997 | G | 0.2407 | 0.4979 | 0.3198 | 2 | CNTN4 | 0 | 40335 |
| chr2: 1783619-1783961 | 0.000426 | rs6548056 | G | 0.1852 | 0.434 | 0.2963 | 2 | MYT1L | 0 | 514 |
| chr11: 2240035-2241166 | 0.000533 | rs17659078 | A | 0.4444 | 0.2286 | 2.699 | 2 | ASCL2 | 5138 | 5138 |
| chr10: 1236883-1237022 | 0.000603 | rs10794730 | T | 0.4815 | 0.2596 | 2.649 | 2 | ADARB2 | 0 | 583 |
| chr9: 1588885-1595735 | 0.000866 | rs1923928 | T | 0.1852 | 0.4191 | 0.315 | 2 | SMARCA2 | 409607 | 409607 |
| chr1: 4222578-4225577 | 0.000884 | rs966321 | C | 0.2593 | 0.4979 | 0.353 | 2 | AX748168 | 146394 | 146394 |
| L) organ specific autoimmunity (OSAI) | | | | | | | | | | |
| chr8: 101728102-101728344 | 6.89E−8 | rs7815950 | G | 0.2133 | 0.05615 | 4.559 | 2 | SNX31 | 0 | 2334 |
| chrX: 39933689-39956544 | 5.18E−7 | rs2948491 | A | 0.18 | 0.04545 | 4.61 | 4 | BCOR | 12163 | 12163 |
| chr3: 109180117-109186346 | 6.27E−6 | rs709477 | A | 0.2733 | 0.4893 | 0.3926 | 2 | BC101231 | 50156 | 50156 |
| chr1: 37438130-37446852 | 6.96E−6 | rs6426015 | A | 0.2667 | 0.1096 | 2.953 | 3 | GRIK3 | 165699 | 165699 |
| chr15: 84701881-84720707 | 1.19E−5 | rs1431234 | C | 0.3 | 0.5108 | 0.4105 | 2 | AGBL1 | 0 | 20894 |
| M) Low IgM (<50 mg/dL) | | | | | | | | | | |
| chr1: 25735669-25753653 | 6.02E−8 | rs2065970 | G | 0.06553 | 0.2411 | 4.529 | 5 | LDLRAP1 | 0 | 0 |
| chr4: 59393803-59398745 | 1.77E−5 | rs2899130 | A | 0.2257 | 0.4286 | 2.573 | 2 | BC034799 | 1366894 | 1366894 |
| chr5: 76127981-76128963 | 2.17E−5 | rs615986 | T | 0.4927 | 0.2679 | 0.3767 | 2 | F2RL1 | 21647 | 21647 |
| N) Low IgA (<10 mg/dL) | | | | | | | | | | |
| chrX: 30733771-30736604 | 1.44E−7 | rs11095197 | T | 0.1469 | 0.3431 | 3.034 | 2 | MAP3K7IP3 | 18876 | 18876 |
| chrX: 145696682-145751200 | 3.48E−6 | rs6626815 | C | 0.5656 | 0.3578 | 0.4279 | 5 | CXorf1 | 977620 | 977620 |
| chr15: 47024768-47025722 | 6.75E−6 | rs17469978 | C | 0.2313 | 0.4167 | 2.375 | 2 | SHC4 | 0 | 16198 |
| chrX: 32356174-32388539 | 1.25E−5 | rs699457 | G | 0.2656 | 0.1078 | 0.3342 | 2 | DMD | 0 | 0 |
| chr1: 3915418-3917931 | 2.69E−5 | rs10737395 | A | 0.1 | 0.2353 | 2.769 | 2 | AK124708 | 236 | 236 |
| chr13: 101257602-101258342 | 3.22E−5 | rs1322702 | A | 0.04375 | 0.1471 | 3.768 | 2 | FGF14 | 0 | 60734 |
| O) Low B cells (CD19+ cells <1%) | | | | | | | | | | |
| chr8: 13834782-13842376 | 7.62E−8 | rs2682665 | C | 0.1818 | 0.01394 | 15.71 | 3 | SGCZ | 149368 | 149368 |
| chr7: 107306707-107314113 | 2.16E−7 | rs9690688 | A | 0.3636 | 0.06375 | 8.393 | 2 | DLD | 4709 | 4709 |
| chr9: 33103066-33103970 | 1.40E−6 | rs12379501 | T | 0.3182 | 0.05578 | 7.9 | 2 | B4GALT1 | 0 | 0 |
| chr13: 37798435-37846851 | 2.25E−6 | rs4943583 | G | 0.2273 | 0.02988 | 9.549 | 7 | UFM1 | 0 | 0 |

TABLE 13-continued

Most Significant Associated Regions Based on Subphenotype Genotype Association

| Significant Region | P-value | SNP | A1 | F_A | F_U | OR | Count SNPs | Gene | Distance | Distance From Exon |
|---|---|---|---|---|---|---|---|---|---|---|
| P) Young age of symptom onset (<10 yrs) | | | | | | | | | | |
| chrX: 152295068-152303019 | 9.84E−8 | rs5987017 | A | 0.2143 | 0.04773 | 5.442 | 4 | ZNF275 | 24829 | 24829 |
| chrX: 37803525-37832251 | 1.54E−7 | rs5918500 | C | 0.4878 | 0.2123 | 3.533 | 3 | SYTL5 | 0 | 0 |
| chr19: 7505735-7508421 | 2.31E−6 | rs604959 | C | 0.4762 | 0.2273 | 3.091 | 2 | PNPLA6 | 0 | 0 |

The CNV association analysis also uncovered novel genes associated with either the immunopathogenesis of antibody deficiency or the development of specific complications of CVIDs. In fact, 84 CNV deletions and 98 duplications were identified in one or more CVID patients but were not found in any controls. Most were intra-exonic and thus likely to exert impact. Some of the genes potentially affected by the identified CNV were also discovered in the GWAS part of this study. Many others have direct or potential relevance to the immune system and many were unique to individual patients, thus underscoring the great mechanistic diversity that is likely to underlie this collection of disorders, also reflected in the variability in clinical presentation and disease natural history[1]. Among those, we noted a highly significant number of subjects with duplications in ORC4L, a gene previously associated with B-Cell lymphoproliferative disorders[33]. This gene is essential for initiation of DNA replication, and potentially in rapidly proliferating immune cells.

We then performed a SNP genotype association to the particular features of CVID to define potential common mechanistic threads amongst the specific clinical and immunological variants to enable the prediction of CVID clinical phenotypes. Significant individual associations were made with all CVID variables studied (Table 8) including cancer (1), lymphoma (5), lymphadenopathy (3), NRH (3), LIP (4), bronchiectasis (1), granulomatous disease (0), enteropathy (1), malabsorption (2), splenomegaly (0), cytopenias (0), autoimmunity (2), low IgM (1), low IgA (1), low B cells (2), and early age of onset (2). In this regard, PFTK1 is a member of the CDC2-related protein kinase family found constitutively expressed at high levels in B cell lymphomas[34], and also found associated with lymphoma in the studied subjects with this complication. Interestingly, HAVCR1, allele frequency also found enriched in the same subjects, plays a role in Th cell development and the regulation of asthma and allergic diseases[35]. FGF14, associated with LIP and low IgA, is a member of the fibroblast growth factor (FGF) family, which has crucial roles in embryonic development, cell growth, morphogenesis, tissue repair, tumor growth and invasion[36]. SNX31, associated with organ-specific autoimmunity, is a sorting nexin which may be involved in protein trafficking; SNX family proteins are subunits required for CD28 mediated T cell costimulation[37]. LDLRAP1, associated with lower serum IgM, encodes a cytosolic protein which contains a phosphotyrosine binding (PTD) domain which interacts with the cytoplasmic tail of the LDL receptor, and is associated with hypercholesterolaemia. In addition to the potential of these findings to provide mechanistic insight into how these subphenotypes arise, they may also allow for the prediction of associated comorbidity at the time of diagnosis. This has the potential to greatly improve the clinical management of the CVIDs.

REFERENCES

1. Chapel H, Cunningham-Rundles C. Update in understanding common variable immunodeficiency disorders (CVIDs) and the management of patients with these conditions. Br J Haematol. 2009 June; 145(6): 709-27. Epub 2009 Mar. 30.
2. Cunningham-Rundles C, Bodian C. Common Variable Immunodeficiency: Clinical and Immunological Features of 248 Patients Clinical Immunology Volume 92, Issue 1, July 1999, Pages 34-48.
3. Wehr C et al. The EUROclass trial: defining subgroups in common variable immunodeficiency. Blood. 2008 Jan. 1; 111(1):77-85. Epub 2007 Sep. 26.
4. Bacchelli C, Buckridge S, Thrasher A J, Gaspar H B. Translational mini-review series on immunodeficiency: molecular defects in common variable immunodeficiency. Clin Exp Immunol 2007 September; 149(3):401-9.
5. Salzer U et al. Mutations in TNFRSF13B encoding TACI are associated with common variable immunodeficiency in humans. Nat Genet. 2005 August; 37(8):820-8.
6. Castigli E et al. TACI is mutant in common variable immunodeficiency and IgA deficiency. Nat Genet. 2005 August; 37(8):829-34.
7. Pan-Hammarström Q, et al Reexamining the role of TACI coding variants in common variable immunodeficiency and selective IgA deficiency. Nat Genet. 2007 April; 39(4):429-30.
8. Volanakis J E et al. Major histocompatibility complex class III genes and susceptibility to immunoglobulin A deficiency and common variable immunodeficiency. J Clin Invest. 1992 June; 89(6):1914-22.
9. Olerup O, Smith C I, Björkander J, Hammarström L. Shared HLA class II-associated genetic susceptibility and resistance, related to the HLA-DQB1 gene, in IgA deficiency and common variable immunodeficiency. Proc Natl Acad Sci USA. 1992 Nov. 15; 89(22):10653-7.
10. Grimbacher B et al. Homozygous loss of ICOS is associated with adult-onset common variable immunodeficiency Nature Immunology 4, 261-268 (2003).
11. Salzer U et al. ICOS deficiency in patients with common variable immunodeficiency Clinical Immunology. Volume 113, Issue 3, December 2004, Pages 234-240.
12. van Zelm M C et al. CD81 gene defect in humans disrupts CD19 complex formation and leads to antibody deficiency. J Clin Invest. 2010 April; 120(4):1265-74. doi: 10.1172/JCI39748. Epub 2010.

13. van Zelm M C et al. An antibody-deficiency syndrome due to mutations in the CD19 gene. N Engl J Med. 2006 May 4; 354(18):1901-12.
14. Kanegane H et al. Novel mutations in a Japanese patient with CD19 deficiency. Genes and Immunity (2007) 8, 663-670; doi:10.1038/sj.gene.6364431; published online 20 Sep. 2007.
15. Kuijpers T W, et al. J Clin Invest. 2010 January; 120(1):214-22. Epub 2009 Dec. 21. CD20 deficiency in humans results in impaired T cell-independent antibody responses.
16. Conley M E, Notarangelo L D, Etzioni A. Diagnostic criteria for primary immunodeficiencies. Representing PAGID (Pan-American Group for Immunodeficiency) and ESID (European Society for Immunodeficiencies). Clin Immunol. 1999 December; 93(3):190-7.
17. Price A L et al. Principal components analysis corrects for stratification in genome-wide association studies. Nat Genet. 2006 August; 38(8):904-9. Epub 2006 Jul. 23.
18. Purcell S et al. PLINK: a toolset for whole-genome association and population-based linkage analysis. American Journal of Human Genetics, 81 (2007).
19. Imielinski M, Baldassano R N, Griffiths A et al.: Common variants at five new loci associated with early-onset inflammatory bowel disease. Nat. Genet. 41,1335-1340 (2009).
20. Wang, K. et al. PennCNV: an integrated hidden Markov model designed for high-resolution copy number variation detection in whole-genome SNP genotyping data. *Genome Res.* 17, 1665-1674 (2007).
21. Bucan M et al. Genome-wide analyses of exonic copy number variants in a family-based study point to novel autism susceptibility genes. PLoS Genet. 2009 June; 5(6):e1000536. Epub 2009 Jun. 26.
22. Chapel H et al. Common variable immunodeficiency disorders: division into distinct clinical phenotypes. Blood. 2008 Jul. 15; 112(2):277-86. Epub 2008 Mar. 4.
23. Dennis G, Jr, et al. (2003) DAVID: Database for Annotation, Visualization, and Integrated Discovery. Genome Biol 4:3.
24. Zhang L et al. Transmembrane activator and calcium-modulating cyclophilin ligand interactor mutations in common variable immunodeficiency: clinical and immunologic outcomes in heterozygotes. J Allergy Clin Immunol. 2007 November; 120(5): 1178-85.
25. Shiina T, Inoko H, Kulski J K. An update of the HLA genomic region, loci information and disease associations. *Tissue Antigens* 2004, 64:631-649.
26. International MHC and Autoimmunity Genetics Network et al. Mapping of multiple susceptibility variants within the MHC region for 7 immune-mediated diseases. Proc Natl Acad Sci USA. 2009 Nov. 3; 106(44):18680-5.
27. Bridges L C et al. The lymphocyte metalloprotease MDC-L (ADAM 28) is a ligand for the integrin alpha4beta1. J Biol Chem. 2002 Feb. 1; 277(5):3784-92. Epub 2001 Nov. 27.
28. Sheikh-Hamad D. Mammalian stanniocalcin-1 activates mitochondrial antioxidant pathways: new paradigms for regulation of macrophages and endothelium. Am J Physiol Renal Physiol. 2010 February; 298(2): F248-54. Epub 2009 Aug. 5.
29. Foerster C. et al. B Cell Receptor-Mediated Calcium Signaling Is Impaired in B Lymphocytes of Type Ia Patients with Common Variable Immunodeficiency. J Immunol 2010.
30. Karin M, Ben-Neriah Y. Phosphorylation Meets Ubiquitination: The Control of NF-κB Activity. Annual Review of Immunology Vol. 18: 621-663 (April 2000).
31. Monick M M et al. Cooperative prosurvival activity by ERK and Akt in human alveolar macrophages is dependent on high levels of acid ceramidase activity. J Immunol. 2004 Jul. 1; 173(1):123-35.
32. Boon A C et al. Host genetic variation affects resistance to infection with a highly pathogenic H5N1 influenza A virus in mice. J Virol. 2009 October; 83(20):10417-26. Epub 2009 Aug. 12.
33. Radojkovic M et al. Novel ORC4L Gene Mutation in B-Cell Lymphoproliferative Disorders The American Journal of the Medical Sciences: 2009—Volume 338—Issue 6—pp 527-529.
34. Saltis M and Davidson W. CDC2-related kinase and metabolic regulation in B cell malignancies. *The Journal of Immunology*, 2007, 178, 49.19.
35. Umetsu S E et al. TIM-1 induces T cell activation and inhibits the development of peripheral tolerance. Nat Immunol. 2005 May; 6(5):447-54. Epub 2005 Mar. 27.
36. Broadley K N et al. Monospecific antibodies implicate basic fibroblast growth factor in normal wound repair. Lab Invest. 1989 November; 61(5):571-5.
37. Badour K et al. Interaction of the Wiskott-Aldrich syndrome protein with sorting nexin 9 is required for CD28 endocytosis and cosignaling in T cells. Proc Natl Acad Sci USA. 2007 Jan. 30; 104(5):1593-8. Epub 2007 Jan. 22.
38. Bonilla F A et al. Practice parameter for the diagnosis and management of primary immunodeficiency. Ann Allergy Asthma Immunol. 2005 May; 94(5 Suppl 1):S1-63.
39. Yong P L, Orange J S, Sullivan K E. Pediatric common variable immunodeficiency: Immunologic and phenotypic associations with switched memory B cells. Pediatr Allergy Immunol. 2010 Mar. 19.

Example 2

Prediction of CVID Status and Development of Complications Based on a Targeted SNP Panels A Support Vector Machine (SVM) is a decision-based prediction algorithm which can classify data into several groups. SVM is based on training data mapped to a higher dimensional space and separated by a plane defining the two classes of data, followed by a testing stage where status is predicted based on the model and compared to known status to test the accuracy (V. Vapnik. The Nature of Statistical Learning Theory. Springer-Verlag, New York, NY, 1995). The implementation of SVM used is LIBSVM software (Chih-Chung Chang and Chih-Jen Lin, LIBSVM: a library for support vector machines, 2001. Software available at http://www.csie.ntu.du.tw/~cjlin/libsvm; C. W. Hsu, C. C. Chang, C. J. Lin. A practical guide to support vector classification, 2003). Genome-wide SNP microarrays provide 610,000 genotypes which tag the genome in an unbiased way without need for prior hypothesis concerning candidate genes. Classical genome-wide association methods evaluate single SNP significance for difference in allele frequency. Although successful, the reality that many common complex diseases are polygenic in etiology with epistasis of multiple gene combinations makes an integrative model utilizing more of the data content more incisive. The application of SVM to genome-wide SNP data provides a robust framework for clinical disease prediction to evaluate risk and enact preventative measures, as we have demonstrated previously for type 1 diabetes (Wei Z, et al., From disease association to risk assessment: an optimistic view from genome-wide association studies on type 1 diabetes. PLoS Genet. 2009 October; 5(10):e1000678. Epub 2009 Oct. 9).

There are two components to the data: the target value which is the classification of the subject and the corresponding attributes which are more granular characteristics. In the application to CVID, we sought to predict target Values (Class Labels): CVID (yes/no), Bronchiectasis (yes/no), and OSAI (yes/no). This prediction is based on the attributes (features or observed variables): Genotypes for the top 1,000 SNPs previously identified from case:control genome-wide association (top 0.16% of original data set and all P<0.0015).

Figure 6:
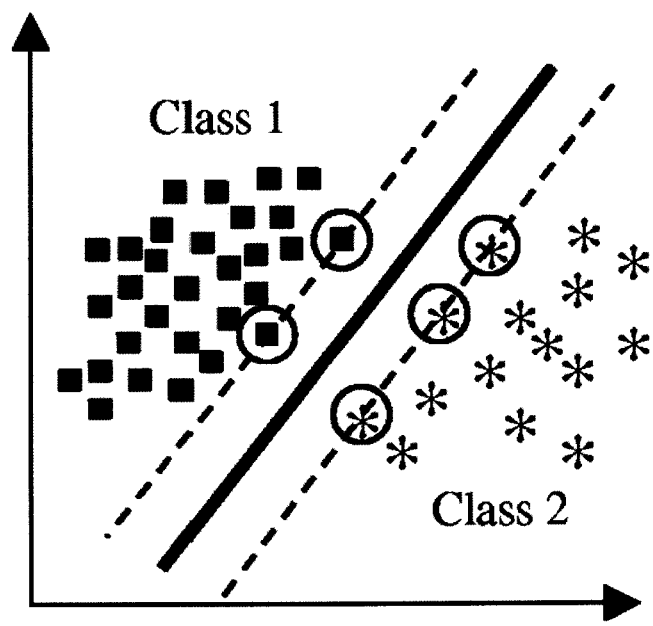
FIG. 6. Schematic Representation of Observed Data with Classification Divided by a Hyperplane. Binary SVM selects a hyperplane (bold line) that maximizes the width of the 'gap' (margin) between the two classes. The hyperplane is specified by 'boundary' training instances, called support vectors shown with circles. New cases are classified based on which side of the hyperplane they are mapped.

Phenotype labels were scaled to +1 for affected and −1 for unaffected. Genotype data is scaled with AA=0, AB=0.5 and BB=1. Data is mapped to high dimensional space by the LIBSVM algorithm to differentiate populations. Iterations of a coarse grid are followed by finer grids to avoid excessive time expenditure of complete grid search. The SVM is based principally on two variables: cost C (the penalty parameter of SVMs) and $\gamma=1$/number of variables. The SVM type in our application was C-SVM classification which runs through iterations of minimizing error functions while maintaining a hyperplane with maximum margin to avoid overfitting (FIG. 6). The kernal function maps attribute data into a higher dimensional space to improve distinguishing characteristics. The kernel type in this application was a radial basis function (RBF) which is based on distance from an origin. Once the SVM model is established through training and validated for accuracy with an independent dataset in testing, additional data can be mapped and prediction made based on the model.

Figure 7:
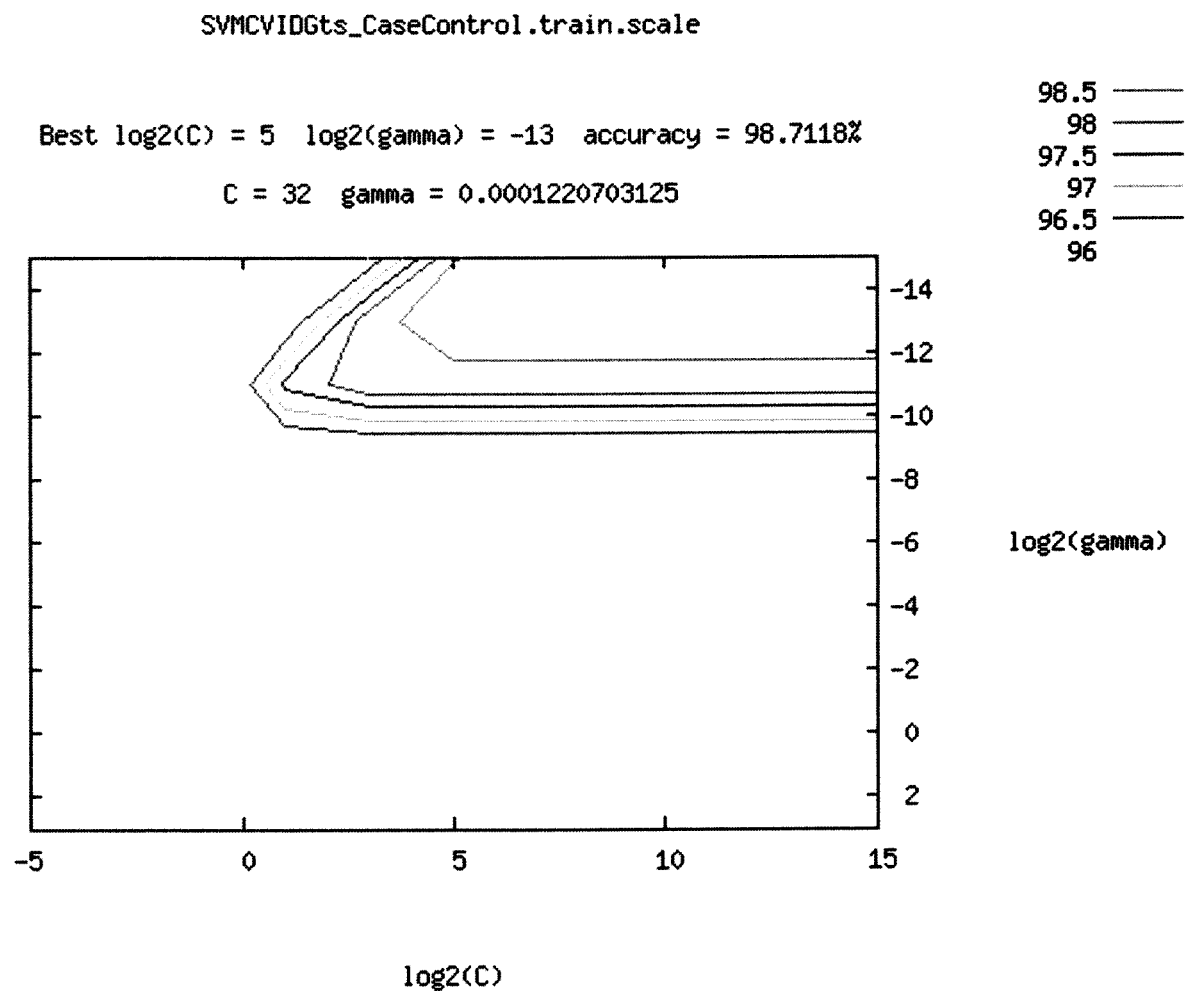
FIG. 7. SVM Model for CVID Case vs. individual not affected by CVID.

The Support vector machine (SVM) approach is a machine learning approach that can map combinations of genotypes in high dimensional space. The top 1000 significant SNPs from the discovery and replication case:control genotype association studies we used as observed characteristics to form a designation decision between CVID (common variable immunodeficiency) case and an individual not affected by CVID (Table 14). The dataset available was separated into a training set of 179 cases and 1,917 controls which the SVM model is based on. In this training set, the case/control label and genotype attributes guide model formation. In the testing set of independent 109 cases and 1,114 controls, only the genotype attributes are supplied to the model established during training which then distinguishes cases or controls based on the genotype profile. The simple diagnostic yes or no question is: based on this person's genotypes do they have CVID? The prediction accuracy turned out well: training data: 98.7% and testing data: 90.5% (FIG. 7).

Figure 8:
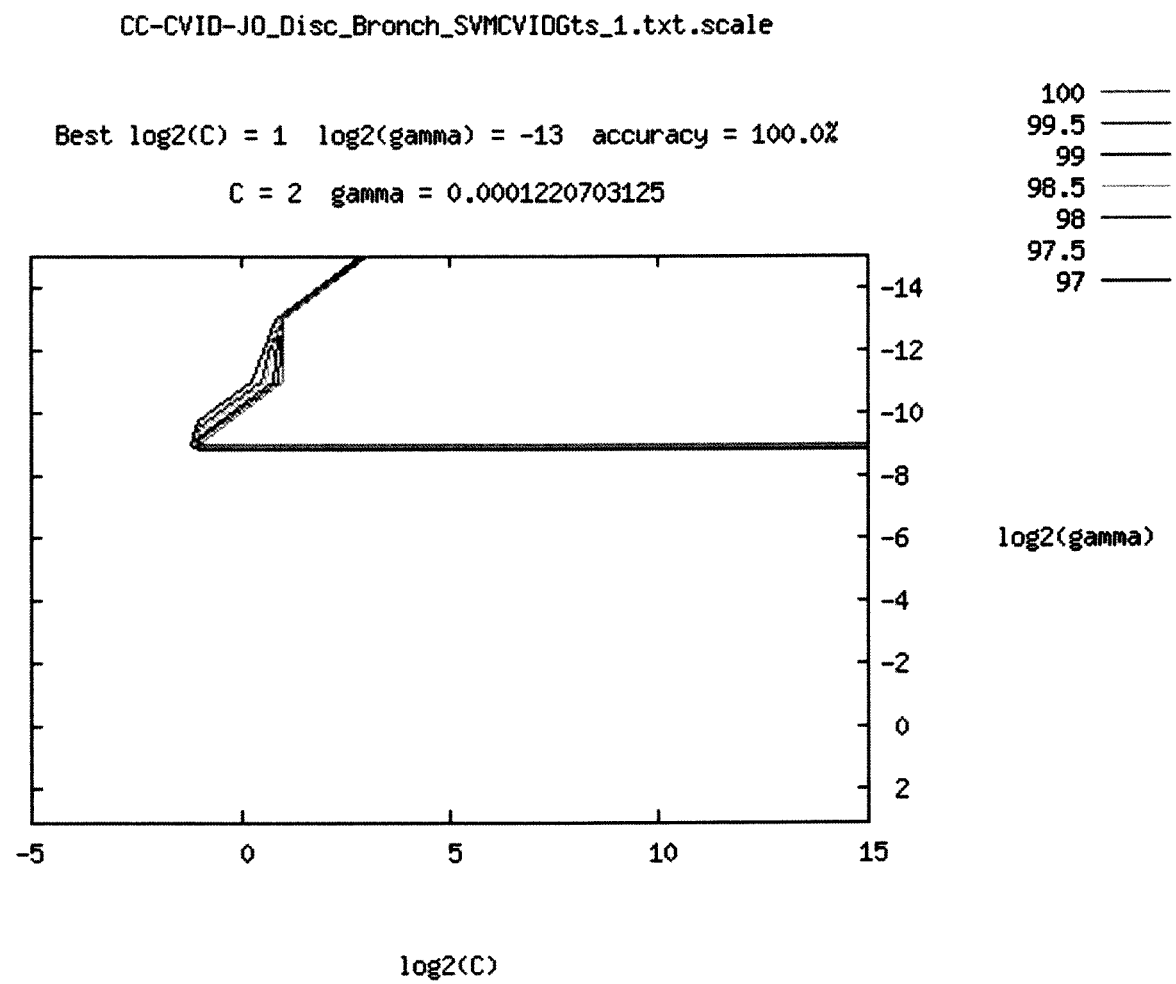
FIG. 8. SVM Model for CVID case with Bronchiectasis versus CVID case without Bronchiectasis.
Figure 9:
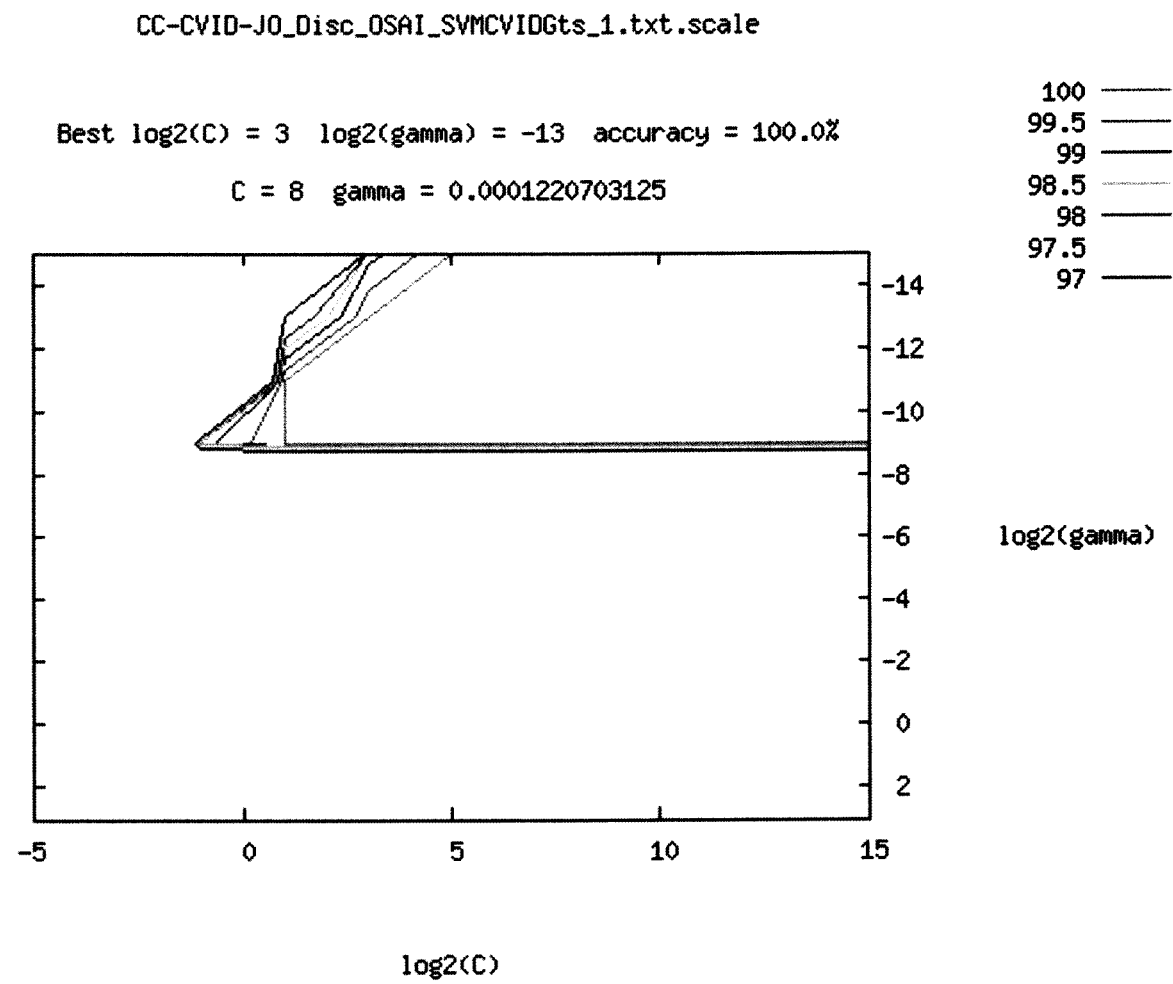
FIG. 9. SVM Model for CVID case with OSAI (organ specific autoimmunity) versus CVID case without OSAI.
Figure 10:
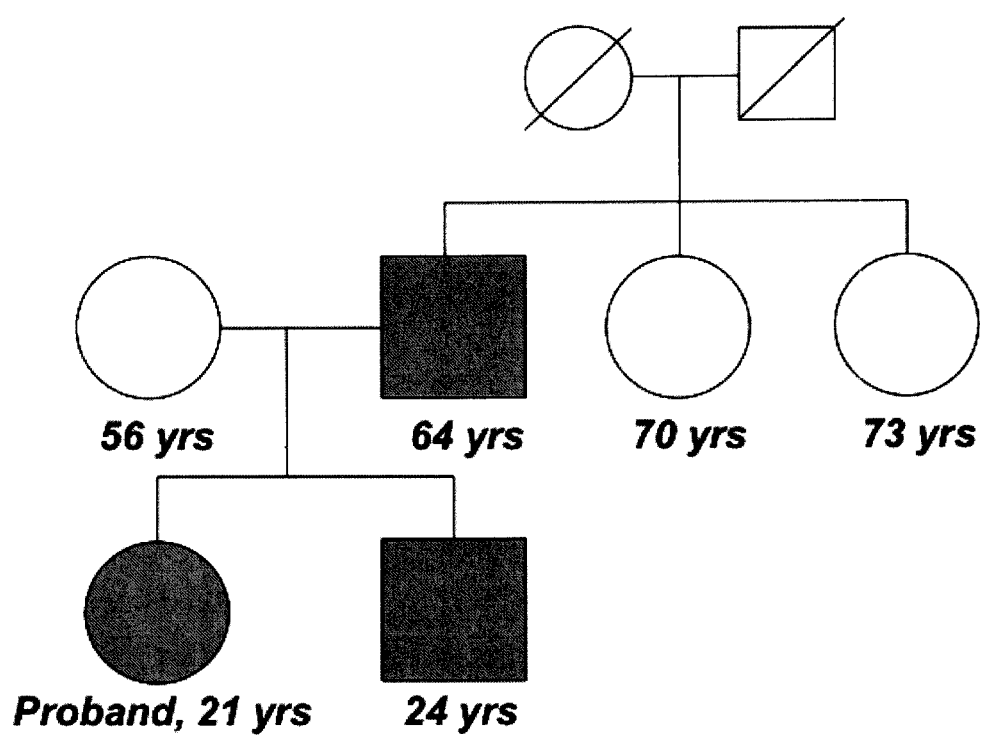
FIG. 10. Pedigree of a family with autosomal dominant common variable immunodeficiency FIG. 11. SVM Algorithm Hyperplane.

Similarly, the top 1000 significant SNPs for Bronchiectasis (Table 15) and OSAI (organ specific autoimmunity) (Table 16) as input to the SVM. Training: 107 no Bronchiectasis and 59 Bronchiectasis. Testing: 77 no Bronchiectasis and 19 Bronchiectasis. The model had 100% accuracy in the training stage and 97.9% accuracy in testing stage (FIG. 8). Evaluating our cohort for OSAI yielded Training: 117 no OSAI and 49 OSAI. Testing: 70 no OSAI and 26 OSAI. The model had 100% accuracy in the training stage and 99.0% accuracy in testing stage (FIG. 9).

To demonstrate poor model accuracy based on the same SVM methods, we ran the training stage with randomized testing data. The Bronchiectasis model applied to random affected labels and random genotypes resulted in a prediction accuracy of 27.1%. The Bronchiectasis model applied to random affected labels and correct genotypes resulted in a prediction accuracy of 77.1%. The OSAI model applied to random affected labels and correct genotypes resulted in a prediction accuracy of 67.7%. Given these markedly poorer accuracy results from randomized data compared to our observed data bolsters confidence that our high success rate is less likely due to a confounding factor, bias, or error.

This study represents the first genome-wide population based study of CVID. The use of the relatively large cohorts assembled here was essential, both to discover and to confirm the findings and demonstrates the potential of genome-wide association in complicated polygenic rare diseases. This type of unbiased study has discovered many novel targets that may underlie the development of CVID and provide clues to the pathogenesis of the heterogeneous clinical complications and subtypes of CVID, providing a solid foundation for further studies to understand the mechanism, interplay, and clinical manifestations of CVID, with the immediate potential of improving clinical management. Finally the great diversity identified with regards to unique CNV substantiates the hypothesis that CVIDs are a collection of diverse mechanisms leading to complex phenotypes.

TABLE 14

SNP Panel of 1994 SNPs for classifying CVID case versus individual without CVID

| | | | | | | | | | |
|---|---|---|---|---|---|---|---|---|---|
| rs3117426 | rs2239914 | rs9382495 | rs139234 | rs11132547 | rs1391772 | rs2107202 | rs3763338 | rs649647 | rs7677584 |
| rs2523535 | rs366178 | rs4269167 | rs17631106 | rs11135816 | rs1400438 | rs2112040 | rs3763822 | rs6504204 | rs7690236 |
| rs3130931 | rs17304375 | rs3130933 | rs13019329 | rs11138566 | rs1411439 | rs2113616 | rs3766566 | rs6505069 | rs7716554 |
| rs200968 | rs3129871 | rs9295768 | rs7085343 | rs11143520 | rs1419183 | rs2121289 | rs3772054 | rs6510040 | rs7761966 |
| rs879882 | rs1634719 | rs967005 | rs12270763 | rs11157606 | rs1421240 | rs2137512 | rs3775574 | rs6516091 | rs7762279 |
| rs3130564 | rs4654849 | rs2395174 | rs12447026 | rs11180576 | rs1422122 | rs214833 | rs3781216 | rs6538408 | rs7772160 |
| rs7767008 | rs2400955 | rs2931060 | rs10940184 | rs11183395 | rs1438935 | rs2153875 | rs3788111 | rs6549225 | rs7774197 |
| rs720831 | rs6581986 | rs10000770 | rs139240 | rs11206396 | rs1443365 | rs215393 | rs3788317 | rs6555424 | rs7774567 |
| rs4713208 | rs2429485 | rs10020322 | rs3802888 | rs11237730 | rs1444467 | rs2159318 | rs3796504 | rs656070 | rs7781284 |
| rs9266689 | rs3129975 | rs12636521 | rs17790790 | rs11247770 | rs1445358 | rs2168963 | rs3801332 | rs6577933 | rs7789182 |
| rs13194504 | rs17099394 | rs139136 | rs4871793 | rs157548 | rs1447398 | rs217180 | rs3804350 | rs6583700 | rs7808907 |
| rs6926142 | rs2395173 | rs9380006 | rs2279529 | rs11669334 | rs1452077 | rs2175835 | rs3810925 | rs6586116 | rs7815122 |
| rs4872262 | rs12495023 | rs10476080 | rs2902858 | rs11698275 | rs1461713 | rs220309 | rs3814585 | rs6590124 | rs7822769 |
| rs12680982 | rs10259703 | rs358994 | rs4720301 | rs11717880 | rs1466633 | rs2213215 | rs3818409 | rs6656611 | rs7834603 |
| rs6456785 | rs2505323 | rs12573587 | rs17372123 | rs11786911 | rs1477246 | rs2236861 | rs3847985 | rs6657001 | rs783756 |
| rs2517532 | rs2505327 | rs139135 | rs6679430 | rs11819553 | rs1481150 | rs2237236 | rs3863380 | rs6688151 | rs7838893 |
| rs2156875 | rs2484173 | rs3095340 | rs6485702 | rs1182865 | rs1497431 | rs2242660 | rs3913305 | rs6688807 | rs7857243 |
| rs3130501 | rs3132685 | rs11087123 | rs3134792 | rs11848008 | rs149990 | rs2256726 | rs3935608 | rs6694182 | rs7857474 |
| rs422717 | rs2523608 | rs9266440 | rs1377611 | rs11862051 | rs1523138 | rs2262808 | rs4082339 | rs6727285 | rs7867936 |
| rs393034 | rs3094122 | rs2718419 | rs9380120 | rs11873322 | rs1525745 | rs2277210 | rs4082846 | rs6737948 | rs7871753 |
| rs3117326 | rs8056528 | rs1194849 | rs6799262 | rs11906 | rs1544488 | rs2292263 | rs4146035 | rs6743415 | rs7887141 |

TABLE 14-continued

SNP Panel of 1994 SNPs for classifying CVID case versus individual without CVID

| | | | | | | | | | |
|---|---|---|---|---|---|---|---|---|---|
| rs3129882 | rs879484 | rs7718291 | rs12495026 | rs11915523 | rs1545692 | rs2292307 | rs4147525 | rs6759577 | rs7904468 |
| rs3130837 | rs2517549 | rs12458578 | rs2523989 | rs11924324 | rs1566579 | rs2295330 | rs420095 | rs6764451 | rs791033 |
| rs8321 | rs10734912 | rs6426636 | rs7945342 | rs11933720 | rs1569583 | rs2299395 | rs4236541 | rs6794896 | rs7928480 |
| rs6571989 | rs2523987 | rs469709 | rs950210 | rs1194491 | rs1571272 | rs2306810 | rs4238992 | rs6807774 | rs7937011 |
| rs9261290 | rs3130932 | rs9329172 | rs1406977 | rs11959994 | rs1574342 | rs2343468 | rs4320356 | rs6865181 | rs7939415 |
| rs858985 | rs2210313 | rs13104213 | rs720465 | rs11963652 | rs1582761 | rs2358483 | rs4324798 | rs6877998 | rs7964472 |
| rs1606234 | rs3135338 | rs1876518 | rs11870286 | rs11977312 | rs1592593 | rs2373146 | rs4353961 | rs6886088 | rs7970177 |
| rs3129791 | rs3770266 | rs2572690 | rs9257802 | rs11998428 | rs16181 | rs2389789 | rs4384353 | rs6903608 | rs8015024 |
| rs12924882 | rs149900 | rs2191388 | rs2517403 | rs12001157 | rs1619092 | rs2406233 | rs4409432 | rs6904596 | rs8015785 |
| rs4264554 | rs6457327 | rs3094127 | rs7103569 | rs12047230 | rs1629896 | rs2425628 | rs4486000 | rs6910095 | rs8020688 |
| rs17322265 | rs4871402 | rs386843 | rs12374025 | rs12049377 | rs1652500 | rs2427399 | rs4497887 | rs6917366 | rs8038569 |
| rs1453666 | rs2517448 | rs17099425 | rs10746192 | rs12060746 | rs1654774 | rs2448396 | rs4512403 | rs6917419 | rs8050560 |
| rs7087554 | rs2902982 | rs310319 | rs10254238 | rs120960 | rs1658102 | rs2455826 | rs4525114 | rs6921388 | rs8055387 |
| rs853676 | rs493965 | rs2733393 | rs139235 | rs12209633 | rs16891725 | rs2473700 | rs4531492 | rs6923139 | rs8057776 |
| rs3771781 | rs80303 | rs1539120 | rs3749530 | rs12146261 | rs16899857 | rs2492460 | rs454127 | rs6928830 | rs8061733 |
| rs203888 | rs9295730 | rs2844494 | rs2844635 | rs12147922 | rs16908361 | rs2497295 | rs4541737 | rs6933251 | rs8068923 |
| rs3094551 | rs200969 | rs133826 | rs1517927 | rs12148329 | rs16949286 | rs2514861 | rs4578658 | rs6938076 | rs8077733 |
| rs1634718 | rs1028308 | rs9344757 | rs17251715 | rs12149564 | rs16956295 | rs2517646 | rs4596286 | rs6939576 | rs8081687 |
| rs3094550 | rs3130350 | rs1214751 | rs9313540 | rs12188351 | rs16957467 | rs2523454 | rs4617771 | rs6947841 | rs8100750 |
| rs6127923 | rs2254556 | rs2130904 | rs4354950 | rs12190473 | rs16959820 | rs2535319 | rs464904 | rs6959814 | rs8105356 |
| rs1064191 | rs17293544 | rs2730306 | rs6785581 | rs12201890 | rs16971464 | rs2554675 | rs4671614 | rs6960076 | rs8109860 |
| rs2517452 | rs393990 | rs12145634 | rs2454873 | rs12204145 | rs17043526 | rs2555575 | rs4689343 | rs6961642 | rs8138344 |
| rs9257809 | rs16851846 | rs4350445 | rs5009448 | rs12238437 | rs17052298 | rs2560623 | rs4692098 | rs6972083 | rs821107 |
| rs895710 | rs1533476 | rs606448 | rs10018912 | rs12258095 | rs17090892 | rs258229 | rs4695718 | rs697614 | rs835361 |
| rs149951 | rs940052 | rs7617297 | rs10028187 | rs12261686 | rs17100060 | rs2589661 | rs4695791 | rs6981398 | rs835365 |
| rs6043091 | rs12924838 | rs10255854 | rs10058261 | rs12275853 | rs17100227 | rs2598464 | rs4712728 | rs6981439 | rs835378 |
| rs3749971 | rs10746490 | rs12577638 | rs10100444 | rs12276673 | rs17199261 | rs2629228 | rs4712955 | rs6993922 | rs835435 |
| rs12153912 | rs12445992 | rs2442749 | rs10101117 | rs12291520 | rs1733795 | rs2636767 | rs4712984 | rs6998016 | rs838893 |
| rs3094663 | rs9468276 | rs10916754 | rs1013696 | rs1233579 | rs17398230 | rs26685 | rs4737520 | rs7005380 | rs855974 |
| rs175597 | rs12093075 | rs7783758 | rs1013849 | rs1233708 | rs17400329 | rs2695636 | rs4754214 | rs7011777 | rs872111 |
| rs200953 | rs2517552 | rs7463896 | rs1014028 | rs1235162 | rs17402272 | rs2708594 | rs4758294 | rs7037024 | rs879921 |
| rs9257805 | rs3132538 | rs11780509 | rs10148024 | rs12405434 | rs17431811 | rs2708603 | rs4763780 | rs7041937 | rs886403 |
| rs1545523 | rs3130361 | rs2844729 | rs1015502 | rs12432589 | rs17434960 | rs2716456 | rs4764038 | rs7096350 | rs886424 |
| rs400404 | rs4894920 | rs10501763 | rs1018393 | rs12444655 | rs17436819 | rs2745061 | rs4764589 | rs7098890 | rs888932 |
| rs200951 | rs910064 | rs719927 | rs10189525 | rs12452324 | rs17476501 | rs2746150 | rs4765477 | rs7100025 | rs905780 |
| rs10494349 | rs12491592 | rs10517239 | rs10199875 | rs1247571 | rs17595027 | rs2755223 | rs4766329 | rs7108362 | rs9262143 |
| rs9950880 | rs1466065 | rs7657149 | rs10212407 | rs12563394 | rs17616999 | rs2765283 | rs4768814 | rs7109698 | rs9267947 |
| rs17803433 | rs11784192 | rs9921767 | rs10224415 | rs12571401 | rs17637266 | rs2777877 | rs4772030 | rs7110148 | rs9271366 |
| rs12712943 | rs2055918 | rs6679380 | rs10240549 | rs12574668 | rs17641748 | rs2791333 | rs4787348 | rs7122039 | rs9275602 |
| rs3130544 | rs2306029 | rs2516898 | rs10255489 | rs12577504 | rs17663626 | rs280816 | rs4814335 | rs7130141 | rs9295794 |
| rs17749927 | rs1609942 | rs11081638 | rs1036165 | rs1264514 | rs17699790 | rs280986 | rs4823340 | rs7130640 | rs9302358 |
| rs13062596 | rs3091661 | rs7193689 | rs1039128 | rs12665573 | rs17735101 | rs2813299 | rs4833753 | rs7141603 | rs9357078 |
| rs9444253 | rs1468042 | rs3856154 | rs1041981 | rs12679478 | rs17742080 | rs2815067 | rs484870 | rs7149428 | rs9366694 |
| rs7514144 | rs16867404 | rs17016917 | rs10428921 | rs1268097 | rs17760816 | rs2822670 | rs4849333 | rs717655 | rs9373537 |
| rs13194781 | rs2905722 | rs538186 | rs10464032 | rs12726611 | rs17798693 | rs2823594 | rs4862110 | rs7193708 | rs9379858 |
| rs3130827 | rs1196493 | rs3767996 | rs10484399 | rs12735814 | rs181027 | rs2823691 | rs4863305 | rs7216116 | rs9380064 |
| rs7750641 | rs7775818 | rs7707008 | rs10484560 | rs12744234 | rs181046 | rs2833979 | rs4899866 | rs7217235 | rs9393796 |
| rs506659 | rs3095329 | rs10946966 | rs10486023 | rs12787569 | rs1810636 | rs2834034 | rs4905713 | rs7224103 | rs9410486 |
| rs9348772 | rs1396400 | rs10994852 | rs10491190 | rs12801193 | rs1847039 | rs2836293 | rs4943552 | rs7233676 | rs9436188 |
| rs9257696 | rs17047183 | rs9380007 | rs10491964 | rs12807746 | rs1853156 | rs2859365 | rs4948286 | rs726532 | rs944963 |
| rs7972182 | rs359030 | rs3099844 | rs10500817 | rs12883308 | rs1858339 | rs287482 | rs4957798 | rs7267722 | rs9468209 |
| rs6940139 | rs1012411 | rs2217046 | rs10513315 | rs12892005 | rs1863050 | rs2876038 | rs4968363 | rs727708 | rs9468213 |
| rs10951566 | rs4320355 | rs200997 | rs10514840 | rs12898202 | rs1874655 | rs2913277 | rs497322 | rs7305297 | rs9468413 |
| rs853679 | rs1470539 | rs3094061 | rs10517209 | rs12908686 | rs1879689 | rs2953807 | rs497879 | rs736884 | rs9472202 |
| rs3132631 | rs2125639 | rs2833297 | rs10517365 | rs12969251 | rs1884123 | rs2959187 | rs529655 | rs737448 | rs9474687 |
| rs3132630 | rs7168491 | rs2516679 | rs1059260 | rs12971478 | rs1922407 | rs2974101 | rs534451 | rs740791 | rs9477950 |
| rs287355 | rs9322400 | rs6812482 | rs1073320 | rs13077924 | rs1932422 | rs3019885 | rs535842 | rs740854 | rs9529418 |
| rs12102284 | rs9384054 | rs2844670 | rs10736156 | rs13093086 | rs1935135 | rs3095314 | rs545833 | rs744280 | rs9574659 |
| rs11028465 | rs258873 | rs2473520 | rs10741559 | rs13095274 | rs1951805 | rs3105403 | rs547136 | rs7455060 | rs957566 |
| rs9380069 | rs6894136 | rs473925 | rs10746190 | rs13144404 | rs1952790 | rs3108396 | rs553219 | rs7463839 | rs9578469 |
| rs7115116 | rs9884830 | rs10238440 | rs10757394 | rs13164993 | rs1955490 | rs3116817 | rs556723 | rs7503953 | rs958731 |
| rs409783 | rs9382494 | rs6911628 | rs10760260 | rs1316537 | rs1955522 | rs3117143 | rs558560 | rs751717 | rs9598293 |
| rs2395182 | rs693196 | rs3094188 | rs10795445 | rs13185914 | rs1978454 | rs3128982 | rs5758991 | rs752479 | rs9608247 |
| rs4768959 | rs16972292 | rs734585 | rs10804253 | rs13195509 | rs1982672 | rs3130380 | rs6013355 | rs7543122 | rs9635993 |
| rs203890 | rs1438544 | rs4903707 | rs10828096 | rs13197574 | rs1994630 | rs3130817 | rs6017996 | rs7545388 | rs9638770 |
| rs6580783 | rs11178549 | rs133807 | rs10843894 | rs13198474 | rs1997960 | rs3130893 | rs603836 | rs7565134 | rs9669672 |
| rs1264551 | rs10916755 | rs2168801 | rs10845073 | rs13207908 | rs2014308 | rs3131093 | rs6049804 | rs7584650 | rs9767240 |
| rs2048507 | rs12922855 | rs12137004 | rs10902485 | rs13208164 | rs2027858 | rs3132486 | rs6083557 | rs7584862 | rs982234 |
| rs12532319 | rs1196488 | rs9295131 | rs10924469 | rs13211507 | rs203877 | rs3132580 | rs6084833 | rs7588316 | rs9837352 |
| rs1264547 | rs301396 | rs2143245 | rs10935431 | rs13240982 | rs2039290 | rs3132610 | rs618746 | rs7617594 | rs9842506 |
| rs4558863 | rs258862 | rs12623733 | rs10946940 | rs13274015 | rs2042280 | rs3134603 | rs621310 | rs7623321 | rs9846423 |
| rs3094054 | rs573118 | rs847067 | rs10955450 | rs13297297 | rs2060321 | rs3134954 | rs637384 | rs7628034 | rs9846545 |
| rs287351 | rs17273893 | rs8069430 | rs11026531 | rs13297471 | rs2066363 | rs328294 | rs638324 | rs7630157 | rs9850579 |
| rs3770267 | rs12417962 | rs3823055 | rs11028548 | rs1332226 | rs2067869 | rs338479 | rs6456834 | rs7634908 | rs9879707 |
| rs974332 | rs3781703 | rs2833293 | rs11032297 | rs1344723 | rs2071591 | rs347965 | rs6469858 | rs7636581 | rs9882269 |
| rs11207520 | rs12637203 | rs6504930 | rs11071519 | rs13448 | rs2076305 | rs371915 | rs6473735 | rs764971 | rs9923061 |
| rs2048508 | rs1503920 | rs1364290 | rs11078454 | rs1349951 | rs2076346 | rs3755458 | rs6482358 | rs7651055 | rs9934109 |
| rs12193434 | rs869340 | rs2047456 | rs11084476 | rs1366963 | rs2076537 | rs3759864 | rs6482573 | rs7654623 | rs997448 |

TABLE 14-continued

SNP Panel of 1994 SNPs for classifying CVID case versus individual without CVID

| | | | | | | | | | |
|---|---|---|---|---|---|---|---|---|---|
| rs2285415 | rs569078 | rs9303355 | rs11123677 | rs1387815 | rs2076624 | rs3761093 | rs6485690 | rs766127 | rs999900 |
| rs12086296 | rs1953858 | rs7661151 | rs9938215 | rs11588952 | rs13252630 | rs1894090 | rs2985902 | rs58901 | rs7576475 |
| rs12095205 | rs6864519 | rs4257189 | rs7979863 | rs11591167 | rs1326415 | rs1898462 | rs3007290 | rs596167 | rs7580465 |
| rs1886740 | rs11144516 | rs12507717 | rs1000408 | rs1159372 | rs13275988 | rs1923105 | rs302113 | rs6008581 | rs7583467 |
| rs875688 | rs6470066 | rs34687 | rs10014832 | rs11617865 | rs13290774 | rs1925690 | rs303545 | rs6011734 | rs7591430 |
| rs230177 | rs7143400 | rs2594897 | rs10021608 | rs11619258 | rs13336037 | rs1932169 | rs30425 | rs6024661 | rs761021 |
| rs2652130 | rs12155344 | rs1476994 | rs10022535 | rs11635501 | rs1336892 | rs1944888 | rs3095089 | rs6024723 | rs7634304 |
| rs6728658 | rs486238 | rs13263545 | rs10032135 | rs11637538 | rs1338588 | rs1952098 | rs3133250 | rs6028945 | rs7669997 |
| rs10833106 | rs316013 | rs6982249 | rs1003991 | rs11654639 | rs1342602 | rs1956521 | rs316003 | rs6056595 | rs7673654 |
| rs230178 | rs10806731 | rs2769004 | rs10040906 | rs11670621 | rs1353681 | rs1975920 | rs316780 | rs6062957 | rs7684327 |
| rs6489056 | rs598908 | rs282416 | rs10053502 | rs11675971 | rs1365016 | rs1995598 | rs328144 | rs6064315 | rs7711139 |
| rs2435962 | rs2256141 | rs2585197 | rs10065046 | rs11683424 | rs136631 | rs1995863 | rs330792 | rs6065409 | rs7728954 |
| rs1391049 | rs10484893 | rs7140766 | rs10070799 | rs11720980 | rs1374460 | rs2001087 | rs353826 | rs6069541 | rs7731260 |
| rs9380602 | rs7798161 | rs11157866 | rs10090889 | rs11727494 | rs1385340 | rs2027363 | rs35402 | rs6074798 | rs7743003 |
| rs3734078 | rs10440376 | rs40507 | rs10092250 | rs11728925 | rs139394 | rs2038359 | rs3739464 | rs6113074 | rs7752724 |
| rs10744242 | rs1333217 | rs4624543 | rs10114302 | rs11735072 | rs1401014 | rs2043388 | rs3743466 | rs6123013 | rs7754710 |
| rs2447753 | rs10899269 | rs709012 | rs10163150 | rs11735242 | rs1407179 | rs2045058 | rs3751221 | rs6124082 | rs7772299 |
| rs11058480 | rs2059058 | rs12537855 | rs10188058 | rs11749633 | rs1411456 | rs2050198 | rs3774285 | rs634265 | rs7773199 |
| rs230174 | rs7962622 | rs580333 | rs1020670 | rs11760907 | rs1432237 | rs2054017 | rs3777102 | rs6469525 | rs7784465 |
| rs6661744 | rs3783870 | rs904962 | rs10242195 | rs11770757 | rs1447826 | rs2068914 | rs3781408 | rs6473241 | rs7786745 |
| rs10753109 | rs11982298 | rs10225065 | rs10243212 | rs11776451 | rs1455311 | rs2073917 | rs3803004 | rs6491316 | rs7800935 |
| rs10934667 | rs13253691 | rs923963 | rs10256012 | rs11784473 | rs1462559 | rs2076370 | rs3808528 | rs6508244 | rs7805356 |
| rs10222858 | rs975317 | rs4675438 | rs10265223 | rs11824645 | rs1464728 | rs209445 | rs3813218 | rs6566546 | rs7837249 |
| rs8008081 | rs11622145 | rs34689 | rs10275033 | rs11867922 | rs1469587 | rs2108294 | rs3817614 | rs6568006 | rs7867090 |
| rs34677 | rs9811068 | rs7154632 | rs1027604 | rs11905518 | rs1492178 | rs2138244 | rs3845732 | rs6571692 | rs7894314 |
| rs11058562 | rs1007289 | rs2019214 | rs10276544 | rs11914777 | rs1502795 | rs2161393 | rs3846911 | rs6572412 | rs790838 |
| rs1480548 | rs1373928 | rs7034698 | rs1036819 | rs1192380 | rs1502815 | rs2165419 | rs3850590 | rs6578882 | rs7911956 |
| rs10742380 | rs1373930 | rs11237688 | rs1039326 | rs11933412 | rs1503854 | rs2165440 | rs3857404 | rs6580288 | rs7926934 |
| rs10752798 | rs1461780 | rs2830706 | rs10407008 | rs11947802 | rs1510909 | rs2174804 | rs3858336 | rs6589849 | rs7929621 |
| rs2110328 | rs4721679 | rs6766607 | rs10417646 | rs11955226 | rs1519982 | rs2181139 | rs3864883 | rs6594352 | rs7938 |
| rs9364554 | rs6676552 | rs1007764 | rs1043595 | rs1203181 | rs1528461 | rs2193976 | rs38964 | rs6600320 | rs7941806 |
| rs1384862 | rs3887233 | rs3125056 | rs1047033 | rs12037664 | rs1535060 | rs2194232 | rs3909722 | rs6659944 | rs7960169 |
| rs7517989 | rs10850917 | rs2685513 | rs10481751 | rs12039124 | rs1539057 | rs2195101 | rs3912477 | rs666432 | rs7976970 |
| rs10799220 | rs10898550 | rs1029508 | rs10483284 | rs12039194 | rs1546120 | rs2204506 | rs3923626 | rs6672510 | rs7981535 |
| rs11684509 | rs9301487 | rs11167794 | rs10483345 | rs12102589 | rs1549343 | rs2221705 | rs4012731 | rs6689095 | rs7986486 |
| rs7679866 | rs17124780 | rs1440954 | rs10483749 | rs12113865 | rs1555649 | rs2236479 | rs404220 | rs6692418 | rs8006182 |
| rs10003811 | rs3755665 | rs540697 | rs10483752 | rs1211864 | rs1556190 | rs224632 | rs4078315 | rs6700346 | rs8014539 |
| rs1593398 | rs1444756 | rs10498440 | rs10484710 | rs12119869 | rs1559101 | rs225132 | rs4237471 | rs6705017 | rs8021964 |
| rs12401659 | rs6809208 | rs4917727 | rs10485722 | rs12124645 | rs1570677 | rs2255313 | rs4239638 | rs6719977 | rs8024016 |
| rs10933421 | rs2045838 | rs33352 | rs10487264 | rs157198 | rs1571359 | rs4239875 | rs6723590 | rs8027714 | |
| rs17284917 | rs12703848 | rs13169010 | rs10490741 | rs12187771 | rs1572312 | rs2275979 | rs4246703 | rs6726265 | rs8057939 |
| rs997131 | rs10913056 | rs10765174 | rs10493695 | rs12194954 | rs1617406 | rs2278404 | rs4247190 | rs6741951 | rs8076084 |
| rs11723364 | rs17485462 | rs1422780 | rs10496080 | rs12197035 | rs16837801 | rs2279664 | rs4251739 | rs6747421 | rs8079249 |
| rs9997989 | rs7754676 | rs16840921 | rs10497071 | rs12206076 | rs16842293 | rs2279986 | rs432959 | rs6756097 | rs808338 |
| rs3746406 | rs649611 | rs10226333 | rs10497422 | rs12210297 | rs16870964 | rs2285487 | rs4359096 | rs6762119 | rs8086871 |
| rs11721736 | rs2289709 | rs4270027 | rs10507882 | rs12292437 | rs1687503 | rs2287904 | rs4360077 | rs6763408 | rs8100291 |
| rs17633196 | rs1373931 | rs2816316 | rs10508006 | rs12298502 | rs16903944 | rs2287906 | rs4376903 | rs6790285 | rs8107145 |
| rs15612 | rs17347590 | rs12536890 | rs10508704 | rs12345213 | rs16942077 | rs2291220 | rs4385337 | rs6805004 | rs8118662 |
| rs6430676 | rs2116280 | rs7818198 | rs10514583 | rs12358866 | rs16945809 | rs2292645 | rs4448310 | rs6824270 | rs813328 |
| rs6775178 | rs1471403 | rs866279 | rs10514908 | rs12360927 | rs16957064 | rs2300520 | rs4482854 | rs6832174 | rs816812 |
| rs2245199 | rs9873621 | rs659450 | rs10516548 | rs12458088 | rs16959254 | rs2302107 | rs4523256 | rs6833298 | rs84823 |
| rs16827675 | rs7044480 | rs12903340 | rs10518315 | rs12486791 | rs16973160 | rs2303063 | rs4542999 | rs6853448 | rs876458 |
| rs2607374 | rs1005051 | rs11979495 | rs10519160 | rs12489686 | rs16976984 | rs2328014 | rs4557653 | rs6860662 | rs878357 |
| rs2093045 | rs7863610 | rs6732762 | rs10519460 | rs12493932 | rs17019212 | rs2332074 | rs4572252 | rs6864345 | rs885157 |
| rs184968 | rs2809285 | rs6717822 | rs10521955 | rs12496156 | rs1704589 | rs233251 | rs4598609 | rs6883259 | rs888186 |
| rs17551608 | rs2594909 | rs1510868 | rs1052653 | rs17047071 | rs2344553 | rs4600036 | rs6883877 | rs892458 | |
| rs2396327 | rs6771029 | rs4242363 | rs1064524 | rs12511535 | rs17089390 | rs2348553 | rs4611118 | rs6890880 | rs905067 |
| rs6426408 | rs10799632 | rs10483709 | rs10734418 | rs1253690 | rs170974 | rs2354040 | rs4623688 | rs6892994 | rs914405 |
| rs2236561 | rs10915494 | rs12261638 | rs10738758 | rs12541121 | rs17106642 | rs2365491 | rs4636656 | rs6936594 | rs9320043 |
| rs607138 | rs2984920 | rs1440950 | rs10764760 | rs12549864 | rs17114086 | rs2373974 | rs4662336 | rs6982126 | rs933235 |
| rs11086147 | rs643556 | rs4072280 | rs10783289 | rs12565883 | rs17125944 | rs2394527 | rs4664723 | rs6995299 | rs9346816 |
| rs16980240 | rs913834 | rs13275678 | rs10793139 | rs12566065 | rs17128651 | rs2397355 | rs4700281 | rs7000759 | rs9365900 |
| rs17149499 | rs10409727 | rs2805533 | rs10801172 | rs12599653 | rs17134117 | rs2407999 | rs4703363 | rs7002144 | rs9366027 |
| rs6957548 | rs656635 | rs2476779 | rs10801415 | rs12601054 | rs17147479 | rs2408347 | rs4709877 | rs7014566 | rs9396682 |
| rs11196077 | rs2288898 | rs12555933 | rs1808042 | rs12612926 | rs17164435 | rs2442579 | rs4721879 | rs7016252 | rs9431471 |
| rs4468370 | rs2288897 | rs479772 | rs10818014 | rs12656332 | rs17172860 | rs245891 | rs4732639 | rs7029119 | rs944223 |
| rs2177627 | rs13127257 | rs1040049 | rs10841511 | rs12669415 | rs17176792 | rs2462692 | rs4736424 | rs704010 | rs9445788 |
| rs630760 | rs2902990 | rs4233164 | rs10847189 | rs12676720 | rs17184300 | rs247325 | rs4760176 | rs704265 | rs9453898 |
| rs1323292 | rs6019266 | rs1111366 | rs10847353 | rs12698419 | rs17193036 | rs2513938 | rs4766885 | rs7043995 | rs9460864 |
| rs610490 | rs7044607 | rs2971927 | rs10875883 | rs12718513 | rs17208897 | rs2520570 | rs4771059 | rs706293 | rs9535048 |
| rs7613062 | rs7295136 | rs504093 | rs10894155 | rs12727642 | rs17214357 | rs2553226 | rs4771063 | rs7114098 | rs9536654 |
| rs9290973 | rs13262033 | rs933153 | rs10921466 | rs12733466 | rs17224695 | rs2553600 | rs4778871 | rs712414 | rs9556934 |
| rs1537479 | rs4316158 | rs2883367 | rs10921627 | rs17382 | rs1725132 | rs260879 | rs4785434 | rs712457 | rs9572312 |
| rs7613679 | rs7681088 | rs10997263 | rs10924303 | rs12744534 | rs1725132 | rs2613179 | rs4808652 | rs7137203 | rs9601157 |
| rs2168659 | rs2161299 | rs836556 | rs10928866 | rs12746344 | rs17314091 | rs2623702 | rs4809958 | rs7153143 | rs9608024 |
| rs6128302 | rs3914329 | rs7150859 | rs10932158 | rs12748679 | rs17365609 | rs2630397 | rs4810622 | rs7160582 | rs9769000 |
| rs10847227 | rs2703978 | rs4262641 | rs10940024 | rs12769098 | rs17389911 | rs26775 | rs4856002 | rs717163 | rs977712 |
| rs474304 | rs7107322 | rs4146018 | rs10944479 | rs12781083 | rs17402243 | rs2691782 | rs4858594 | rs71815 | rs977799 |

TABLE 14-continued

SNP Panel of 1994 SNPs for classifying CVID case versus individual without CVID

| | | | | | | | | | |
|---|---|---|---|---|---|---|---|---|---|
| rs6726035 | rs2769006 | rs11749794 | rs10961505 | rs12813396 | rs1748329 | rs269718 | rs4859011 | rs719428 | rs978268 |
| rs3746405 | rs2295746 | rs17562787 | rs10968347 | rs12817342 | rs17521729 | rs270050 | rs4859325 | rs7250113 | rs9784568 |
| rs2702671 | rs1353583 | rs10822856 | rs10984477 | rs1281747 | rs17548847 | rs2703130 | rs4861993 | rs725579 | rs9809600 |
| rs1893306 | rs7962880 | rs6542736 | rs10984490 | rs12827322 | rs17627259 | rs2703960 | rs4864553 | rs726558 | rs9809773 |
| rs315995 | rs6714893 | rs9844737 | rs1100185 | rs12882217 | rs17654772 | rs274646 | rs4865815 | rs7272481 | rs982511 |
| rs12155045 | rs7171256 | rs1316471 | rs11014455 | rs12885228 | rs1765886 | rs2755176 | rs4885371 | rs728034 | rs9835081 |
| rs6128300 | rs1003802 | rs236410 | rs11022509 | rs1289501 | rs17685418 | rs2763419 | rs4901523 | rs729154 | rs9848911 |
| rs11666885 | rs13214001 | rs473585 | rs11033019 | rs12982321 | rs17692241 | rs2802884 | rs4915723 | rs729648 | rs9861236 |
| rs2685515 | rs316021 | rs2420175 | rs11059821 | rs12990534 | rs17709684 | rs2817200 | rs4920566 | rs731809 | rs9874349 |
| rs6748817 | rs4972265 | rs3886771 | rs11128687 | rs12996858 | rs17726892 | rs2821236 | rs4921593 | rs7321884 | rs988158 |
| rs2279351 | rs1650817 | rs2025633 | rs11131055 | rs13023918 | rs17734487 | rs2822850 | rs4933679 | rs734434 | rs988179 |
| rs11059258 | rs7265772 | rs6012463 | rs11143230 | rs13035689 | rs17761855 | rs2825673 | rs494469 | rs7349465 | rs9904523 |
| rs4130446 | rs7724262 | rs3849699 | rs11165460 | rs1304065 | rs17796406 | rs2852424 | rs4950989 | rs739107 | rs9912125 |
| rs7084512 | rs251039 | rs12188691 | rs11186642 | rs13081891 | rs17817943 | rs2877498 | rs4976254 | rs740096 | rs9913538 |
| rs627830 | rs2057904 | rs9325837 | rs11194816 | rs13086978 | rs17829645 | rs2887022 | rs4978774 | rs7415038 | rs9919607 |
| rs2052701 | rs12608393 | rs2010464 | rs11218881 | rs13128635 | rs178377 | rs2904295 | rs4981149 | rs7428676 | rs9966000 |
| rs1475784 | rs2475793 | rs13394087 | rs1124359 | rs13132576 | rs1790024 | rs2914079 | rs4984626 | rs752278 | rs9989335 |
| rs6419277 | rs2455308 | rs11237690 | rs11250154 | rs13142179 | rs1833755 | rs2924264 | rs500293 | rs7539255 | |
| rs6769238 | rs1808378 | rs2152174 | rs1146229 | rs13189435 | rs1861089 | rs2940930 | rs536299 | rs7544671 | |
| rs7306734 | rs4521737 | rs4947602 | rs1152986 | rs13203110 | rs186493 | rs296200 | rs542988 | rs7553961 | |
| rs3125050 | rs547491 | rs6437079 | rs11547160 | rs13224666 | rs1866714 | rs2962270 | rs556439 | rs7554157 | |
| rs2174559 | rs1477602 | rs7609626 | rs1156250 | rs13229792 | rs1885831 | rs2972418 | rs568789 | rs7555638 | |
| rs6661074 | rs7792461 | rs722938 | rs11576361 | rs13238853 | rs1889356 | rs2974617 | rs587263 | rs7574670 | |

TABLE 15

SNP Panel of 1000 SNPs for classifying CVID case with Bronchiectasis versus CVID case without Bronchiectasis

| | | | | | | | | | |
|---|---|---|---|---|---|---|---|---|---|
| rs3101219 | rs1866236 | rs9837945 | rs7700961 | rs6950759 | rs7021834 | rs6590583 | rs8011776 | rs6508240 | rs5925649 |
| rs4908463 | rs1349159 | rs13083177 | rs297884 | rs2191714 | rs1536864 | rs6590584 | rs7174078 | rs2120663 | rs5925651 |
| rs1725262 | rs1448917 | rs960353 | rs7735038 | rs2330055 | rs11142904 | rs6590694 | rs11858397 | rs16946189 | rs5926027 |
| rs10864368 | rs12612313 | rs7629105 | rs1050975 | rs11238193 | rs7037278 | rs546381 | rs17227996 | rs1350552 | rs5926032 |
| rs2071414 | rs6436652 | rs6443582 | rs1890366 | rs296308 | rs2378383 | rs11054372 | rs12439272 | rs621834 | rs7882511 |
| rs12034719 | rs9288624 | rs1522262 | rs1933650 | rs11766378 | rs7025226 | rs2071163 | rs4924613 | rs2433396 | rs1527808 |
| rs2982380 | rs1515928 | rs1994855 | rs6904644 | rs10499751 | rs12238088 | rs2239176 | rs1712426 | rs2847593 | rs5943997 |
| rs17038468 | rs2556097 | rs12487104 | rs1331489 | rs10270164 | rs10491791 | rs901528 | rs3825786 | rs7241842 | rs12557438 |
| rs1812242 | rs1561466 | rs4602335 | rs1571827 | rs13240999 | rs7874528 | rs10841413 | rs12439521 | rs16977580 | rs16988109 |
| rs4970535 | rs13033944 | rs4472002 | rs9391956 | rs12698917 | rs17428350 | rs2417862 | rs7178085 | rs1942159 | rs12014989 |
| rs12126652 | rs830994 | rs4234788 | rs3812179 | rs258702 | rs7871887 | rs2203494 | rs11855605 | rs3753067 | rs1419850 |
| rs12131682 | rs831007 | rs7435615 | rs3812178 | rs2888019 | rs10818955 | rs11045417 | rs2306335 | rs11152012 | rs5973335 |
| rs272561 | rs831011 | rs4697075 | rs7760489 | rs1557785 | rs1413294 | rs1861710 | rs1993865 | rs11663936 | rs728149 |
| rs1051648 | rs6707969 | rs2167955 | rs966840 | rs1921598 | rs2114012 | rs10492367 | rs1026695 | rs10516006 | rs7064305 |
| rs3444 | rs16862458 | rs5002502 | rs13196069 | rs1526491 | rs3847303 | rs7307357 | rs4776191 | rs17638216 | rs5972346 |
| rs6667593 | rs6433615 | rs7665747 | rs12665403 | rs7781914 | rs328875 | rs2388962 | rs1904109 | rs7251154 | rs2124748 |
| rs2354463 | rs13032587 | rs12186184 | rs1905212 | rs2188508 | rs7852829 | rs10844021 | rs17183491 | rs10416824 | rs228379 |
| rs10493140 | rs17362588 | rs1377347 | rs9476488 | rs17166818 | rs1385143 | rs1666235 | rs3809539 | rs6508999 | rs2180648 |
| rs10888636 | rs2290517 | rs13116757 | rs9358858 | rs1015882 | rs4979619 | rs10743775 | rs1865930 | rs7254214 | rs5917579 |
| rs2806405 | rs12465639 | rs7349609 | rs6904130 | rs2158137 | rs12236795 | rs12319134 | rs11858355 | rs1594895 | rs1800321 |
| rs2764687 | rs10204810 | rs4527518 | rs2524099 | rs10275909 | rs7020797 | rs995342 | rs12914140 | rs2217672 | rs5917584 |
| rs12728521 | rs4667046 | rs10034992 | rs9501626 | rs7777145 | rs10481656 | rs1389134 | rs8032153 | rs8113456 | rs11266207 |
| rs17124275 | rs785240 | rs1000226 | rs3135338 | rs3735258 | rs7049083 | rs1498712 | rs11639228 | rs6509286 | rs5917593 |
| rs4512683 | rs12613687 | rs2622604 | rs2027856 | rs234 | rs7041855 | rs10877894 | rs4436753 | rs689292 | rs5964215 |
| rs11208446 | rs6740981 | rs1708670 | rs2395173 | rs17356935 | rs1249904 | rs11174573 | rs4534816 | rs3746660 | rs2239455 |
| rs12407601 | rs10445792 | rs583908 | rs154978 | rs7455060 | rs5025067 | rs3936640 | rs6497041 | rs6084506 | rs10854983 |
| rs6663109 | rs4673837 | rs4693223 | rs958423 | rs10272242 | rs10818337 | rs3864455 | rs11635007 | rs998132 | rs5919551 |
| rs7522367 | rs6739563 | rs10049681 | rs804829 | rs6466735 | rs10984619 | rs4763120 | rs768399 | rs945767 | rs5919560 |
| rs11208834 | rs11687313 | rs10516451 | rs1109798 | rs4726499 | rs11790238 | rs11175217 | rs8024991 | rs6139278 | rs5936698 |
| rs1415974 | rs4672726 | rs4833233 | rs3807045 | rs2001942 | rs6478430 | rs962415 | rs12591805 | rs6076598 | rs7056340 |
| rs3738168 | rs2043769 | rs1155135 | rs2257082 | rs12703419 | rs1860665 | rs10506554 | rs13380379 | rs6516091 | rs6625489 |
| rs787492 | rs13019534 | rs1480902 | rs941967 | rs855740 | rs2297454 | rs10506762 | rs4965678 | rs6054459 | rs5936708 |
| rs7541725 | rs12053340 | rs1383518 | rs2268718 | rs1111467 | rs10818649 | rs919993 | rs7177883 | rs2206423 | rs1327347 |
| rs6691042 | rs1527944 | rs13125153 | rs1079060 | rs10988617 | rs12468358 | rs99944290 | rs9944290 | rs2050104 | rs5936488 |
| rs617196 | rs1527947 | rs12503254 | rs1377392 | rs2952648 | rs11103479 | rs7300004 | rs11640138 | rs8120907 | rs5936735 |
| rs263463 | rs16836294 | rs1456266 | rs10948750 | rs11777063 | rs10905076 | rs10777720 | rs415595 | rs2223565 | rs6418420 |
| rs263495 | rs17450826 | rs951850 | rs9342394 | rs6558946 | rs12781427 | rs3782518 | rs949429 | rs1033470 | rs5936510 |
| rs12409961 | rs12472818 | rs4569797 | rs701699 | rs7816614 | rs10752197 | rs2293055 | rs12918743 | rs4813897 | rs5980665 |
| rs2295330 | rs16858496 | rs939689 | rs493265 | rs1526371 | rs7092558 | rs11615235 | rs7404377 | rs6040808 | rs5936518 |
| rs11184300 | rs12464171 | rs6536370 | rs9351817 | rs2527748 | rs7897007 | rs4760566 | rs238848 | rs2009018 | rs5936520 |
| rs11184318 | rs10933001 | rs6858744 | rs199623 | rs13254568 | rs11816696 | rs2129663 | rs2521477 | rs6110058 | rs5936795 |
| rs2765283 | rs12479209 | rs2047629 | rs12207816 | rs7836269 | rs12254001 | rs1734809 | rs2910848 | rs17272940 | rs5936790 |
| rs7516108 | rs1400795 | rs13140600 | rs16881643 | rs2736020 | rs749631 | rs7300570 | rs8045557 | rs6079923 | rs5936524 |
| rs401904 | rs17371273 | rs2706740 | rs10485242 | rs1563297 | rs2793345 | rs12422489 | rs763763 | rs6046129 | rs3811372 |
| rs1748383 | rs6711657 | rs2706727 | rs16881894 | rs2720611 | rs7071467 | rs1334958 | rs3935714 | rs7267722 | rs749789 |
| rs7523184 | rs12463466 | rs2660404 | rs10944450 | rs4831774 | rs7911971 | rs9510802 | rs257868 | rs6049003 | rs7879974 |
| rs1986860 | rs7355380 | rs6841955 | rs16881936 | rs10503553 | rs4256883 | rs4771142 | rs9926100 | rs6121337 | rs6615046 |

TABLE 15-continued

SNP Panel of 1000 SNPs for classifying CVID case with Bronchiectasis versus CVID case without Bronchiectasis

| | | | | | | | | | |
|---|---|---|---|---|---|---|---|---|---|
| rs4233394 | rs11685503 | rs2082317 | rs7754169 | rs822249 | rs2138566 | rs1336628 | rs7199018 | rs228838 | rs12012447 |
| rs4540634 | rs2645779 | rs11729502 | rs822304 | rs2518321 | rs10822031 | rs4771033 | rs7188866 | rs6126431 | rs5958896 |
| rs1986385 | rs1705805 | rs11725347 | rs12212740 | rs11203812 | rs10996997 | rs903777 | rs8049176 | rs6069746 | rs6621735 |
| rs2766085 | rs17709863 | rs6818908 | rs1858234 | rs11204097 | rs10762038 | rs1952994 | rs8047279 | rs438363 | rs5985075 |
| rs12062372 | rs356418 | rs11733679 | rs4371861 | rs12545707 | rs2894317 | rs391933 | rs16959476 | rs160396 | rs5942366 |
| rs10800150 | rs6769422 | rs10024068 | rs6913196 | rs7841346 | rs890687 | rs398655 | rs12449237 | rs1151621 | rs5942534 |
| rs10918281 | rs9875884 | rs7698980 | rs1933755 | rs2942202 | rs1550023 | rs9603418 | rs4458015 | rs6062292 | rs5941436 |
| rs4472738 | rs11129323 | rs2280664 | rs9492657 | rs2685320 | rs1684543 | rs4346095 | rs8057941 | rs8129104 | rs1570995 |
| rs6680341 | rs1015856 | rs2692596 | rs2249821 | rs11136019 | rs4547043 | rs9526255 | rs17296283 | rs443823 | rs6522689 |
| rs10489199 | rs9837352 | rs1288536 | rs2807278 | rs7833986 | rs2497304 | rs4534729 | rs13338146 | rs2407255 | rs638376 |
| rs2205851 | rs33454 | rs6849285 | rs2024692 | rs7822429 | rs10736156 | rs17069883 | rs17712938 | rs2825809 | rs12833867 |
| rs232293 | rs3821477 | rs11724261 | rs9403904 | rs4397440 | rs10884480 | rs9534596 | rs11648482 | rs2825817 | rs6644233 |
| rs1933539 | rs971866 | rs957792 | rs4870376 | rs7824497 | rs10748948 | rs1323537 | rs8055798 | rs2825819 | rs12556735 |
| rs6593937 | rs715382 | rs1444127 | rs9322536 | rs924740 | rs10749189 | rs9535080 | rs16955356 | rs2826213 | rs5910956 |
| rs12061474 | rs7647357 | rs16892616 | rs12174424 | rs1545824 | rs690870 | rs777771 | rs2317835 | rs236044 | rs4373692 |
| rs11579791 | rs6810180 | rs4869452 | rs2770104 | rs2128105 | rs7073467 | rs9598119 | rs378138 | rs5992088 | rs204330 |
| rs10489951 | rs6445254 | rs6883671 | rs1118242 | rs7832751 | rs3011399 | rs2137512 | rs1946482 | rs2535707 | rs203490 |
| rs892975 | rs11130981 | rs1466011 | rs9654570 | rs7015186 | rs3011408 | rs7988149 | rs8081951 | rs361893 | rs16309 |
| rs6426156 | rs1283532 | rs2910468 | rs751873 | rs6472384 | rs7070793 | rs3013580 | rs7219019 | rs849357 | rs201637 |
| rs4653662 | rs7373042 | rs2910469 | rs9456433 | rs11778612 | rs1898463 | rs4884738 | rs17762680 | rs1297593 | rs149908 |
| rs973252 | rs13100924 | rs1423131 | rs4368835 | rs17824659 | rs11248595 | rs7997966 | rs7215084 | rs1807510 | rs2046394 |
| rs2808611 | rs6548962 | rs2910475 | rs10214534 | rs6472770 | rs11244515 | rs9317784 | rs7503953 | rs738456 | rs683335 |
| rs2808614 | rs7610023 | rs2961838 | rs2457571 | rs7461233 | rs4962566 | rs2325194 | rs4792143 | rs392277 | rs46562 |
| rs11122322 | rs6548984 | rs1862526 | rs9365646 | rs5017296 | rs12098358 | rs1446385 | rs4393623 | rs5752634 | rs5932370 |
| rs2814536 | rs2136715 | rs1309824 | rs9365647 | rs3735912 | rs7124824 | rs1249772 | rs12451200 | rs427736 | rs5932394 |
| rs2644441 | rs4855469 | rs10940096 | rs9355453 | rs13272532 | rs903209 | rs1334825 | rs8067882 | rs5762430 | rs6637420 |
| rs1874400 | rs6549411 | rs2937715 | rs9355454 | rs17700155 | rs2283257 | rs1112466 | rs1555142 | rs470105 | rs6529359 |
| rs3011577 | rs9310222 | rs10064609 | rs916368 | rs9969608 | rs2270024 | rs2325364 | rs8073784 | rs5762461 | rs5932624 |
| rs4443876 | rs2322165 | rs13164793 | rs6915442 | rs4602925 | rs4569005 | rs9600257 | rs2075053 | rs5750726 | rs1324149 |
| rs4658702 | rs2322162 | rs33003 | rs221725 | rs7823271 | rs869377 | rs9573480 | rs11079868 | rs4821862 | rs5975531 |
| rs12407427 | rs11718674 | rs6874731 | rs221723 | rs6983626 | rs11103106 | rs9565288 | rs747039 | rs2014881 | rs5954074 |
| rs1039010 | rs11921763 | rs4703545 | rs7789861 | rs1550856 | rs4923526 | rs4635230 | rs17637472 | rs2076101 | rs12687312 |
| rs384526 | rs12714781 | rs2656984 | rs12540575 | rs3019885 | rs924714 | rs9517921 | rs11869714 | rs5758991 | rs644210 |
| rs6542651 | rs6765942 | rs1505000 | rs4719266 | rs10464861 | rs1216155 | rs11069386 | rs739924 | rs9615362 | rs5919819 |
| rs2872977 | rs1319094 | rs448840 | rs6460807 | rs7816758 | rs10897108 | rs9805437 | rs11611374 | rs9627450 | rs5965846 |
| rs934615 | rs7616034 | rs7733888 | rs6970647 | rs4593504 | rs4930431 | rs12428930 | rs9892374 | rs4459004 | rs1337635 |
| rs2110965 | rs11718781 | rs1449227 | rs136 | rs12674562 | rs7118125 | rs9521350 | rs9907787 | rs1026162 | rs596987 |
| rs7562836 | rs10049211 | rs4869255 | rs142 | rs1768869 | rs7946537 | rs12886280 | rs11653824 | rs4641225 | rs580628 |
| rs13427136 | rs11128275 | rs1974789 | rs135 | rs10511649 | rs567236 | rs11156803 | rs17462688 | rs7064826 | rs995895 |
| rs7601672 | rs6808996 | rs10062935 | rs7783383 | rs7045369 | rs4487345 | rs12884688 | rs11870700 | rs1266320 | rs1547727 |
| rs10490207 | rs9869897 | rs10478040 | rs4722417 | rs10757394 | rs12807746 | rs1058010 | rs11655981 | rs6641094 | rs6877 |
| rs9309192 | rs4680967 | rs256249 | rs6966737 | rs10966093 | rs7481199 | rs1952198 | rs7220430 | rs1731475 | rs12008689 |
| rs10184594 | rs1561162 | rs329312 | rs38488 | rs824230 | rs621310 | rs11625855 | rs7230740 | rs1731470 | rs1882713 |
| rs11885364 | rs729942 | rs329317 | rs10272887 | rs928484 | rs11021014 | rs11159087 | rs1402630 | rs5955621 | rs5925038 |
| rs13427078 | rs959132 | rs2069882 | rs739981 | rs1115553 | rs11021018 | rs10483899 | rs1940615 | rs5909069 | rs17253949 |
| rs6545738 | rs635268 | rs17169344 | rs7790537 | rs3780169 | rs1791459 | rs1112573 | rs12185468 | rs6633148 | rs5970118 |
| rs1503236 | rs6439419 | rs2347577 | rs10250368 | rs17520103 | rs1625749 | rs12432856 | rs9947725 | rs2283712 | rs5924705 |
| rs6704741 | rs1466827 | rs10040966 | rs12701041 | rs495259 | rs11216930 | rs8008554 | rs930926 | rs5955648 | rs5925082 |
| rs1517862 | rs2052832 | rs152523 | rs2392151 | rs605683 | rs17748 | rs17259779 | rs8083849 | rs2122 | rs4828733 |
| rs11887934 | rs347965 | rs6881655 | rs2598105 | rs662975 | rs11216943 | rs1286496 | rs12961249 | rs6633552 | rs2071122 |
| rs4549098 | rs10513320 | rs1025489 | rs12701773 | rs567490 | rs4936507 | rs12893100 | rs206416 | rs16982185 | rs3747309 |
| rs7558702 | rs391398 | rs302401 | rs2119053 | rs985654 | rs7130937 | rs17099646 | rs3816822 | rs6653666 | rs5940453 |
| rs1459166 | rs6793037 | rs10516032 | rs4720500 | rs11142769 | rs4282990 | rs4906007 | rs11083004 | rs5925647 | MitoG12373A |

TABLE 16

SNP Panel of 1000 SNPs for classifying CVID case with OSAI (organ specific autoimmunity) versus CVID case without OSAI

| | | | | | | | | | |
|---|---|---|---|---|---|---|---|---|---|
| rs2297829 | rs16838906 | rs4274923 | rs7718152 | rs3912067 | rs2927572 | rs6589426 | rs1012016 | rs2850451 | rs5951587 |
| rs2275875 | rs1876110 | rs9291598 | rs10059157 | rs7805441 | rs1536950 | rs11214983 | rs7156281 | rs9949880 | rs5926216 |
| rs6699993 | rs10489999 | rs187196 | rs7719533 | rs4730345 | rs957903 | rs7116557 | rs1840790 | rs11150900 | rs12011998 |
| rs11580688 | rs7562525 | rs4351004 | rs2400176 | rs2371366 | rs784790 | rs1379230 | rs11661755 | rs6653559 |
| rs1005301 | rs1431900 | rs10025482 | rs17640419 | rs17156818 | rs10759209 | rs4936297 | rs12885991 | rs12605082 | rs5985835 |
| rs12023073 | rs1406665 | rs10939265 | rs2277025 | rs2106277 | rs7031681 | rs7112940 | rs1587351 | rs12461534 | rs3997122 |
| rs533808 | rs1147148 | rs2687968 | rs412805 | rs2213979 | rs10978723 | rs2298767 | rs4774966 | rs1428752 | rs5985846 |
| rs2997447 | rs1226906 | rs2249563 | rs394378 | rs6972034 | rs7871882 | rs743632 | rs11632793 | rs10413521 | rs1921501 |
| rs3008418 | rs11147155 | rs2732063 | rs10516028 | rs17153071 | rs784683 | rs4937230 | rs7179813 | rs3786521 | rs5985847 |
| rs12069719 | rs438027 | rs1706023 | rs868103 | rs11772805 | rs784676 | rs7933438 | rs11637130 | rs6509637 | rs1500727 |
| rs2783711 | rs4476347 | rs1812922 | rs4640812 | rs1404228 | rs784667 | rs7948482 | rs11637277 | rs1366257 | rs7065783 |
| rs17257170 | rs10203019 | rs10518221 | rs10038486 | rs777183 | rs7034018 | rs10790952 | rs2917821 | rs2561008 | rs5971516 |
| rs1325281 | rs1010491 | rs6857026 | rs248230 | rs7797250 | rs7034341 | rs11221388 | rs12915827 | rs7245993 | rs2692983 |
| rs12136144 | rs6707140 | rs4271959 | rs9393002 | rs10488631 | rs13287637 | rs7115037 | rs8025474 | rs11881864 | rs2692992 |
| rs297802 | rs1446928 | rs11727192 | rs9379231 | rs12531711 | rs10306141 | rs4937653 | rs11071986 | rs1935386 | rs6527180 |
| rs1542885 | rs10173407 | rs11099542 | rs6934943 | rs1426499 | rs10987414 | rs11222975 | rs7172828 | rs6052956 | rs5927097 |
| rs1888696 | rs6708774 | rs12650438 | rs1905214 | rs12707357 | rs7047329 | rs1868534 | rs6495460 | rs1629176 | rs2748312 |

TABLE 16-continued

SNP Panel of 1000 SNPs for classifying CVID case with OSAI (organ specific autoimmunity) versus CVID case without OSAI

| | | | | | | | | | |
|---|---|---|---|---|---|---|---|---|---|
| rs6426015 | rs7422573 | rs955999 | rs9504663 | rs918892 | rs4564007 | rs3016390 | rs3935740 | rs6085968 | rs6628742 |
| rs11264024 | rs1479545 | rs11731687 | rs201033 | rs1731913 | rs4363310 | rs3019650 | rs1602537 | rs6055504 | rs16998378 |
| rs1148945 | rs2728075 | rs260899 | rs9383054 | rs7790696 | rs9411334 | rs11836987 | rs10220733 | rs4816043 | rs199905 |
| rs784600 | rs1973683 | rs9307215 | rs2299054 | rs3807570 | rs7026534 | rs11047560 | rs2008262 | rs6133544 | rs5917660 |
| rs11211091 | rs7648792 | rs1215049 | rs2299048 | rs4725704 | rs9411438 | rs11171662 | rs10438428 | rs6055520 | rs206033 |
| rs3219484 | rs359030 | rs783925 | rs2299045 | rs903900 | rs1889915 | rs11171786 | rs2241645 | rs2179984 | rs12556250 |
| rs17265796 | rs3846121 | rs783963 | rs3778652 | rs7805359 | rs7904615 | rs11171949 | rs12595786 | rs2269027 | rs5963167 |
| rs787499 | rs4685240 | rs2555390 | rs4510659 | rs12674335 | rs4880904 | rs12819124 | rs8037423 | rs6075458 | rs5963767 |
| rs787503 | rs7639807 | rs2903153 | rs13211187 | rs12677675 | rs11251234 | rs1476607 | rs7179643 | rs6081476 | rs5963172 |
| rs12069919 | rs1513755 | rs6854802 | rs2275906 | rs12546671 | rs661891 | rs10875753 | rs2879828 | rs6046482 | rs2939581 |
| rs787497 | rs4973727 | rs10006414 | rs16867901 | rs10503603 | rs10904616 | rs10877323 | rs7164787 | rs2328472 | rs2948491 |
| rs787492 | rs17007866 | rs17216080 | rs16867911 | rs7386698 | rs10904623 | rs7959640 | rs1828481 | rs7268341 | rs3008962 |
| rs787486 | rs12491696 | rs9307239 | rs9295739 | rs1047406 | rs1417032 | rs1480180 | rs7172789 | rs7261602 | rs2939564 |
| rs12039098 | rs3890082 | rs9991722 | rs9468202 | rs1047398 | rs12761228 | rs1480181 | rs1353576 | rs6119437 | rs7060889 |
| rs1486087 | rs535689 | rs916913 | rs6915101 | rs17404749 | rs12357990 | rs17112001 | rs11168248 | rs6088393 | rs12837663 |
| rs6593584 | rs681025 | rs4441771 | rs200959 | rs1662248 | rs942531 | rs6539695 | rs2060060 | rs2038123 | rs851223 |
| rs12733869 | rs680930 | rs582448 | rs2499450 | rs327235 | rs2478112 | rs10466960 | rs10220773 | rs17332951 | rs4824747 |
| rs841669 | rs549968 | rs1486973 | rs3814071 | rs327232 | rs4748050 | rs7302697 | rs4583204 | rs10485505 | rs401591 |
| rs6689027 | rs512541 | rs4293833 | rs3777543 | rs1481758 | rs2025718 | rs1543169 | rs1431234 | rs760998 | rs241748 |
| rs9428050 | rs537660 | rs586090 | rs1507912 | rs1545961 | rs9651540 | rs2056218 | rs4313781 | rs6072090 | rs241742 |
| rs553314 | rs9310709 | rs7696023 | rs3957360 | rs16879142 | rs11012422 | rs7960163 | rs6496332 | rs11086875 | rs241740 |
| rs10735234 | rs9826441 | rs12504357 | rs239794 | rs13282541 | rs11598403 | rs10778309 | rs10520630 | rs12479650 | rs17302689 |
| rs499345 | rs9818043 | rs3796590 | rs9345994 | rs11994501 | rs11009254 | rs7976552 | rs715922 | rs911952 | rs5951221 |
| rs21327 | rs7627134 | rs7668220 | rs6455228 | rs1568135 | rs6481837 | rs11068326 | rs2163442 | rs666753 | rs4986620 |
| rs1814653 | rs2372250 | rs10030326 | rs1157977 | rs1517118 | rs12768519 | rs10850758 | rs2448929 | rs6513239 | rs5951181 |
| rs2769267 | rs7612515 | rs4691394 | rs1025534 | rs1549459 | rs4240498 | rs10850759 | rs731597 | rs1007725 | rs4986597 |
| rs12410758 | rs6772285 | rs6840872 | rs1655365 | rs7014791 | rs16937609 | rs10850760 | rs1371390 | rs4812180 | rs5951214 |
| rs1027493 | rs11918364 | rs7694824 | rs13205488 | rs7004470 | rs7918437 | rs7299612 | rs1025768 | rs1201916 | rs4986610 |
| rs6672415 | rs4955377 | rs17534473 | rs1890278 | rs7815631 | rs6481383 | rs7314278 | rs1371391 | rs13042560 | rs7055300 |
| rs6427832 | rs7637194 | rs17475331 | rs9373923 | rs7815950 | rs1867571 | rs1268892 | rs10048024 | rs2426977 | rs2428414 |
| rs3738287 | rs9853319 | rs6825169 | rs9487538 | rs3016889 | rs1416764 | rs838913 | rs11635251 | rs1884854 | rs239902 |
| rs10800777 | rs11922288 | rs4695771 | rs17679624 | rs2470002 | rs714113 | rs838916 | rs8039888 | rs2426987 | rs6616403 |
| rs10800779 | rs11713329 | rs7659511 | rs17057836 | rs2470012 | rs1416767 | rs826723 | rs757108 | rs6015934 | rs5922869 |
| rs823105 | rs6599210 | rs1347700 | rs17185166 | rs2447167 | rs3851235 | rs10848159 | rs2283479 | rs6129079 | rs825541 |
| rs3890801 | rs4676595 | rs4362867 | rs4897579 | rs11778912 | rs10999626 | rs10751692 | rs233948 | rs6028076 | rs1531868 |
| rs11587049 | rs9868689 | rs869570 | rs1209415 | rs4242335 | rs11001790 | rs12319878 | rs7186783 | rs1735484 | rs5968255 |
| rs7546886 | rs2191028 | rs6883247 | rs726794 | rs7813708 | rs1907333 | rs2476509 | rs12927837 | rs2822744 | rs10218349 |
| rs11590870 | rs2191027 | rs1875195 | rs11965233 | rs11779458 | rs1907303 | rs520000 | rs933488 | rs7282227 | rs765076 |
| rs7542307 | rs4299518 | rs4075798 | rs9376674 | rs4512366 | rs17772401 | rs348222 | rs2312949 | rs2824332 | rs7878135 |
| rs753961 | rs6794124 | rs10512785 | rs4895598 | rs3812475 | rs3847452 | rs9532874 | rs4871120 | rs2824335 | rs5968299 |
| rs7367845 | rs724334 | rs493944 | rs6930478 | rs4128468 | rs10509532 | rs9532877 | rs7403964 | rs17801179 | rs5968301 |
| rs4304564 | rs1911746 | rs12153548 | rs13191080 | rs2648836 | rs10788575 | rs1555587 | rs8048521 | rs2833979 | rs6418331 |
| rs10079344 | rs1406611 | rs31887 | rs4870010 | rs2648847 | rs7084813 | rs9535207 | rs7199993 | rs9974198 | rs1000505 |
| rs10489802 | rs9878456 | rs7710236 | rs7745737 | rs2909239 | rs6583692 | rs9536203 | rs16960659 | rs2252046 | rs5939564 |
| rs12353954 | rs4131544 | rs7706312 | rs851991 | rs2975520 | rs7911956 | rs9569174 | rs2519975 | rs9979659 | rs7050797 |
| rs4649442 | rs3910485 | rs27466 | rs890458 | rs11166726 | rs2147878 | rs2316640 | rs8055835 | rs2849684 | rs675270 |
| rs1881548 | rs9831003 | rs32376 | rs645851 | rs7845645 | rs12766594 | rs4274330 | rs3213881 | rs9306194 | rs595679 |
| rs6678625 | rs4855179 | rs10066628 | rs979289 | rs2487999 | rs2321995 | rs7191446 | rs5747145 | rs10521528 | |
| rs17640830 | rs1437238 | rs1494621 | rs12197625 | rs10107665 | rs723483 | rs4132047 | rs11648791 | rs5746398 | rs12855355 |
| rs887962 | rs12638978 | rs4301212 | rs1476041 | rs6578102 | rs12415142 | rs17080881 | rs9939233 | rs1004973 | rs676579 |
| rs2380431 | rs6774951 | rs2662266 | rs903791 | rs10759031 | rs1538080 | rs10507731 | rs8050239 | rs5747176 | rs640009 |
| rs6733870 | rs17826288 | rs7708845 | rs9365899 | rs324526 | rs7919239 | rs1023033 | rs4405545 | rs4819591 | rs11152747 |
| rs7564116 | rs709496 | rs1500238 | rs6455419 | rs88818 | rs10128498 | rs17082395 | rs7202571 | rs5992761 | rs6643108 |
| rs6744117 | rs709477 | rs6594343 | rs1626670 | rs12156538 | rs9418990 | rs1537547 | rs8063008 | rs134510 | rs12839137 |
| rs4669995 | rs697957 | rs17412225 | rs10230651 | rs649891 | rs2141322 | rs9565348 | rs1476460 | rs9609551 | rs5905284 |
| rs11895101 | rs10511323 | rs1423456 | rs12670634 | rs10756313 | rs217766 | rs7320056 | rs17806045 | rs670264 | rs4825645 |
| rs4669999 | rs4682479 | rs7711677 | rs7797010 | rs1978746 | rs7936055 | rs2775133 | rs205043 | rs728797 | rs6603535 |
| rs1395 | rs1837206 | rs7714521 | rs1505335 | rs4401960 | rs17761158 | rs1324770 | rs1870584 | rs5915542 | rs5911118 |
| rs10496179 | rs6806321 | rs42670 | rs12703012 | rs7037514 | rs10838249 | rs2026840 | rs4796033 | rs5916081 | rs16996610 |
| rs13021944 | rs4234209 | rs6871668 | rs2107140 | rs10811312 | rs7939723 | rs1324791 | rs2280784 | rs11094994 | rs2840649 |
| rs2177098 | rs1384566 | rs13354840 | rs17164591 | rs7866455 | rs10791889 | rs6563154 | rs12103666 | rs7055627 | rs983007 |
| rs2140039 | rs4679142 | rs1487216 | rs11771731 | rs7854529 | rs4930390 | rs1113104 | rs9899005 | rs1450154 | rs12557782 |
| rs2861680 | rs970494 | rs10056192 | rs1019171 | rs1563950 | rs3741194 | rs4884202 | rs4792901 | rs1450152 | rs5932693 |
| rs10520218 | rs6807545 | rs7726250 | rs10950426 | rs13290599 | rs7104011 | rs1535989 | rs11655764 | rs5989530 | rs4269687 |
| rs1992886 | rs12487078 | rs10071150 | rs1548741 | rs13297389 | rs12421802 | rs9357994 | rs12953076 | rs5989531 | rs2886973 |
| rs6748174 | rs13093879 | rs9765600 | rs4721160 | rs1013217 | rs1151220 | rs9520140 | rs792766 | rs1026162 | rs4829963 |
| rs3218984 | rs9864846 | rs1524566 | rs217601 | rs2481061 | rs2373711 | rs9555701 | rs2049534 | rs1015496 | rs5974805 |
| rs7589525 | rs524554 | rs6865072 | rs36843 | rs10813971 | rs10897739 | rs17122962 | rs7210515 | rs5978969 | rs5908057 |
| rs13401717 | rs531617 | rs13167682 | rs36920 | rs13287406 | rs7127610 | rs1950950 | rs9892439 | rs5978974 | rs1120947 |
| rs11685896 | rs7625382 | rs2218717 | rs10227084 | rs616009 | rs7948940 | rs1570164 | rs7218480 | rs2404797 | rs2223457 |
| rs1442774 | rs9827666 | rs1524560 | rs1476944 | rs7861989 | rs3824933 | rs10483412 | rs10512540 | rs6530209 | rs11798497 |
| rs4849721 | rs9833887 | rs1524559 | rs2192484 | rs776021 | rs4396256 | rs8012446 | rs898095 | rs17222040 | rs5908792 |
| rs1527420 | rs7618620 | rs1524561 | rs9648629 | rs4878743 | rs11224780 | rs12586232 | rs7209936 | rs929228 | rs5953883 |
| rs4662982 | rs9879759 | rs6891778 | rs985307 | rs1421156 | rs7948300 | rs1571106 | rs16941996 | rs6638877 | rs6654220 |
| rs2677646 | rs2242338 | rs716815 | rs4721784 | rs656875 | rs11822192 | rs6573233 | rs6506135 | rs5935341 | rs5908801 |
| rs12475202 | rs12495729 | rs1992951 | rs6461547 | rs1899937 | rs11224783 | rs10139749 | rs8083753 | rs5935343 | rs5936357 |
| rs10930958 | rs6799976 | rs10477215 | rs1859103 | rs7863238 | rs12362157 | rs741518 | rs675881 | rs3863537 | rs4090449 |
| rs1962276 | rs13086529 | rs13156143 | rs9638797 | rs11143520 | rs7117447 | rs2619676 | rs676968 | rs11095604 | rs12388487 |

TABLE 16-continued

SNP Panel of 1000 SNPs for classifying CVID case with OSAI (organ specific autoimmunity) versus CVID case without OSAI

| | | | | | | | | | |
|---|---|---|---|---|---|---|---|---|---|
| rs12474703 | rs16859685 | rs325231 | rs12700427 | rs2479835 | rs7124340 | rs162171 | rs1403753 | rs5934075 | rs5936468 |
| rs6754105 | rs12493115 | rs17415614 | rs882101 | rs12351660 | rs4754161 | rs327434 | rs3861809 | rs1921931 | rs237370 |
| rs5008216 | rs4687488 | rs2636112 | rs2074137 | rs7855727 | rs17105869 | rs162174 | rs17064241 | rs6527755 | rs3761562 |
| rs1037091 | rs7637593 | rs1096980 | rs7779755 | rs10867947 | rs4245155 | rs7158936 | rs4362477 | rs5909379 | rs1472977 |
| rs10185386 | rs4527429 | rs3792815 | rs6978786 | rs10115014 | rs11601037 | rs1617580 | rs7231765 | rs12850925 | rs4898398 |

Example 3

Exome Sequencing Identifies Missense IRF2BP2 Mutation in a Family with Autosomal Dominant Common Variable Immunodeficiency (CVID)

Common Variable Immunodeficiency (CVID) is among the most frequently diagnosed forms of primary immunodeficiency disorders (PIDD), and is the most frequent requiring clinical intervention. Defined clinically by low quantity of two immunoglobulin classes (including IgG) and poor specific antibody production, it has been thought of as an "umbrella diagnosis" due to the heterogeneity of its onset and co-morbidities, including autoimmune disease and risk of malignancy. Though thought to be polygenic, roughly 10% of CVID is familial, and in recent years, 11 gene causes and/or associations with CVID have been described (Table 17).

TABLE 17

CVID Gene Associations

| Function | Gene | Ref. |
|---|---|---|
| BCR function | CD19 | Van Zelm, MC, et al. *NEJM* 2006 |
| | CD20 | Kuijpers TW, et al. *JCI* 2010 |
| | CD21 | Thiel J, et al. *JACI* 2012 |
| | CD81 | Van Zelm MC, et al. *JCI* 2010. |
| B-cell co-stimulation | TACI | Martinez-Gallo M, et al. *JACI* 2013 |
| | ICOS | Grimbacher B, et al. *Nat Immunol* 2003 |
| | BAFFR | Warnatz H, et al. *Proc Natl Acad Sci* 2009 |
| | CD27 | Van Montfrans J, et al. *JACI* 2012 |
| DNA repair/ VDJ recombination | MSH5 | Sekine H, et al. *Proc Natl Acad Sci* 2007 |
| B-cell survival/ differentiation | LRBA | Lopez-Herrera G, et al. *Am J Hum Genet* 2012 |
| TCR/BCR signaling | PLCγ2 | Ombrello MJ, et al. *NEJM* 2012 |

As discussed above in the previous examples, a recent multi-institutional genome-wide array study of CVID showed unique associations with specific single nucleotide polymorphisms (SNP) and copy number variants (CNV), with intraexonic duplications in ORC4L being most highly associated with disease. Beyond individual associations, CVID has a unique pattern of SNP and CNV, as suggested by the successful use of a Support Vector Machine (SVM) algorithm to identify this pattern in CVID patients and controls. SVM can be trained with a variety of data, and produces a "hyperplane" for subsequent classification. In the studies described above, the CVID SVM hyperplane successfully classified cases with an accuracy of 91%, PPV 100%, and NPV 96%.

Though the use of SVM supports the polygenic nature of CVID, a remaining question was whether monogenic CVID would lack the genetic fingerprint of the more common polygenic disease. If this were the case, SVM classification of microarray data would incorrectly classify these individuals as not affected, and could therefore be a useful screening method for monogenic CVID, most notably in familial cases. Accordingly additional studies were undertaken.

Patients

Patients were enrolled in research protocols approved by the host institutional review board to allow genetic analysis and clinical data collection.

Clinical History

The proband is a young woman who experienced recurrent sinopulmonary infections beginning in early adolescence. Evaluation at age 19 years showed IgG 620 mg/dl (normal range 635-1775 mg/dL), undetectable IgM and IgA (normal ranges 71-237 and 70-486 mg/dL respectively), and poor specific antibody production following vaccination to *S. pneumoniae* (1 of 14 serotypes >1.3 mcg/ml) and *N. meningitidis* (0 of 4 strains protective). Lymphocyte subsets were normal in number with $CD19^+$ 388 cell/mcl (normal range 100-570), though switched memory B-cells ($CD19^+$ $IgD^-CD27^+$) were low at 0.4% (normal >0.5%). She has been maintained on subcutaneous immunoglobulin with good control of infections, and has no autoimmune disease.

Figure 11:
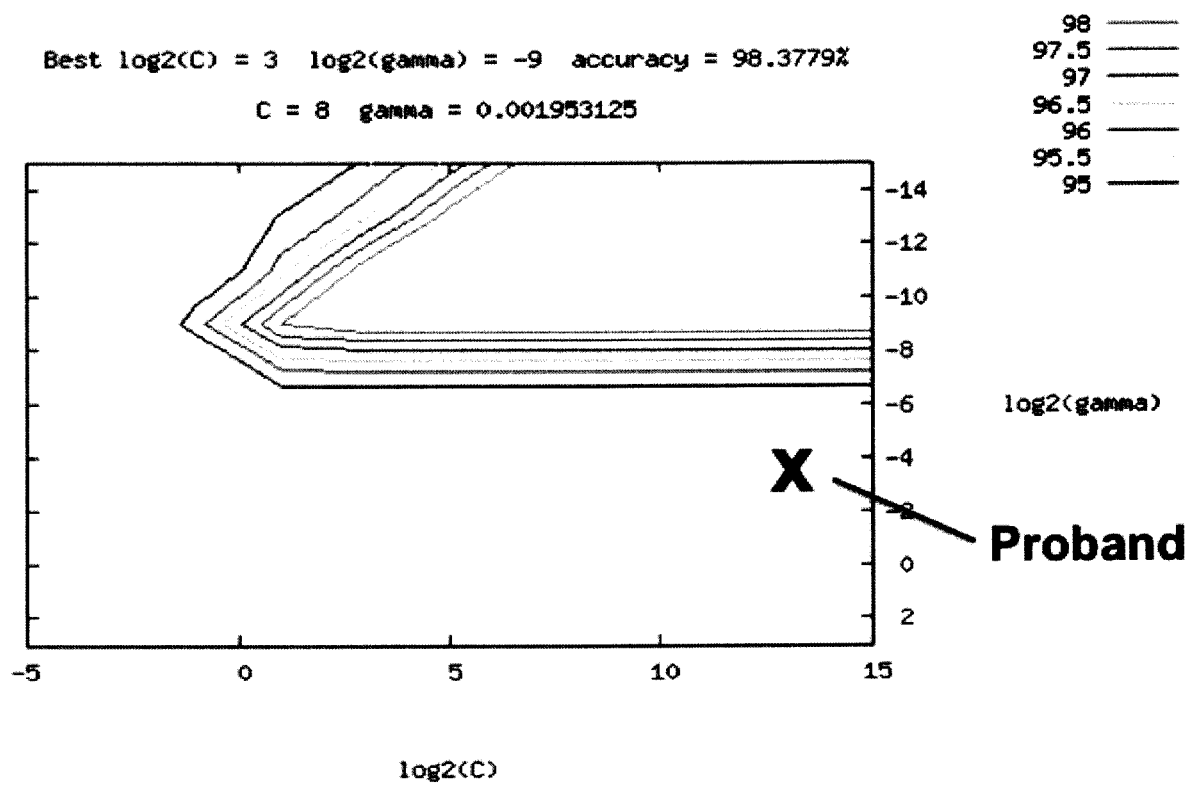

Her family history is notable for CVID in both her father as well as her older brother (FIG. 11). Her father also has a history of psoriasis, and her brother has type I diabetes. Her paternal grandparents, aunts, and their families are unaffected, as is her maternal family.

Genetic Studies

High throughput SNP genotyping was performed with the Infinitium HumanHap610 Beadchip, and the PennCNV algorithm was used for CNV calls. A support vector machine algorithm was trained with data from 179 CVID cases and 1917 controls, utilizing the 658 most significantly associated variants from the 2011 study, and subsequently tested on the patient.

Whole-exome sequencing using the Agilent SureSelect Human All Exon 50 Mb kit was performed on the patient and her family. Variants were matched to disease segregation (which suggested a heterozygous, autosomal dominant pattern), and further narrowed by exclusion of synonymous mutations, in silico analysis of mutation impact, exclusion of SNPs in public databases (1000 Genomes and NHLBI 5400 exomes Project), tissue expression pattern (BioGPS.org), and ties to known immunologic pathways.

RT-PCR and Immunoblotting

RNA was isolated from whole blood obtained from the patient and controls via Trizol reagent (Applied Biosystems, Grand Island, N.Y.) and RNEasy kit (Qiagen, Germantown, Md.). cDNA was produced via high capacity Reverse Transcriptase kit (Applied Biosystems), and custom cDNA primers for IRF2BP2 (both total and isoform 2) and GAPDH were created. RT-PCR performed via SYBR Green core reagents on a QPCR 7900HT system. Gene dose was calculated via DDCT method.

Protein immunoblotting was performed on lymphoblasts derived from peripheral blood mononuclear cells via treatment with phytohemagglutanin (2 ug/ml) and IL-2 (500

IU/ml). Antibodies against IRF2BP2 and TATA binding protein (Abcam, Cambridge, Mass.) were used.

Support Vector Machine Hyperplane Classification

Analysis of the top 658 SNP/CNVs by the pre-trained CVID SVM algorithm predicted that the patient was not affected (FIG. 11).

Whole Exome Sequencing

Figure 12:
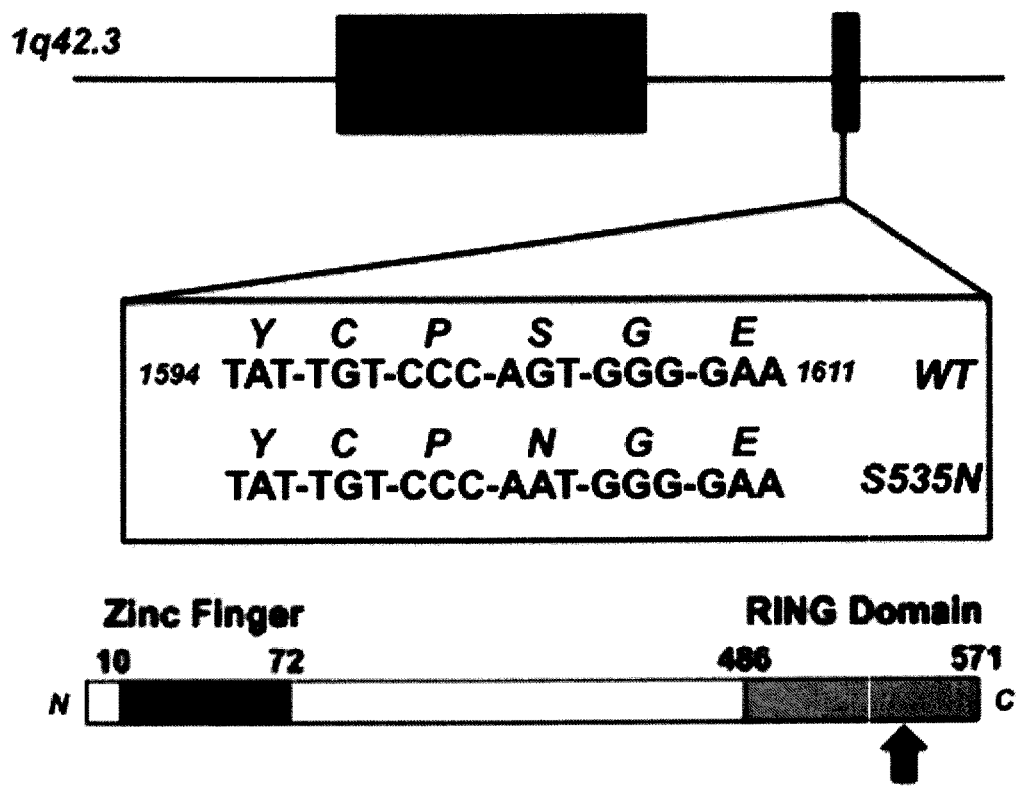
FIG. 12. S535N mutation in IRF2BP2.

Sequencing of the proband revealed 12 non-synonymous, rare variants, of which 5 were predicted to be damaging via in silico analysis (SIFT, polyphen2). Three variants (AMBP, IRF2BP2, and PIK3C2G) had been tied to immunologic pathways. Sanger sequencing of IRF2BP2 in the proband and family confirmed that a heterozygous S535N mutation was present in all affected family members, and none of those who were unaffected. This mutation is in the RING domain of the protein, which has been described as the region of interaction with IRF2 and NFAT1 [3]. See FIG. 12.

RT-PCR of IRF2BP2

Figure 13:
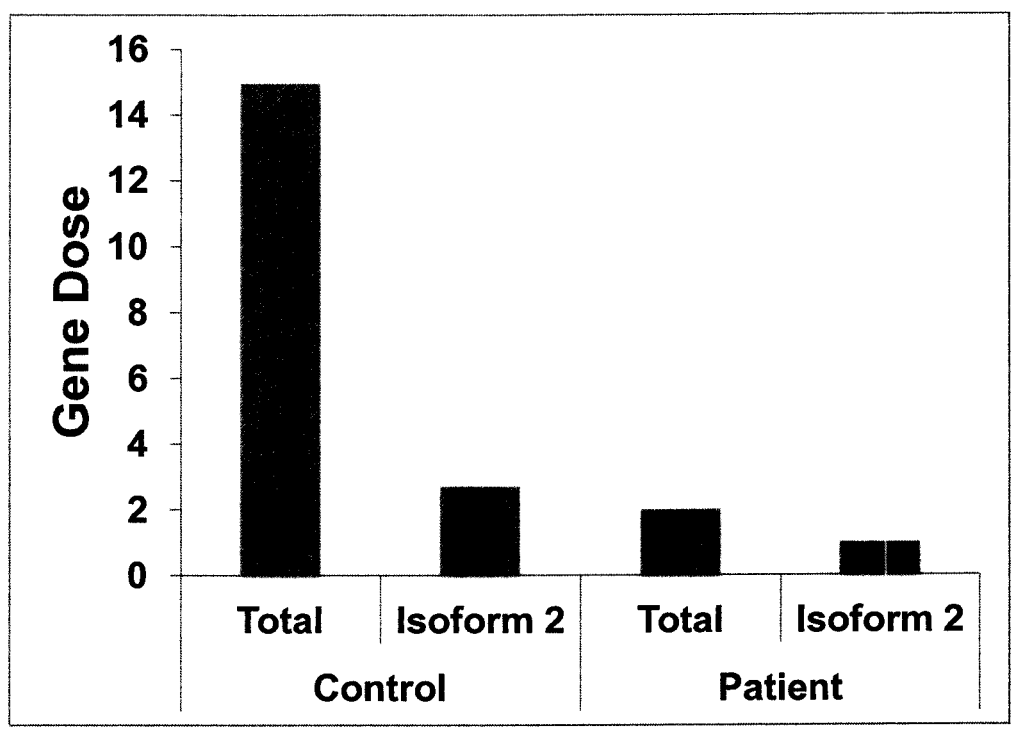
FIG. 13. RT-PCR or IRF2BP2.

Quantitative PCR of IRF2BP2 from patient and control peripheral blood showed a lower transcript quantity in the patient versus normal control (FIG. 13). In the normal control, Isoform 1 was predominant, with comparatively less transcripts of Isoform 2 (which differs by exon 1 length). In the patient, isoform expression was roughly equal.

These results reveal that learning algorithms such as SVM provide a valuable method of screening for monogenic diseases within polygenic populations by searching for differences in the genetic pattern of SNP and rare CNV. In the field of PIDD, this is particularly useful for screening for monogenic causes of early-onset autoimmune disease such as type I diabetes or inflammatory bowel disease.

Moreover, these studies reveal that the presence of a SNP in IRF2BP2 on chromosome 1 at position 234742995 is indicative of a new CVID-associated candidate gene.

Example 4

The information herein above can be applied clinically to patients for diagnosing an increased susceptibility for developing CVID, and therapeutic intervention. A preferred embodiment of the invention comprises clinical application of the information described herein to a patient. Diagnostic compositions, including microarrays, and methods can be designed to identify the genetic alterations described herein in nucleic acids from a patient to assess susceptibility for developing CVID. This can occur after a patient arrives in the clinic; the patient has blood drawn, and using the diagnostic methods described herein, a clinician can detect one or more indicative SNPs or CNVs described in the Tables hereinabove. The information obtained from the patient sample, which can optionally be amplified prior to assessment, will be used to diagnose a patient with an increased or decreased susceptibility for developing CVID. Kits for performing the diagnostic method of the invention are also provided herein. Such kits comprise a microarray comprising at least one of the SNPs provided herein in and the necessary reagents for assessing the patient samples as described above.

The identity of CVID-involved genes and the patient results will indicate which variants are present, and will identify those that possess an altered risk for developing CVID. The information provided herein allows for therapeutic intervention at earlier times in disease progression that previously possible. For example, agents such as STA-5326, sotatercept, PF3446962, PEG-interleukin-2 and B-lymphocyte stimulators can be administered as appropriate.

Also as described herein above, several new genes involved in CVID pathogenesis have been identified which provide novel targets for the development of new therapeutic agents efficacious for the treatment of CVID.

While certain of the preferred embodiments of the present invention have been described and specifically exemplified above, it is not intended that the invention be limited to such embodiments. It will be apparent to one skilled in the art that various changes and modifications can be made therein without departing from the scope of the present invention, as set forth in the following claims.

What is claimed is:

1. A solid support for detecting at least one common variable immunodeficiency (CVID)-associated copy number variation (CNV) in a sample comprising immobilized nucleic acid probes or primers of 15 or more nucleotides in length, wherein each of said probes or primers present on said solid support specifically hybridize to CVID specific nucleic acids in chromosomal regions consisting of chr11: 85365857-85381622, chr20: 57735790-57741780, chr22: 17396663-18417315, chr4: 10256682-10264316, and chr10: 46003146-46042543, chr2: 148396730-148433180, chr15: 35053039-35063531, chr7: 91789778-91801963, chr2: 163316298-163316595, chr7: 87180702-87191931, and, optionally, one or more of chr19: 9256584-9277749, chr4: 39190766-39201960, chr7: 18903915-18905725, chr5: 170531269-170536993, chr7: 34685030-34686172, and chr1: 170400944-170403742.

2. A kit comprising the solid support of claim 1 and reagents for detecting hybridization of nucleic acids to said solid support.

* * * * *